(12) United States Patent
Xiang et al.

(10) Patent No.: US 8,324,272 B2
(45) Date of Patent: Dec. 4, 2012

(54) LEVODOPA DIMETHYL-SUBSTITUTED DIESTER PRODRUGS, COMPOSITIONS, AND METHODS OF USE

(75) Inventors: Jia-Ning Xiang, Palo Alto, CA (US);
Cindy X. Zhou, Palo Alto, CA (US);
Fenmei Yao, Mountain View, CA (US);
Mark Q. Nguyen, San Jose, CA (US)

(73) Assignee: XenoPort, Inc., Santa Clara, CA (US)

( * ) Notice: Subject to any disclaimer, the term of this patent is extended or adjusted under 35 U.S.C. 154(b) by 252 days.

(21) Appl. No.: 12/726,978

(22) Filed: Mar. 18, 2010

(65) Prior Publication Data
US 2010/0173992 A1 Jul. 8, 2010

Related U.S. Application Data

(63) Continuation of application No. 12/005,117, filed on Dec. 20, 2007, now Pat. No. 7,709,527.

(60) Provisional application No. 60/876,144, filed on Dec. 21, 2006, provisional application No. 60/967,773, filed on Sep. 7, 2007.

(51) Int. Cl.
*A61K 31/235* (2006.01)
*C07C 229/36* (2006.01)

(52) U.S. Cl. .......................... 514/533; 560/40

(58) Field of Classification Search .................. None
See application file for complete search history.

(56) References Cited

U.S. PATENT DOCUMENTS

| | | | |
|---|---|---|---|
| 3,811,444 A | 5/1974 | Heller et al. | |
| 3,845,770 A | 11/1974 | Theeuwes et al. | |
| 3,916,899 A | 11/1975 | Theeuwes et al. | |
| 3,962,414 A | 6/1976 | Michaels | |
| 3,992,518 A | 11/1976 | Chien et al. | |
| 4,038,411 A | 7/1977 | Saari | |
| 4,066,747 A | 1/1978 | Capozza | |
| 4,070,347 A | 1/1978 | Schmitt | |
| 4,079,038 A | 3/1978 | Choi et al. | |
| 4,083,949 A | 4/1978 | Benedikt | |
| 4,093,709 A | 6/1978 | Choi et al. | |
| 4,134,991 A | 1/1979 | Wermuth et al. | |
| 4,180,509 A | 12/1979 | Metcalf et al. | |
| 4,311,706 A | 1/1982 | Bodor et al. | |
| 4,663,349 A | 5/1987 | Repta | |
| 4,771,073 A | 9/1988 | Repta | |
| 4,826,875 A | 5/1989 | Chiesi | |
| 4,873,263 A | 10/1989 | Repta | |
| 4,879,303 A * | 11/1989 | Davison et al. ............... | 514/356 |
| 4,914,222 A | 4/1990 | Budavari et al. | |
| 4,966,915 A | 10/1990 | Tsuchiya et al. | |
| 4,983,400 A | 1/1991 | Dempski et al. | |
| 5,017,607 A | 5/1991 | Chiesi | |
| 5,057,321 A | 10/1991 | Edgren et al. | |
| 5,073,641 A | 12/1991 | Bundgaard et al. | |
| 5,128,145 A | 7/1992 | Edgren et al. | |
| 5,133,974 A | 7/1992 | Paradissis et al. | |
| 5,190,763 A | 3/1993 | Edgren et al. | |
| 5,283,352 A | 2/1994 | Backstrom et al. | |
| 5,332,576 A | 7/1994 | Mantelle | |
| 5,462,933 A | 10/1995 | Kramer et al. | |
| 5,607,969 A | 3/1997 | Milman et al. | |
| 5,698,155 A | 12/1997 | Grosswald et al. | |
| 5,827,819 A | 10/1998 | Yatvin et al. | |
| 5,840,756 A | 11/1998 | Cohen et al. | |
| 6,696,600 B2 | 2/2004 | Frenkel et al. | |
| 7,101,912 B2 | 9/2006 | Xiang et al. | |
| 7,323,585 B2 | 1/2008 | Xiang et al. | |
| 7,342,131 B2 | 3/2008 | Xiang et al. | |
| 7,534,813 B2 | 5/2009 | Xiang et al. | |
| 7,563,821 B2 | 7/2009 | Xiang et al. | |
| 7,671,089 B2 | 3/2010 | Xiang et al. | |
| 7,709,527 B2 | 5/2010 | Xiang et al. | |
| 2002/0099041 A1 | 7/2002 | Gallop et al. | |
| 2003/0152628 A1 | 8/2003 | Licht et al. | |
| 2003/0158254 A1 | 8/2003 | Zerangue et al. | |
| 2005/0209181 A1 | 9/2005 | Akil et al. | |
| 2005/0282891 A1 | 12/2005 | Xiang et al. | |
| 2006/0020028 A1 | 1/2006 | Xiang et al. | |
| 2007/0225366 A1 | 9/2007 | Xiang et al. | |
| 2008/0070984 A1 | 3/2008 | Tran et al. | |
| 2008/0103200 A1 | 5/2008 | Xiang et al. | |
| 2008/0132570 A1 | 6/2008 | Xiang et al. | |
| 2008/0171789 A1 | 7/2008 | Xiang et al. | |
| 2008/0214663 A1 | 9/2008 | Xiang et al. | |
| 2009/0137834 A1 | 5/2009 | Xiang et al. | |
| 2009/0156679 A1 | 6/2009 | Xiang et al. | |
| 2010/0099761 A1 | 4/2010 | Karaborni et al. | |
| 2010/0099907 A1 | 4/2010 | Raillard et al. | |
| 2010/0173992 A1 | 7/2010 | Xiang et al. | |

FOREIGN PATENT DOCUMENTS

| | | |
|---|---|---|
| CA | 2 607 198 | 11/2006 |
| DE | 10 2005 022 276 A1 | 11/2006 |
| EP | 0309827 A1 | 4/1989 |
| GB | 1447599 | 8/1976 |
| GB | 1537951 | 1/1979 |
| JP | 58024547 | 2/1983 |
| WO | WO 86/04579 A1 | 8/1986 |
| WO | WO 88/01615 A1 | 3/1988 |
| WO | WO 01/68065 A2 | 9/2001 |
| WO | WO 2002/28882 A1 | 4/2002 |
| WO | WO 2007/087256 A2 | 8/2007 |

OTHER PUBLICATIONS

Airaksinen et al., Excipient selection can significantly affect sold-state phase transformation in formulation during we granulation. *AAPS PharmSciTech* 2005, 6(2), E311-E322. Carboxylic Acid Derivatives and Nitriles, http://www.chem.uky.edu/Courses/che232/JEA/In/9.%20Esters_etc.pdf, retrieved Mar. 24, 2010.

Davey et al., Polymorphism in molecular crystals: stabilization of a metastable form by conformational mimidry.*J Am Chem Soc* 1997, 119(7), 1767-1772.

"Dissolution Testing of Immediate Release Solid Oral Dosage Forms—Guidance for Industry," U.S. Department of Health and Human Services, FDA-CDER, Aug. 1997, pp. 1-17.

(Continued)

*Primary Examiner* — Paul A Zucker

(74) *Attorney, Agent, or Firm* — Kilpatrick Townsend & Stockton LLP

(57) ABSTRACT

Levodopa dimethyl-substituted diester prodrugs pharmaceutical, compositions comprising levodopa dimethyl-substituted diester prodrugs, and methods of using such prodrugs and pharmaceutical compositions for treating diseases such as Parkinson's disease are provided.

15 Claims, 2 Drawing Sheets

OTHER PUBLICATIONS

"Guidance for Industry—Bioavailability and Bioequivalence Studies for Orally Administered Drug Products—General Considerations," U.S. Department of Health and Human Services, FDA-CDER, Mar. 2003, pp. 1-26.
Olanow et al., Drug insight: continuous dopaminergic stimulation in the treatment of Parkinson's disease. *Nat Clin Pract Neurol* 2006, 2(7), 382-92.
Saari, abstract, Database CAS citation 1978:444225 [retrieved Mar. 24, 2010] from STN; Columbus, OH, USA.
Staab et al., Control of polymorphism by 'tailor-mad' polymeric crystallization auxiliaries. Preferential precipitation of a metastable polar form for second harmonic generation. *Adv Mater* 1990, 2(1), 40-43.
Office Action mailed Oct. 18, 2010, for U.S. Appl. No. 12/347,807, filed Dec. 31, 2008.
Office Action mailed Apr. 1, 2010 for U.S. Appl. No. 12/364,453, filed Feb. 2, 2009.
Office Action mailed Apr. 28, 2010 for U.S. Appl. No. 12/489,146, filed Jun. 22, 2009.
Office Action mailed May 4, 2010 for U.S. Appl. No. 12/347,807, filed Dec. 31, 2008.
Office Action, mailed Aug. 30, 2010 for U.S. Appl. No. 12/364,453, filed Feb. 2, 2009.
Notice of Allowance mailed Jun. 25, 2010, for U.S. Appl. No. 12/005,120, filed Dec. 20, 2007.
Notice of Allowance mailed Jun. 22, 2009, for U.S. Appl. No. 11/634,354, filed Dec. 4, 2006.
Notice of Allowance mailed Oct. 12, 2010, for U.S. Appl. No. 12/489,146 filed Jun. 22, 2009.
Notice of Allowance mailed Jan. 6, 2011, for U.S. Appl. No. 12/364,453.
U.S. Appl. No. 12/941,971, filed Nov. 8, 2010.
U.S. Appl. No. 13/010,419, filed Jan. 20, 2011.
U.S. Appl. No. 12/904,960, filed Oct. 14, 2010.
Alpert et al., Paradoxical reaction to L-dopa in schizophrenic patients. *Am J Psychiatry* 1978, 135(11), 1329-32.
Bai, pGlu-L-Dopa-Pro: A tripeptide prodrug targeting the intestinal peptide transporter for absorption and tissue enzymes for conversion. *Pharm. Res.* 1995, 12(7), 1101-1104.
Berge et al., Pharmaceutical salts. *J. Pharm. Sci.* 1977, 66(1), pp. 1-19.
Betarbet et al., Animal models of Parkinson's disease. *Bioessays* 2002, 24(4), 308-18.
Bodor et al., Improved delivery through biological membranes. 4. Prodrugs of L-Dopa. *J. Med. Chem.* 1977, 20(11), 1435-1445.
Boivin and Montplaisir, The effects of L-dopa on excessive daytime sleepiness in narcolepsy. *Neurology* 1991, 41, 1267-1269.
Bonelli and Wenning, Pharmacological Management of Huntington's disease: an evidence-based review, *Current Pharmaceutical Design* 2006, 12(21), 2701-2720.
Bruno and Bruno, Effects of L-dopa on pharmacological parkinsonism, *Acta Psychiatr Scand* 1966, 4(3), 264-271.
Buchanan et al., Double blind trial of L-dopa in chronic schizophrenia, *Aust N Z J Psychiatry* 1975, 9(4), 269-271.
Cho et al., Dopamine neurons derived from embryonic stem cells efficiently induce behavioral recovery in a Parkinsonian rat model. *Biochem. Biophys. Res. Commun* 2006, 341, 6-12.
Coleman et al., a practical guide to polymer miscibility. *Polymer* 1990, 31, 1187-1203.
Conti et al., Levodopa for idiopathic restless legs syndrome: evidence-based review, *Mot Disord* 2007, 22(13), 1943-1951.
Cools, Dopaminergic modulation of cognitive function-implications for L-dopa treatment in Parkinson's disease, *Neuroscience Biobehavioral Rev* 2006, 30, 1-23.
Cooper et al., L-dopa esters as potential prodrugs: behavioural activity in experimental models of Parkinson's disease, *J. Pharm. Pharmacol.* 1987, 39, 627-635.
Di Stefano et al., Dimeric L-Dopa derivatives as potential prodrugs. *Bioorganic & Medicinal Chem. Lett.* 2001, 11, 1085-1088.
Doggrell, The therapeutic potential of dopamine modulators on the cardiovascular and renal systems. *Expert Opin. Investig. Drugs*, 2002, 11(5), 631-644.

Durif et al., Worsening of levodopa-induced dyskinesias by motor and mental tasks. *Mov Disord* 1999, 14(2), 242-245.
During et al., Controlled release of dopamine from a polymeric brain implant: in vivo characterization. *Ann. Neurol.* 1989, 25(4), 351-356.
Ebadi and Srinivasan, Pathogenesis, prevention and treatment of neuroleptic-induced movement disorders, *Pharmacological Reviews* 1995, 47(4), 575-604.
Eltayb et al., Enhanced cortical dopamine output and antipsychotic-like effect of raclopride with adjunctive low-dose L-dopa. *Biol Psychiatry* 2005, 58, 337-343.
Emborg, Evaluation of animal models of Parkinson's disease for neuroprotective strategies. *J. Neuro. Meth.* 2004, 139, 121-143.
Fahn et al., Levodopa and the progression of Parkinson's disease. N. Engl J Med 2004, 351(24), 2498-2508.
Faulkner et al., Gabapentin for the treatment of tremor. *Ann. Pharmacother.* 2003, 37(2), 282-6.
Fincher, Particle size of drugs and its relationship to absorption and activity. *J. Pharm. Sci.* 1968, 57(11), 1825-1835.
Fix et al., A comparison of oral and rectal absorption of L-dopa esters in rats and mice, *Pharm. Res.* 1990, 7(4), 384-387.
Fix et al., Short-chain alkyl esters of L-dopa as prodrugs for rectal absorption, *Pharm. Res.* 1989, 6(6), 501-505.
Floel et al., Dopaminergic effects on encoding of a motor memory in chronic stroke, *Neurology* 2005, 65(3), 472-474.
Floel et al., Levodopa increases memory encoding and dopamine release in the striatum in the elderly. *Neurobiology of Aging* 2006, Pmid 17098331; 2008, 29, 267-279.
Folstein et al., A practical method for grading the cognitive state of patients for the clinician. *J Psychiatr Res* 1975, 12, 189-198.
Garzon-Aburbeh etal., a lymphotropic prodrug of L-dopa: synthesis, pharmacological properties, and pharmacokinetic behavior of 1,3-dihexadecanoyl-2-[(S)-2-amino-3-(3,4-dihydroxyphenyl)propanoyl]propane-1,2,3-triol, *J Med Chem* 1986, 29(5), 687-691.
Gelb et al., Diagnostic criteria for Parkinson disease. *Arch Neurol* 1999, 56(1), 33-9.
Gerlach and Luhdorf, the effect of L-dopa on young patients with simple schizophrenia, treated with neuroleptic drugs. *Psychopharmacologia (Berl.)* 1975, 44(1), 105-10.
Gibb et al., The relevance of the Lewy body to the pathogenesis of idiopathic Parkinson's disease. *J Neurol Neurosurg Psychiatry* 1988, 51, 745-752.
Giovannoni et al., Bradykinesia akinesia inco-ordination test (BAIN TEST): an objective computerised assessment of upper limb motor function. *J Neurol Neurosurg Psychiatry* 1999, 67, 624-629.
Hirsch et al., Animal models of Parkinson's disease in rodents induced by toxins: an update. *J Neural Transm Suppl* 2003, 65, 89-100.
Hisaka etal., Absorption of a novel prodrug of L-Dopa, L-3-(3-hydroxy-4-pivaloyloxyphenyl)alanine (NB-355): in vitro and in situ studies. Drug Metabolism and Disposition 1990, 18(5), 621-625.
Hogl etal., In creased daytime sleepiness in Parkinson's disease: a questionnaire survey, *Movement Disorders* 2003, 18(3), 319-323.
Howard et al., Intracerebral drug delivery in rats with lesion-induced memory deficits. *J. Neurosurg* 1989, 71, 105-112.
Inanaga et al., Double-blind controlled study of L-dopa therapy in schizophrenia, *Folia Psychiatr Neurol Jpn* 1975, 29(2), 123-143.
Ishikura et al., Drug delivery to the brain. DOPA prodrugs based on a ring-closure reaction to quaternary thiazolium compounds. *Int'l. J. Pharmaceutics* 1995, 116, 51-63.
Ishikura et al., Database CAS citation 1994:701312 [retrieved Nov. 23, 2009] from STN; Columbus, OH USA.
Ishikura et al., Database CAS citation 1995:365090 [retrieved Nov. 23, 2009] from STN; Columbus, OH USA.
Jankovic, Treatment of dystonia, *Lancet Neurol* 2006, 5(10), 864-872.
Jaskiw and Popli, a meta-analysis of the response to chronic L-dopa in patients with schizophrenia: therapeutic and heuristic implications, *Psychopharmacology* 2004, 171, 365-374.
Juncos et al., Levodopa methyl ester treatment of Parkinson's disease, *Neurology* 1987, 37(7), 1242-1245.

Kay and Opler, L-dopa in the treatment of negative schizophrenic symptoms: a single-subject experimental study, *Int'l J Psychiatry Med* 1985-1986, 15(3), 293-298.

Knecht et al., Levodopa: faster and better word learning in normal humans, *Ann. Neurol* 2004, 56(1), 20-26.

Kulisevsky, Role of dopamine in learning and memory: implications for the treatment of cognitive dysfunction in patients with Parkinson's disease, *Drugs Aging* 2000, 16(5), 365-379.

Langer and Peppas, Chemical and physical structure of polymers as carriers for controlled release of bioactive agents: a review. *JMS-Rev. MacromoL Chem. Phys.* 1983, C23(1), 61-126.

Langer, New Methods of Drug Delivery. *Science* 1990, 249:1527-1533.

Leong and Langer, Polymeric controlled drug delivery. *Advanced Drug Delivery Reviews* 1987, 1, 199-233.

Leppert et al., The Effects of Carbidopa Dose and Time and Route of Administration on Systemic L-Dopa Levels in Rats. *Pharmaceutical Res* 1988, 5(9), 587-591.

Levy et al., .Inhibition of Calcification of Bioprosthetic Heart Valves by Local Controlled-Release Diphosphonate. *Science* 1985, 228, 190-192.

Lu and Yu, Dimensionless presentation for drug release from a coated pure drug bead: 2. Experiment. *Int. J. Pharmaceutics* 1994, 112, 117-124.

Ludatsher, Stable remission of tardive dyskinesia by L-dopa. *J Clin Psychopharm* 1989, 9(1), 905-210.

Manson et al., An ambulatory dyskinesia monitor. *J Neurol Neurosurg Psychiatry* 2000, 68, 196-201.

Marrel et al., L-dopa esters as potential prodrugs, *Eur J Med Chem—Chim Ther* 1985, 20(5), 459-465.

Movement Disorder Society Task Force, the Unified Parkinson's Disease Rating Scale (UPDRS): status and recommendations. *Mov Disord* 2003, 18(7), 738-50.

Nutt, Response to levodopa treatment in dopa-responsive dystonia. *Arch Neurol* 2001, 58, 905-210.

O'Neill et al., LY503430: pharmacology, pharmacokinetics, and effects in rodent models of Parkinson's disease. *CNS Drug Rev.* 2005, 11(1), 77-96.

O'Suilleabhain and Dewey, Contributions of dopaminergic drugs and disease severity to daytime sleepiness in Parkinson disease. *Arch Neuro* 2002, 59(6), 986-9.

Olson et al., Gabapentin for Parkinsonism: a double-blind, placebo-controlled, crossover trial. *Am. J. Med.* 1997, 102(1), 60-6.

Ondo and Jankovic, Restless legs syndrome: clinicoetiologic correlates, *Neurology* 1996, 47(6), 1435-1441.

Orth and Tabrizi, Models of Parkinson's disease. *Mov Disord* 2003, 18(7), 729-37.

Paus et al., Sleep attacks, daytime sleepiness, and dopamine agonists in Parkinson's disease, *Movement Disorders* 2003, 18(6), 659-667.

Racette and Perlmutter, Levodopa responsive Parkinsonism in an adult with Huntington's disease. *J Neurol Neurosurg Psychiatry* 1998, 65(4), 577-579.

Rascol and Fabre, Dyskinesia: L-dopa-induced and tardive dyskinesia, *Clinical Neuropharmacology* 2001, 24(6), 313-323.

Rouhi, The Righ Stuff, *Science and Technology*, C&E News Feb. 2003, 32-35.

Sasahara et al., Dosage form design for improvement of bioavailability of levodopa II: bioavailability of marketed levodopa preparations in dogs and Parkinsonian patients. *J. Pharm. Sci.* 1980, 69(3), 261-265.

Saudek et al., a Preliminary trial of the programmable implantable medication system for insulin delivery. *N. Engl. J. Med.* 1989, 321, 574-579.

Scheidtmann etal., Effect of levodopa in combination with physiotherapy on functional motor recovery after stroke: a prospective, randomized, double-blind study, *Lancet* 2001, 358(9284), 787-790.

Schneider et al., Familial dopa-responsive cervical dystonia, *Neurology* 2006, 66(4), 599-601.

Sefton, "Implantable Pumps," *CRC Critical Reviews in Biomedical Engineering* 1987, 14(3), 201-240.

Silber, Sleep disorders, *Neurologic Clin* 2001, 19(1), 173-186.

Soares and McGrath, The treatment of tardive dyskinesia—a systematic review and meta-analysis, *Schizophr Res* 1999, 39(1), 1-16.

Tang et al., Synthesis and Characterization of Water-soluble and photostable L-dopa dendrimers, *Organic Letters* 2006, 8(2), 4421-4424.

Tolwani et al., Experimental models of Parkinson's disease: insights from many models. *Lab Anim Sci* 1999, 49(4), 363-71.

Van Blercom of al., Effects of gabapentin on the motor response to levodopa. *Clin Neuropharmacol* 2004, 27(3), 124-8.

Verma et al., Osmotically controlled oral drug delivery. *Drug Development and Industrial Pharmacy* 2000, 26(7), 695-708.

Von Scheele, Levodopa in restless legs, *Lancet* 1986, 2(8504), 426-427.

Wang et al., Preparation and intestinal absorption of L-dopa-D-phenylglycine. *J. Food and Drug Analysis* 2002, 10(2), 81-87.

Wang et al., Synthesis and pharmacological activities of a novel tripeptide mimetic dopamine prodrug. *Bioorganic & Medicinal Chemistry Letters* 1995, 5(19), 2195-2198.

International Search Report and Written Opinion mailed Nov. 3, 2005, for International Application No. PCT/US2005/019492, filed Jun. 3, 2005.

International Search Report and Written Opinion mailed Nov. 3, 2005, for International Application No. PCT/US2005/019493, filed Jun. 3, 2005.

International Search Report and Written Opinion mailed Jul. 23, 2007, for International Application No. PCT/US2006/046273, filed Dec. 4, 2006.

International Search Report and Written Opinion of the International Searching Authority mailed Apr. 15, 2008, for International Application No. PCT/US2007/026200 filed Dec. 20, 2007.

International Search Report and Written Opinion of the International Searching Authority mailed May 14, 2008 for International Application No. PCT/US2007/026271, filed Dec. 20, 2007.

International Search Report and Written Opinion of the International Searching Authority mailed May 27, 2008 for International Application No. PCT/US2007/078541, filed Sep. 14, 2007.

Notice of Allowance mailed Sep. 11, 2007, for U.S. Appl. No. 11/145,280, filed Jun. 3, 2005.

Notice of Allowance mailed Oct. 10, 2007 for U.S. Appl. No. 11/145,159 filed Jun. 3, 2005.

Notice of Allowance mailed Jan. 23, 2008 for U.S. Appl. No. 11/145,159, filed Jun. 3, 2005 (Supplemental).

Notice of Allowance mailed Oct. 15, 2008, for U.S. Appl. No. 12/008,473, filed Jan. 10, 2008.

Notice of Allowance mailed Mar. 20, 2009 for U.S. Appl. No. 11/634,354, filed Dec. 4, 2006.

Notice of Allowance mailed May 29, 2009 for U.S. Appl. No. 12/001,618, filed Dec. 11, 2007.

Notice of Allowance mailed Dec. 16, 2009, for U.S. Appl. No. 12/005,117, filed Dec. 20, 2007.

Office Action mailed Nov. 24, 2006, for U.S. Appl. No. 11/145,159 filed Jun. 3, 2005.

Office Action mailed Jan. 19, 2007, for U.S. Appl. No. 11/145,280, filed Jun. 3, 2005.

Office Action mailed Apr. 17, 2007, for U.S. Appl. No. 11/145,280, filed Jun. 3, 2005.

Office Action mailed Jun. 15, 2007 for U.S. Appl. No. 11/145,159 filed Jun. 3, 2005.

Office Action mailed Mar. 21, 2008 for U.S. Appl. No. 11/634,354, filed Dec. 4, 2006.

Office Action mailed Jun. 3, 2008 for U.S. Appl. No. 12/008,473, filed Jan. 10, 2008.

Office Action mailed Sep. 16, 2008 for U.S. Appl. No. 11/634,354, filed Dec. 4, 2006.

Office Action mailed Oct. 24, 2008 for U.S. Appl. No. 12/001,618 filed Dec. 11, 2007.

Office Action mailed Aug. 7, 2009, for U.S. Appl. No. 12/005,117, filed Dec. 20, 2007.

Office Action mailed Dec. 1, 2009 (later vacated) for U.S. Appl. No. 12/364,453, filed Feb. 2, 2009.

Office Action mailed Jan. 25, 2010, for U.S. Appl. No. 12/005,120, filed Dec. 20, 2007.

* cited by examiner

LEVODOPA DIMETHYL-SUBSTITUTED DIESTER PRODRUGS, COMPOSITIONS, AND METHODS OF USE

This application is a continuation application of U.S. application Ser. No. 12/005,117, filed Dec. 20, 2007, which issued as U.S. Pat. No. 7,709,527 and, which claims the benefit under 35 U.S.C. §119(e) of U.S. Provisional Application Serial No. 60/876,144 filed Dec. 21, 2006, and U.S. Provisional Application Serial No. 60/967,773 filed Sep. 7, 2007, each of which is incorporated by reference in its entirety.

FIELD

Disclosed herein are levodopa dimethyl-substituted diester prodrugs and pharmaceutical compositions comprising levodopa dimethyl-substituted diester prodrugs, useful for treating diseases such as Parkinson's disease.

BACKGROUND

Parkinson's disease is a disabling, progressive illness that affects one in 1,000 people and generally occurs in people over the age of 50 years. Patients with Parkinson's disease have a deficiency of the neurotransmitter dopamine in the brain as a result of nigrostriatal pathway disruption caused by degeneration of the substantia nigra. Levodopa (L-dopa or L-3,4-dihydroxyphenylalanine), an immediate precursor of dopamine, is the most commonly prescribed drug for treatment of this disease.

Following oral administration, levodopa is rapidly absorbed via an amino acid transporter present in the upper small intestine. Due to the narrow distribution of this transporter system, the window available for levodopa absorption is limited and the extent of absorption can depend on the rate at which the drug passes through the upper gastrointestinal tract.

Intestinal metabolism of levodopa is the major source of first pass loss of the drug. Approximately 35% of an administered dose of levodopa reaches the systemic circulation as intact levodopa after oral administration in patients (Sasahara, *J. Pharm. Sci* 1990, 69, 261). Once absorbed, levodopa is rapidly metabolized to dopamine by L-aromatic amino acid decarboxylase (AADC) enzymes in the peripheral tissues (e.g., intestines and liver). For this reason, levodopa is normally co-administered with a decarboxylase enzyme inhibitor such as carbidopa or benserazide. When administered with carbidopa, the plasma concentration of intact levodopa increases and thus more levodopa becomes available to be transported into the central nervous system where it is converted to dopamine. Carbidopa and benserazide do not cross the blood-brain barrier to a significant extent and therefore do not inhibit the required conversion of levodopa to dopamine in the brain.

The use of prodrugs of levodopa to improve the pharmacokinetics of levodopa has been proposed. Many of these prodrugs are simple esters of levodopa (see, e.g., Chiesi, U.S. Pat. Nos. 5,017,607 and 4,826,875; Repta, U.S. Pat. Nos. 4,873,263, 4,771,073 and 4,663,349; Bodor et al., U.S. Pat. No. 4,311,706; Konishi and Ienaga, Japanese Patent No. JP58024547; Juncos et al., *Neurology* 1987, 37, 1242; and Cooper et al., *J. Pharm. Pharmacol.* 1987, 39, 627-635). An oral formulation of levodopa methyl ester (Levomet®, CHF 1301) has been described (Chiesi Pharmaceuticals). The ethyl ester of levodopa (TV-1203) is under clinical investigation as a potential therapy for Parkinson's disease when co-administered with carbidopa (Milman et al., U.S. Pat. No. 5,607, 969). A sustained release cellulose formulation of levodopa ethyl ester in a mixture of hydroxypropylmethyl cellulose, hydroxypropyl cellulose, and a carboxyvinyl polymer has also been described (Cohen et al., U.S. Pat. No. 5,840,756). However, oral administration of this formulation to healthy adults pretreated with carbidopa produced a plasma levodopa terminal half-life of only 2 hours, comparable to that of Sinemet® CR.

A pivaloyl ester of levodopa (NB-355) has been described (Tsuchiya and Hayashi, European Patent No. 0 309 827). Following oral administration of NB-355, a rapid increase in the plasma concentration or in the elimination of levodopa was not observed and the duration of circulating levodopa was prolonged, although plasma concentrations of levodopa were low. The potential for using ester prodrugs of levodopa to enhance rectal absorption of the drug has also been described (Repta, U.S. Pat. Nos. 4,663,349, 4,771,073, and 4,873,263). Notably, the absorption of simple alkyl esters of levodopa has been shown to be greater following rectal absorption than following oral dosing (Fix, et al., *Pharm. Res.* 1989, 6, 501-5; and Fix, et al., *Pharm. Res.* 1990, 4, 384-7). This effect is attributed to the decreased abundance of esterases in the large intestine relative to the small intestine. Therefore, selective delivery of a prodrug of levodopa to the large intestine in a sustained release formulation might be expected to provide a greater oral bioavailability and a prolonged systemic exposure to the drug. A series of glycolic acid ester containing prodrugs of levodopa has been described (Wermuth, U.S. Pat. No. 4,134,991). Lipid conjugates of levodopa to facilitate the entry of levodopa into cells and tissues have also been described (Yatvin, U.S. Pat. No. 5,827,819). Glyercol derivatives of levodopa are described by Dumont, International Application Publication No. WO 86/04579. Catechol protected levodopa derivatives intended to provide sustained clinically effective blood concentrations of levodopa are disclosed in Tsuchiya et al., U.S. Pat. No. 4,966,915.

Thus, the development of levodopa prodrugs that can be efficiently absorbed throughout the gastrointestinal tract, including the colon, and reduce first-pass metabolism of levodopa is highly desirable.

The human gastrointestinal tract includes the small intestine and the large intestine. The human small intestine is a convoluted tube about twenty feet in length between the stomach and large intestine. The small intestine is subdivided into the duodenum, the jejunum, and the ileum. The large intestine is about 5 feet in length and runs from the ileum to the anus. The large intestine is divided into the caecum, colon, and the rectum. The colon is divided into four parts including the ascending, traverse, descending, and the sigmoid flexure. In general, an orally ingested compound resides about 1 to 6 hours in the stomach, about 2 to 7 hours in the small intestine, and about 8 to 18 hours in the colon. Thus, the greatest period of time for sustained release of a compound occurs when the compound is passing through the colon.

Certain active transporter proteins are known to be expressed throughout the gastrointestinal tract. An active transporter refers to a membrane-bound protein that recognizes a substrate and affects the entry of the substrate into or exit from a cell by carrier-mediated transport or receptor-mediated transport. Active transport includes movement of molecules across cellular membranes that is directly or indirectly dependent on an energy mediated process, such as for example by a process driven by ATP hydrolysis, or by an ion gradient, which occurs by facilitated diffusion mediated by interaction with specific transporter proteins through a modulated solute channel. Examples of solute mediated transporters include organic cation transporters such as OCTN1 and OCTN2, which are expressed in the epithelial cells lining a human colon as well as in the small intestine.

More recently, levodopa prodrugs designed to be absorbed in both the small and large intestines have been described in Xiang et al., U.S. Application Publication Nos. 2005/0282891 and 2006/0020028, each of which is incorporated by reference herein in its entirety. These levodopa prodrugs can achieve a bioavailability of levodopa that is at least two times greater than the bioavailability of levodopa when intracolonically administered on an equivalent molar basis. The mesylate salt of one of these prodrugs, (2R)-2-phenylcarbonyloxypropyl (2S)-2-amino-3-(3,4-dihydroxyphenyl)propanoate mesylate, and crystalline forms thereof are described in Xiang et al., U.S. Application Publication No. 2007/0225366. The prodrugs described by Xiang et al. can be efficaciously incorporated into sustained release formulations including osmotic delivery devices to provide sustained systemic exposure to levodopa upon oral administration to a patient.

SUMMARY

Accordingly, a need exists for levodopa prodrugs and crystalline forms thereof exhibiting physicochemical properties that may be used advantageously in pharmaceutical processing and pharmaceutical compositions, and that are also sufficiently labile under physiological conditions to provide therapeutically effective plasma concentrations of levodopa, particularly when the levodopa prodrug is orally administered.

In a first aspect, compounds are provided having Formula (I):

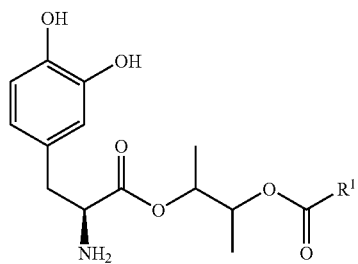

stereoisomers thereof, pharmaceutically acceptable salts of any of the foregoing, or pharmaceutically acceptable solvates of any of the foregoing, wherein:

$R^1$ is chosen from $C_{1-8}$ alkyl, substituted $C_{1-8}$ alkyl, $C_{1-8}$ alkoxy, substituted $C_{1-8}$ alkoxy, $C_{3-7}$ cycloalkyl, substituted $C_{3-7}$ cycloalkyl, $C_{3-7}$ cycloalkoxy, substituted $C_{3-7}$ cycloalkoxy, phenyl, and substituted phenyl;

wherein each substituent group is independently chosen from halogen, —OH, —COOH, —CN, —CF$_3$, =O, —NO$_2$, $C_{1-3}$ alkoxy, $C_{1-3}$ alkyl, and —NR$^2{}_2$ wherein each $R^2$ is independently chosen from hydrogen and $C_{1-3}$ alkyl.

In a second aspect, pharmaceutical compositions are provided comprising at least one pharmaceutically acceptable vehicle and a therapeutically effective amount of at least one compound of Formula (I) for treating a disease in a patient.

In a third aspect, methods of treating a disease in a patient are provided comprising administering to a patient in need of such treatment a pharmaceutical composition comprising at least one compound of Formula (I).

BRIEF DESCRIPTION OF THE DRAWINGS

Those skilled in the art will understand that the drawings, described herein, are for illustration purposes only. The drawings are not intended to limit the scope of the present disclosure.

DETAILED DESCRIPTION

Definitions

Figure 1:
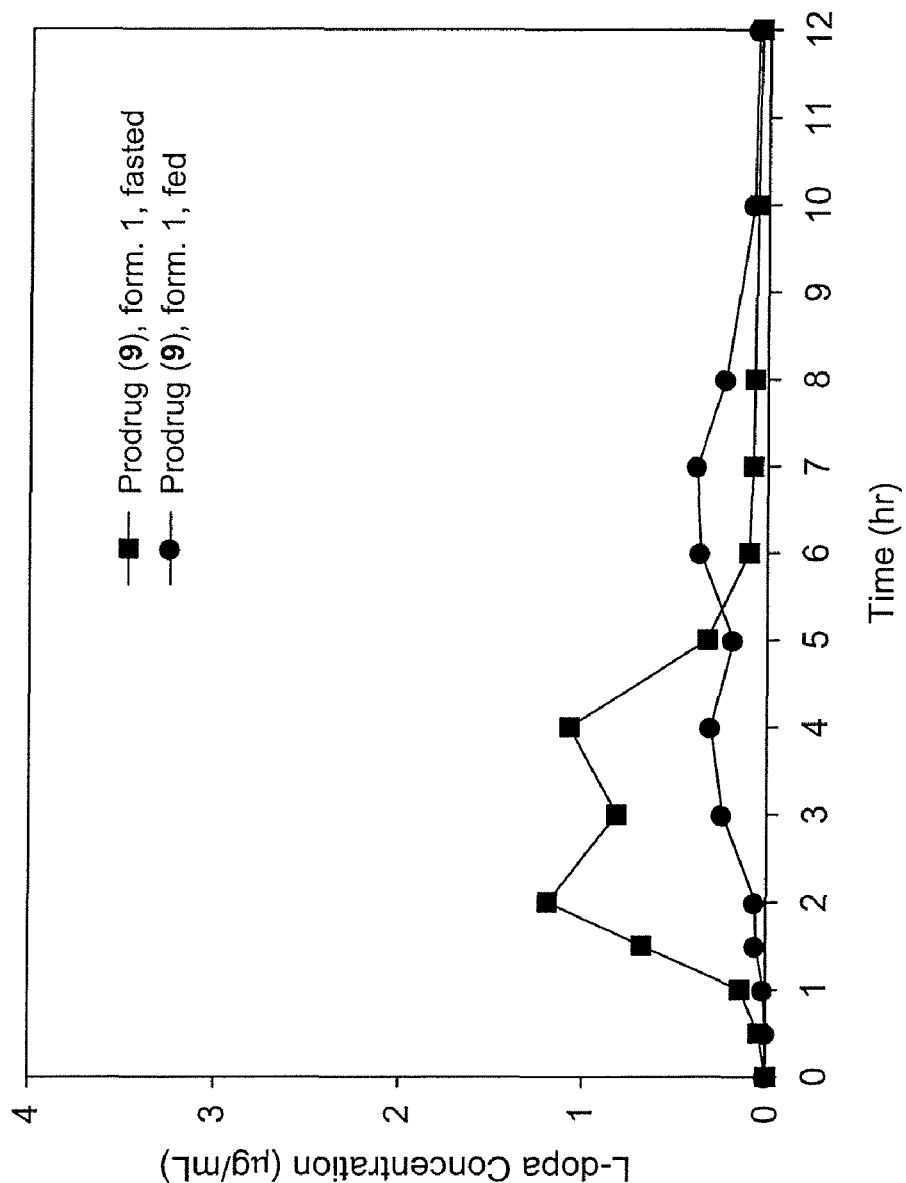
FIG. 1 shows levodopa levels in plasma following oral administration of tablet formulations comprising levodopa prodrug (9) to fed and fasted monkeys with 25 mg carbidopa co-administered i.p.

A dash ("-") that is not between two letters or symbols is used to indicate a point of attachment for a substituent. For example, —CONH$_2$ is attached through the carbon atom.

"Alkyl" by itself or as part of another substituent refers to a saturated or unsaturated, branched or straight-chain, monovalent hydrocarbon radical derived by the removal of one hydrogen atom from a single carbon atom of a parent alkane, alkene, or alkyne. Examples of alkyl groups include, but are not limited to, methyl; ethyls such as ethanyl, ethenyl, and ethynyl; propyls such as propan-1-yl, propan-2-yl, prop-1-en-1-yl, prop-1-en-2-yl, prop-2-en-1-yl (allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds, and groups having mixtures of single, double, and triple carbon-carbon bonds. Where a specific level of saturation is intended, the terms "alkanyl," "alkenyl," and "alkynyl" are used. In certain embodiments, an alkyl group can have from 1 to 20 carbon atoms, in certain embodiments, from 1 to 10 carbon atoms, and in certain embodiments, from 1 to 8, from 1 to 5 carbon atoms, or from 1 to 3 carbon atoms.

"Alkoxy" by itself or as part of another substituent refers to a radical —OR$^{31}$ where R$^{31}$ is chosen from alkyl, cycloalkyl, cycloalkylalkyl, aryl, and arylalkyl, which can be substituted, as defined herein. In some embodiments, alkoxy groups have from 1 to 8 carbons, from 1 to 5 carbon atoms, or from 1 to 3 carbon atoms. Examples of alkoxy groups include, but are not limited to, methoxy, ethoxy, propoxy, butoxy, cyclohexyloxy, and the like.

"Aryl" by itself or as part of another substituent refers to a monovalent aromatic hydrocarbon radical derived by the removal of one hydrogen atom from a single carbon atom of a parent aromatic ring system. Aryl encompasses 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocyclic aromatic ring, cycloalkyl ring, or heterocycloalkyl ring. For example, aryl includes 5- and 6-membered carbocyclic aromatic rings fused to a 5- to 7-membered heterocycloalkyl ring containing one or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Examples of aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In certain embodiments, an aryl group can have from 5 to 20 carbon atoms, and in certain embodiments, from 5 to 12 carbon atoms. Aryl, however, does not encompass or overlap in any way with heteroaryl, separately defined herein. Hence, a multiple ring system in which one or more carbocyclic aromatic rings is fused to a heterocycloalkyl aromatic ring, is heteroaryl, not aryl, as defined herein. In certain embodiments, an aryl group is phenyl.

"AUC" is the area under a curve representing the concentration of a compound or metabolite thereof in a biological fluid in a patient as a function of time following administration of the compound to the patient. In certain embodiments, the compound can be a prodrug and the metabolite can be a drug. Examples of biological fluids include blood and plasma. The AUC may be determined by measuring the concentration of a compound or metabolite thereof in a biological fluid such as the plasma or blood using methods such as liquid chromatography-tandem mass spectrometry (LC/MS/MS), at various time intervals, and calculating the area under the plasma concentration-versus-time curve. Suitable methods for calculating the AUC from a drug concentration-versus-time curve are well known in the art. As relevant to the disclosure herein, an AUC for levodopa may be determined by measuring the concentration of levodopa in the plasma or blood of a patient following oral administration of a dosage form comprising a compound of Formula (I) or crystalline form thereof.

"Bioavailability" refers to the amount of a drug that reaches the systemic circulation of a patient following administration of the drug or prodrug thereof to the patient and may be determined by evaluating, for example, the plasma or blood concentration-versus-time profile for a drug. Parameters useful in characterizing a plasma or blood concentration-versus-time curve include the area under the curve (AUC), the time to maximum concentration ($T_{max}$), and the maximum drug concentration ($C_{max}$), where $C_{max}$ is the maximum concentration of a drug in the plasma or blood of a patient following administration of a dose of the drug or prodrug thereof to the patient, and $T_{max}$ is the time to the maximum concentration ($C_{max}$) of a drug in the plasma or blood of a patient following administration of a dose of the drug or prodrug thereof to the patient.

"Compounds" refers to compounds encompassed by structural Formula (I) disclosed herein and includes any specific compounds within these formulae whose structure is disclosed herein. Compounds may be identified either by their chemical structure and/or chemical name. When the chemical structure and chemical name conflict, the chemical structure is determinative of the identity of the compound.

The compounds described herein may contain one or more chiral centers and/or double bonds and therefore may exist as stereoisomers such as double-bond isomers (i.e., geometric isomers), enantiomers, or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan.

Compounds of Formula (I) include, but are not limited to, optical isomers of compounds of Formula (I), racemates thereof, and other combinations thereof. In such embodiments, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, compounds of Formula (I) include Z- and E-forms (e.g., cis- and trans-forms) of compounds with double bonds. In embodiments in which compounds of Formula (I) exist in various tautomeric forms, compounds of the present disclosure include all tautomeric forms of the compound.

Compounds of Formula (I) may also exist in several tautomeric forms including the enol form, the keto form, and mixtures thereof. Accordingly, the chemical structures depicted herein encompass all possible tautomeric forms of the illustrated compounds. The compounds of Formula (I) also include isotopically labeled compounds where one or more atoms have an atomic mass different from the atomic mass conventionally found in nature. Examples of isotopes that may be incorporated into the compounds disclosed herein include, but are not limited to, $^2H$, $^3H$, $^{11}C$, $^{13}C$, $^{14}C$, $^{15}N$, $^{18}O$, $^{17}O$, etc. Compounds may exist in unsolvated foams as well as solvated forms, including hydrated forms and as N-oxides. In general, compounds may be hydrated, solvated, or N-oxides. Certain compounds may exist in single or multiple crystalline or amorphous forms. In general, all physical forms are equivalent for the uses contemplated herein and are intended to be within the scope of the present disclosure.

Further, when partial structures of the compounds are illustrated, an asterisk (*) indicates the point of attachment of the partial structure to the rest of the molecule.

"Cycloalkyl" by itself or as part of another substituent refers to a partially saturated or unsaturated cyclic alkyl radical. Where a specific level of saturation is intended, the nomenclature "cycloalkanyl" or "cycloalkenyl" is used. Examples of cycloalkyl groups include, but are not limited to, groups derived from cyclopropane, cyclobutane, cyclopentane, cyclohexane, and the like. In certain embodiments, a cycloalkyl group is $C_{3-15}$ cycloalkyl, and in certain embodiments, $C_{5-12}$ cycloalkyl, or $C_{3-7}$ cycloalkyl. In certain embodiments, a cycloalkyl is cyclohexyl.

"Cycloalkoxy" by itself or as part of another substituent refers to a partially saturated or unsaturated cyclic alkoxy radical. Examples of cycloalkoxy groups include, but are not limited to, groups derived from cyclopropoxy, cyclobutoxy, cyclopentyloxy, cyclohexyloxy, and the like. In certain embodiments, a cycloalkoxy group is $C_{3-15}$ cycloalkyl, and in certain embodiments, $C_{5-12}$ cycloalkyl, or $C_{3-7}$ cycloalkoxy. In certain embodiments, a cycloalkoxy is cyclohexyloxy.

"Dimethyl-substituted" refers to the two methyl groups independently bonded to the carbon atoms between the two carboxylic acid ester groups of compounds of Formula (I).

"Disease" refers to a disease, disorder, condition, symptom, or indication.

"Diastereomeric purity" refers to the percent of one diastereomer of a compound relative to all other diastereomers of the compound in a composition containing more than one diastereomer of the compound. For example, a composition has a diastereomeric purity of 97% of the (1S,2S)-stereoisomer of a compound of Formula (I) when about 97% of the compound of Formula (I) in the composition is the (1S,2S)-stereoisomer and about 3% of the compound of Formula (I) in the composition comprises one or more of the other stereoisomers. In certain embodiments, the diastereomeric purity is, for example, greater than or at least 90%, at least about 91%, at least about 92%, at least about 93%, at least about 94%, at least about 95%, at least about 96%, at least about 97%, at least about 98%, or at least about 99%.

"Halogen" refers to a fluoro, chloro, bromo, or iodo group.

"Parent aromatic ring system" refers to an unsaturated cyclic or polycyclic ring system having a conjugated $\pi$ (pi) electron system. Included within the definition of "parent aromatic ring system" are fused ring systems in which one or more of the rings are aromatic and one or more of the rings are saturated or unsaturated, such as, for example, fluorene, indane, indene, phenalene, etc. Examples of parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octacene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like.

"Parkinson's disease" is a clinical syndrome comprising bradykinesia (slowness and poverty of movement), muscular rigidity, resting tremor (which usually abates during voluntary movement), and an impairment of postural balance leading to disturbance of gait and falling. Other symptoms include gait and posture disturbances such as shuffling, decreased arm swing, turning "en bloc," stooped, forward-reflexed posture, festination, gait freezing and dystonia; speech and swallowing disturbances such as hypophonia, festinating speech, drooling, non-motor causes of speech/language disturbance in both expressive and receptive language, and dysphagia; as well as fatigue, masked facies, micrographia, impaired fine motor dexterity and coordination, impaired gross motor coordination, and poverty of movement. Non-motor mood disturbances associated with Parkinson's disease include mood disturbances such as depression; cognitive disturbances such as slowed reaction time, executive dysfunction, dementia, memory loss, and medication effects; sleep disturbances such as excessive daytime somnolence, insomnia, and disturbances in REM sleep; sensation disturbances such as impair visual perception, dizziness and fainting, impaired proprioception, reduction or loss of sense of smell, and pain; and autonomic disturbances such as oily skin and seborrheic dermatitis, urinary incontinence, constipation and gastric dysmotility, altered sexual function, and weight loss.

The Unified Parkinson's disease Rating scale is the primary clinical tool used for the diagnosis of Parkinson's disease (see e.g., Gelb et al., *Arch Neurol* 1999, 56(1), 33-9; and Goetz, *Mov Disord* 2003, 18(7), 738-50).

"Pharmaceutically acceptable salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinct acid, malice acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; and (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine, and the like.

"Patient" includes mammals, such as for example, humans.

"Pharmaceutical composition" refers to a composition comprising at least one compound provided by the present disclosure and at least one pharmaceutically acceptable vehicle with which the compound is administered to a patient.

"Pharmaceutically acceptable" refers to approved or approvable by a regulatory agency of a federal or a state government, listed in the U.S. Pharmacopoeia, or listed in other generally recognized pharmacopoeia for use in mammals, including humans.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which a compound of the present disclosure can be administered to a patient and which does not destroy the pharmacological activity thereof and which is nontoxic when administered in doses sufficient to provide a therapeutically effective amount of the compound.

"Prodrug" refers to a derivative of a drug molecule that requires a transformation within the body to release the active drug. Prodrugs are frequently, although not necessarily, pharmacologically inactive until converted to the parent drug. For example, a compound of Formula (I) is a prodrug of the drug, levodopa, or an active metabolite of the compound of Formula (I), which exhibits therapeutic efficacy.

"Promoiety" refers to a group bonded to a drug, typically to a functional group of the drug, via bond(s) that are cleavable under specified conditions of use. The bond(s) between the drug and promoiety may be cleaved by enzymatic or non-enzymatic means. Under the conditions of use, for example following administration to a patient, the bond(s) between the drug and promoiety may be cleaved to release the parent drug. The cleavage of the promoiety may proceed spontaneously, such as via a hydrolysis reaction, or may be catalyzed or induced by another agent, such as by an enzyme, by light, by acid, or by a change of or exposure to a physical or environmental parameter, such as a change of temperature, pH, etc. The agent may be endogenous to the conditions of use, such as an enzyme present in the systemic circulation to which the prodrug is administered or the acidic conditions of the stomach or the agent may be supplied exogenously.

"Protecting group" refers to a grouping of atoms that when attached to a reactive functional group in a molecule masks, reduces or prevents reactivity of the functional group. Examples of protecting groups can be found for example, in Wuts and Greene, "Protective Groups in Organic Synthesis,"

John Wiley & Sons, 4th ed. 2006; Harrison et al., "Compendium of Organic Synthetic Methods," Vols. 1-11, John Wiley & Sons 1971-2003; Larock "Comprehensive Organic Transformations," John Wiley & Sons, 2nd ed. 2000; and Paquette, "Encyclopedia of Reagents for Organic Synthesis," John Wiley & Sons, 11th ed. 2003. Examples of amino protecting groups include, but are not limited to, formyl, acetyl, trifluoroacetyl, benzyl, benzyloxycarbonyl (Cbz), tert-butoxycarbonyl (Boc), trimethylsilyl (TMS), 2-(trimethylsilyl)ethanesulfonyl (SES), trityl and substituted trityl groups, allyloxycarbonyl, 9-fluorenylmethoxycarbonyl (FMOC), 6-nitroveratryloxycarbonyl (NVOC), and the like. Examples of hydroxy protecting groups include, but are not limited to, those where the hydroxy group is either acylated or alkylated such as benzyl, and trityl ethers as well as alkyl ethers, tetrahydropyranyl ethers, trialkylsilyl ethers, and allyl ethers.

"Solvate" refers to a molecular complex of a compound with one or more solvent molecules in a stoichiometric or non-stoichiometric amount. Such solvent molecules are those commonly used in the pharmaceutical art, which are known to be innocuous to a recipient, e.g., water, ethanol, and the like. A molecular complex of a compound or moiety of a compound and a solvent can be stabilized by non-covalent intra-molecular forces such as, for example, electrostatic forces, van der Waals forces, or hydrogen bonds. The term "hydrate" refers to a complex where the one or more solvent molecules are water including monohydrates and hemi-hydrates.

"Substantially one diastereomer" refers to a compound containing two or more stereogenic centers such that the diastereomeric excess (d.e.) of the compound is greater than or about at least 90%. In certain embodiments, the d.e. is, for example, greater than or at least about 91%, about 92%, about 93%, about 94%, about 95%, about 96%, about 97%, about 98%, or about 99%.

"Substituted" refers to a group in which one or more hydrogen atoms are independently replaced with the same or different substituent(s). In certain embodiments, each substituent group can independently be selected from halogen, —$NO_2$, —OH, =O, —COOH, —$NH_2$, —CN, —$CF_3$, —$OCF_3$, $C_{1-8}$ alkyl, substituted $C_{1-8}$ alkyl, $C_{1-8}$ alkoxy, and substituted $C_{1-8}$ alkoxy In certain embodiments, each substituent group can independently be selected from halogen, —OH, —COOH, —CN, —$CF_3$, =O, —$NO_2$, $C_{1-3}$ alkoxy, $C_{1-3}$ alkyl, and —$NR^{10}_2$ wherein each $R^{10}$ is independently chosen from hydrogen and $C_{1-3}$ alkyl.

"Sustained release" refers to release of a therapeutic or preventive amount of a drug or an active metabolite thereof over a period of time that is longer than that of a conventional formulation of the drug. For oral formulations, the term "sustained release" typically means release of the drug within the gastrointestinal tract lumen over a time period ranging from about 2 to about 30 hours, and in certain embodiments, over a time period ranging from about 4 to about 24 hours. Sustained release formulations achieve therapeutically effective concentrations of the drug in the systemic circulation over a prolonged period of time relative to that achieved by oral administration of a conventional formulation of the drug. "Delayed release" refers to release of the drug or an active metabolite thereof into the gastrointestinal lumen after a delayed time period, for example a delay of about 1 to about 12 hours, relative to that achieved by oral administration of a conventional formulation of the drug.

"Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, and to inhibiting at least one physical parameter which may or may not be discernible to the patient. In certain embodiments, "treating" or "treatment" refers to delaying the onset of the disease or disorder or at least one or more symptoms thereof in a patient which may be exposed to or predisposed to a disease or disorder even though that patient does not yet experience or display symptoms of the disease or disorder. "Therapeutically effective amount" refers to the amount of a compound that, when administered to a subject for treating a disease or disorder, or at least one of the clinical symptoms of a disease or disorder, is sufficient to affect such treatment of the disease, disorder, or symptom. The "therapeutically effective amount" can vary depending, for example, on the compound, the disease, disorder, and/or symptoms of the disease or disorder, severity of the disease, disorder, and/or symptoms of the disease or disorder, the age, weight, and/or health of the patient to be treated, and the judgment of the prescribing physician. An appropriate amount in any given instance can be readily ascertained by those skilled in the art or capable of determination by routine experimentation.

"Therapeutically effective dose" refers to a dose that provides effective treatment of a disease or disorder in a patient. A therapeutically effective dose can vary from compound to compound, and from patient to patient, and can depend upon factors such as the condition of the patient and the route of delivery. A therapeutically effective dose can be determined in accordance with routine pharmacological procedures known to those skilled in the art.

Compounds

In certain embodiments, a compound of the present disclosure is a compound of Formula (I):

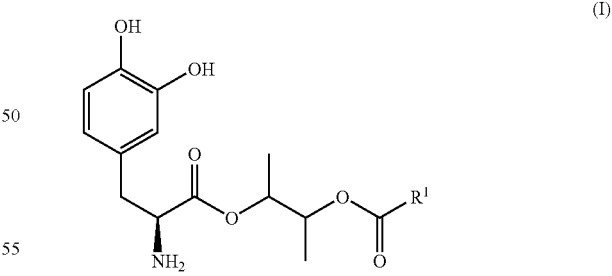

(I)

stereoisomers thereof, pharmaceutically acceptable salts of any of the foregoing, or pharmaceutically acceptable solvates of any of the foregoing, wherein:
$R^1$ is chosen from $C_{1-8}$ alkyl, substituted $C_{1-8}$ alkyl, $C_{1-8}$ alkoxy, substituted $C_{1-8}$ alkoxy, $C_{3-7}$ cycloalkyl, substituted $C_{3-7}$ cycloalkyl, $C_{3-7}$ cycloalkoxy, substituted $C_{3-7}$ cycloalkoxy, $C_{6-12}$ aryl, substituted $C_{6-12}$ aryl, $C_{6-12}$ aryloxy, and substituted $C_{6-12}$ aryloxy; and
each substituent group is independently chosen from halogen, —OH, —COOH, —CN, —$CF_3$, =O, —$NO_2$, $C_{1-3}$ alkoxy, $C_{1-3}$ alkyl, and $-NR^2_2$ wherein each $R^2$ is independently chosen from hydrogen and $C_{1-3}$ alkyl.

In certain embodiments of a compound of Formula (I), $R^1$ is chosen from $C_{1-5}$ alkyl, $C_{1-5}$ alkoxy, $C_{6-12}$ aryl, $C_{6-12}$ aryloxy, $C_{3-7}$ cycloalkyl, and $C_{3-7}$ cycloalkoxy.

In certain embodiments of a compound of Formula (I), the compound is chosen from:

(1R,2R)-2-acetyloxy-1-methylpropyl (2S)-2-amino-3-(3,4-dihydroxyphenyl)propanoate;
(1R,2R)-1-methyl-2-propanoyloxypropyl (2S)-2-amino-3-(3,4-dihydroxyphenyl)propanoate;
(1R,2R)-1-methyl-2-(2-methylpropanoyloxy)propyl (2S)-2-amino-3-(3,4-dihydroxyphenyl)propanoate;
(1R,2R)-2-(2,2-dimethylpropanoyloxy)-1-methylpropyl (2S)-2-amino-3-(3,4-dihydroxyphenyl)propanoate;
(1R,2R)-1-methyl-2-propylcarbonyloxypropyl (2S)-2-amino-3-(3,4-dihydroxyphenyl)propanoate;
(1R,2R)-1-methyl-2-(1-methylpropylcarbonyloxy)propyl (2S)-2-amino-3-(3,4-dihydroxyphenyl)propanoate;
(1R,2R)-1-methyl-2-(2-methylpropylcarbonyloxy)propyl (2S)-2-amino-3-(3,4-dihydroxyphenyl)propanoate;
(1R,2R)-2-(1,1-dimethylpropylcarbonyloxy)-1-methylpropyl (2S)-2-amino-3-(3,4-dihydroxyphenyl)propanoate;
(1R,2R)-2-(1,2-dimethylpropylcarbonyloxy)-1-methylpropyl (2S)-2-amino-3-(3,4-dihydroxyphenyl)propanoate;
(1R,2R)-2-(2,2-dimethylpropylcarbonyloxy)-1-methylpropyl (2S)-2-amino-3-(3,4-dihydroxyphenyl)propanoate;
(1R,2R)-2-butylcarbonyloxy-1-methylpropyl (2S)-2-amino-3-(3,4-dihydroxyphenyl)propanoate;
(1R,2R)-2-(1-methylbutylcarbonyloxy)-1-methylpropyl (2S)-2-amino-3-(3,4-dihydroxyphenyl)propanoate;
(1R,2R)-2-(2-methylbutylcarbonyloxy)-1-methylpropyl (2S)-2-amino-3-(3,4-dihydroxyphenyl)propanoate;
(1R,2R)-2-(3-methylbutylcarbonyloxy)-1-methylpropyl (2S)-2-amino-3-(3,4-dihydroxyphenyl)propanoate;
(1R,2R)-2-hexyl-carbonyloxy-1-methylpropyl (2S)-2-amino-3-(3,4-dihydroxyphenyl)propanoate;
(1R,2R)-2-cyclopropylcarbonyloxy-1-methylpropyl (2S)-2-amino-3-(3,4-dihydroxyphenyl)propanoate;
(1R,2R)-2-cyclobutylcarbonyloxy-1-methylpropyl (2S)-2-amino-3-(3,4-dihydroxyphenyl)propanoate;
(1R,2R)-2-cyclopentylcarbonyloxy-1-methylpropyl (2S)-2-amino-3-(3,4-dihydroxyphenyl)propanoate;
(1R,2R)-2-cyclohexylcarbonyloxy-1-methylpropyl (2S)-2-amino-3-(3,4-dihydroxyphenyl)propanoate;
(1R,2R)-2-cycloheptylcarbonyloxy-1-methylpropyl (2S)-2-amino-3-(3,4-dihydroxyphenyl)propanoate;
(1R,2R)-2-phenylcarbonyloxy-1-methylpropyl (2S)-2-amino-3-(3,4-dihydroxyphenyl)propanoate;
(1R,2R)-2-methoxycarbonyloxy-1-methylpropyl (2S)-2-amino-3-(3,4-dihydroxyphenyl)propanoate;
(1R,2R)-2-ethoxycarbonyloxy-1-methylpropyl (2S)-2-amino-3-(3,4-dihydroxyphenyl)propanoate;
(1R,2R)-2-(isoproxycarbonyloxy)-1-methylpropyl (2S)-2-amino-3-(3,4-dihydroxyphenyl)propanoate;
(1R,2R)-2-(tert-butoxycarbonyloxy)-1-methylpropyl (2S)-2-amino-3-(3,4-dihydroxyphenyl)propanoate;
(1R,2R)-1-methyl-2-propoxycarbonyloxypropyl (2S)-2-amino-3-(3,4-dihydroxyphenyl)propanoate;
(1R,2R)-1-methyl-2-(1-methylpropoxycarbonyloxy)propyl (2S)-2-amino-3-(3,4-dihydroxyphenyl)propanoate;
(1R,2R)-1-methyl-2-(2-methylpropoxycarbonyloxy)propyl (2S)-2-amino-3-(3,4-dihydroxyphenyl)propanoate;
(1R,2R)-2-(1,1-dimethylpropoxycarbonyloxy)-1-methylpropyl (2S)-2-amino-3-(3,4-dihydroxyphenyl)propanoate;
(1R,2R)-2-(1,2-dimethylpropoxycarbonyloxy)-1-methylpropyl (2S)-2-amino-3-(3,4-dihydroxyphenyl)propanoate;
(1R,2R)-2-(2,2-dimethylpropoxycarbonyloxy)-1-methylpropyl (2S)-2-amino-3-(3,4-dihydroxyphenyl)propanoate;
(1R,2R)-2-butoxycarbonyloxy-1-methylpropyl (2S)-2-amino-3-(3,4-dihydroxyphenyl)propanoate;
(1R,2R)-1-methyl-2-(1-methylbutoxycarbonyloxy)propyl (2S)-2-amino-3-(3,4-dihydroxyphenyl)propanoate;
(1R,2R)-1-methyl-2-(2-methylbutoxycarbonyloxy)propyl (2S)-2-amino-3-(3,4-dihydroxyphenyl)propanoate;
(1R,2R)-1-methyl-2-(3-methylbutoxycarbonyloxy)propyl (2S)-2-amino-3-(3,4-dihydroxyphenyl)propanoate;
(1R,2R)-1-methyl-2-pentyloxycarbonyloxypropyl (2S)-2-amino-3-(3,4-dihydroxyphenyl)propanoate;
(1R,2R)-2-cyclopropoxycarbonyloxy-1-methylpropyl (2S)-2-amino-3-(3,4-dihydroxyphenyl)propanoate;
(1R,2R)-2-cyclobutoxycarbonyloxy-1-methylpropyl (2S)-2-amino-3-(3,4-dihydroxyphenyl)propanoate;
(1R,2R)-2-cyclopentyloxycarbonyloxy-1-methylpropyl (2S)-2-amino-3-(3,4-dihydroxyphenyl)propanoate;
(1R,2R)-2-cyclohexyloxycarbonyloxy-1-methylpropyl (2S)-2-amino-3-(3,4-dihydroxyphenyl)propanoate;
(1R,2R)-2-cycloheptyloxycarbonyloxy-1-methylpropyl (2S)-2-amino-3-(3,4-dihydroxyphenyl)propanoate;
(1R,2R)-1-methyl-2-phenyloxycarbonyloxypropyl (2S)-2-amino-3-(3,4-dihydroxyphenyl)propanoate;
pharmaceutically acceptable salts of any of the foregoing, and pharmaceutically acceptable solvates of any of the foregoing.

In certain embodiments of a compound of Formula (I), the compound is chosen from:

(1S,2R)-2-acetyloxy-1-methylpropyl (2S)-2-amino-3-(3,4-dihydroxyphenyl)propanoate;
(1S,2R)-1-methyl-2-propanoyloxypropyl (2S)-2-amino-3-(3,4-dihydroxyphenyl)propanoate;
(1S,2R)-1-methyl-2-(2-methylpropanoyloxy)propyl (2S)-2-amino-3-(3,4-dihydroxyphenyl)propanoate;
(1S,2R)-2-(2,2-dimethylpropanoyloxy)-1-methylpropyl (2S)-2-amino-3-(3,4-dihydroxyphenyl)propanoate;
(1S,2R)-1-methyl-2-propylcarbonyloxypropyl (2S)-2-amino-3-(3,4-dihydroxyphenyl)propanoate;
(1S,2R)-1-methyl-2-(1-methylpropylcarbonyloxy)propyl (2S)-2-amino-3-(3,4-dihydroxyphenyl)propanoate;
(1S,2R)-1-methyl-2-(2-methylpropylcarbonyloxy)propyl (2S)-2-amino-3-(3,4-dihydroxyphenyl)propanoate;
(1S,2R)-2-(1,1-dimethylpropylcarbonyloxy)-1-methylpropyl (2S)-2-amino-3-(3,4-dihydroxyphenyl)propanoate;
(1S,2R)-2-(1,2-dimethylpropylcarbonyloxy)-1-methylpropyl (2S)-2-amino-3-(3,4-dihydroxyphenyl)propanoate;
(1S,2R)-2-(2,2-dimethylpropylcarbonyloxy)-1-methylpropyl (2S)-2-amino-3-(3,4-dihydroxyphenyl)propanoate;
(1S,2R)-2-butylcarbonyloxy-1-methylpropyl (2S)-2-amino-3-(3,4-dihydroxyphenyl)propanoate;
(1S,2R)-2-(1-methylbutylcarbonyloxy)-1-methylpropyl (2S)-2-amino-3-(3,4-dihydroxyphenyl)propanoate;
(1S,2R)-2-(2-methylbutylcarbonyloxy)-1-methylpropyl (2S)-2-amino-3-(3,4-dihydroxyphenyl)propanoate;
(1S,2R)-2-(3-methylbutylcarbonyloxy)-1-methylpropyl (2S)-2-amino-3-(3,4-dihydroxyphenyl)propanoate;
(1S,2R)-2-hexylcarbonyloxy-1-methylpropyl (2S)-2-amino-3-(3,4-dihydroxyphenyl)propanoate;
(1S,2R)-2-cyclopropylcarbonyloxy-1-methylpropyl (2S)-2-amino-3-(3,4-dihydroxyphenyl)propanoate;
(1S,2R)-2-cyclobutylcarbonyloxy-1-methylpropyl (2S)-2-amino-3-(3,4-dihydroxyphenyl)propanoate;

(1S,2R)-2-cyclopentylcarbonyloxy-1-methylpropyl (2S)-2-amino-3-(3,4-dihydroxyphenyl)propanoate;

(1S,2R)-2-cyclohexylcarbonyloxy-1-methylpropyl (2S)-2-amino-3-(3,4-dihydroxyphenyl)propanoate;

(1S,2R)-2-cycloheptylcarbonyloxy-1-methylpropyl (2S)-2-amino-3-(3,4-dihydroxyphenyl)propanoate;

(1S,2R)-2-phenylcarbonyloxy-1-methylpropyl (2S)-2-amino-3-(3,4-dihydroxyphenyl)propanoate;

(1S,2R)-2-methoxycarbonyloxy-1-methylpropyl (2S)-2-amino-3-(3,4-dihydroxyphenyl)propanoate;

(1S,2R)-2-ethoxycarbonyloxy-1-methylpropyl (2S)-2-amino-3-(3,4-dihydroxyphenyl)propanoate;

(1S,2R)-2-(isoproxycarbonyloxy)-1-methylpropyl (2S)-2-amino-3-(3,4-dihydroxyphenyl)propanoate;

(1S,2R)-2-(tert-butoxycarbonyloxy)-1-methylpropyl (2S)-2-amino-3-(3,4-dihydroxyphenyl)propanoate;

(1S,2R)-1-methyl-2-propoxycarbonyloxypropyl (2S)-2-amino-3-(3,4-dihydroxyphenyl)propanoate;

(1S,2R)-1-methyl-2-(1-methylpropoxycarbonyloxy)propyl (2S)-2-amino-3-(3,4-dihydroxyphenyl)propanoate;

(1S,2R)-1-methyl-2-(2-methylpropoxycarbonyloxy)propyl (2S)-2-amino-3-(3,4-dihydroxyphenyl)propanoate;

(1S,2R)-2-(1,1-dimethylpropoxycarbonyloxy)-1-methylpropyl (2S)-2-amino-3-(3,4-dihydroxyphenyl)propanoate;

(1S,2R)-2-(1,2-dimethylpropoxycarbonyloxy)-1-methylpropyl (2S)-2-amino-3-(3,4-dihydroxyphenyl)propanoate;

(1S,2R)-2-(2,2-dimethylpropoxycarbonyloxy)-1-methylpropyl (2S)-2-amino-3-(3,4-dihydroxyphenyl)propanoate;

(1S,2R)-2-butoxycarbonyloxy-1-methylpropyl (2S)-2-amino-3-(3,4-dihydroxyphenyl)propanoate;

(1S,2R)-1-methyl-2-(1-methylbutoxycarbonyloxy)propyl (2S)-2-amino-3-(3,4-dihydroxyphenyl)propanoate;

(1S,2R)-1-methyl-2-(2-methylbutoxycarbonyloxy)propyl (2S)-2-amino-3-(3,4-dihydroxyphenyl)propanoate;

(1S,2R)-1-methyl-2-(3-methylbutoxycarbonyloxy)propyl (2S)-2-amino-3-(3,4-dihydroxyphenyl)propanoate;

(1S,2R)-1-methyl-2-pentyloxycarbonyloxypropyl (2S)-2-amino-3-(3,4-dihydroxyphenyl)propanoate;

(1S,2R)-2-cyclopropoxycarbonyloxy-1-methylpropyl (2S)-2-amino-3-(3,4-dihydroxyphenyl)propanoate;

(1S,2R)-2-cyclobutoxycarbonyloxy-1-methylpropyl (2S)-2-amino-3-(3,4-dihydroxyphenyl)propanoate;

(1S,2R)-2-cyclopentyloxycarbonyloxy-1-methylpropyl (2S)-2-amino-3-(3,4-dihydroxyphenyl)propanoate;

(1S,2R)-2-cyclohexyloxycarbonyloxy-1-methylpropyl (2S)-2-amino-3-(3,4-dihydroxyphenyl)propanoate;

(1S,2R)-2-cycloheptyloxycarbonyloxy-1-methylpropyl (2S)-2-amino-3-(3,4-dihydroxyphenyl)propanoate;

(1S,2R)-1-methyl-2-phenyloxycarbonyloxypropyl (2S)-2-amino-3-(3,4-dihydroxyphenyl)propanoate;

pharmaceutically acceptable salts of any of the foregoing, and pharmaceutically acceptable solvates of any of the foregoing.

In certain embodiments of a compound of Formula (I), the compound is chosen from:

(1R,2S)-2-acetyloxy-1-methylpropyl (2S)-2-amino-3-(3,4-dihydroxyphenyl)propanoate;

(1R,2S)-1-methyl-2-propanoyloxypropyl (2S)-2-amino-3-(3,4-dihydroxyphenyl)propanoate;

(1R,2S)-1-methyl-2-(2-methylpropanoyloxy)propyl (2S)-2-amino-3-(3,4-dihydroxyphenyl)propanoate;

(1R,2S)-2-(2,2-dimethylpropanoyloxy)-1-methylpropyl (2S)-2-amino-3-(3,4-dihydroxyphenyl)propanoate;

(1R,2S)-1-methyl-2-propylcarbonyloxypropyl (2S)-2-amino-3-(3,4-dihydroxyphenyl)propanoate;

(1R,2S)-1-methyl-2-(1-methylpropylcarbonyloxy)propyl (2S)-2-amino-3-(3,4-dihydroxyphenyl)propanoate;

(1R,2S)-1-methyl-2-(2-methylpropylcarbonyloxy)propyl (2S)-2-amino-3-(3,4-dihydroxyphenyl)propanoate;

(1R,2S)-2-(1,1-dimethylpropylcarbonyloxy)-1-methylpropyl (2S)-2-amino-3-(3,4-dihydroxyphenyl)propanoate;

(1R,2S)-2-(1,2-dimethylpropylcarbonyloxy)-1-methylpropyl (2S)-2-amino-3-(3,4-dihydroxyphenyl)propanoate;

(1R,2S)-2-(2,2-dimethylpropylcarbonyloxy)-1-methylpropyl (2S)-2-amino-3-(3,4-dihydroxyphenyl)propanoate;

(1R,2S)-2-butylcarbonyloxy-1-methylpropyl (2S)-2-amino-3-(3,4-dihydroxyphenyl)propanoate;

(1R,2S)-2-(1-methylbutylcarbonyloxy)-1-methylpropyl (2S)-2-amino-3-(3,4-dihydroxyphenyl)propanoate;

(1R,2S)-2-(2-methylbutylcarbonyloxy)-1-methylpropyl (2S)-2-amino-3-(3,4-dihydroxyphenyl)propanoate;

(1R,2S)-2-(3-methylbutylcarbonyloxy)-1-methylpropyl (2S)-2-amino-3-(3,4-dihydroxyphenyl)propanoate;

(1R,2S)-2-hexylcarbonyloxy-1-methylpropyl (2S)-2-amino-3-(3,4-dihydroxyphenyl)propanoate;

(1R,2S)-2-cyclopropylcarbonyloxy-1-methylpropyl (2S)-2-amino-3-(3,4-dihydroxyphenyl)propanoate;

(1R,2S)-2-cyclobutylcarbonyloxy-1-methylpropyl (2S)-2-amino-3-(3,4-dihydroxyphenyl)propanoate;

(1R,2S)-2-cyclopentylcarbonyloxy-1-methylpropyl (2S)-2-amino-3-(3,4-dihydroxyphenyl)propanoate;

(1R,2S)-2-cyclohexylcarbonyloxy-1-methylpropyl (2S)-2-amino-3-(3,4-dihydroxyphenyl)propanoate;

(1R,2S)-2-cycloheptylcarbonyloxy-1-methylpropyl (2S)-2-amino-3-(3,4-dihydroxyphenyl)propanoate;

(1R,2S)-2-phenylcarbonyloxy-1-methylpropyl (2S)-2-amino-3-(3,4-dihydroxyphenyl)propanoate;

(1R,2S)-2-methoxycarbonyloxy-1-methylpropyl (2S)-2-amino-3-(3,4-dihydroxyphenyl)propanoate;

(1R,2S)-2-ethoxycarbonyloxy-1-methylpropyl (2S)-2-amino-3-(3,4-dihydroxyphenyl)propanoate;

(1R,2S)-2-(isoproxycarbonyloxy)-1-methylpropyl (2S)-2-amino-3-(3,4-dihydroxyphenyl)propanoate;

(1R,2S)-2-(tert-butoxycarbonyloxy)-1-methylpropyl (2S)-2-amino-3-(3,4-dihydroxyphenyl)propanoate;

(1R,2S)-1-methyl-2-propoxycarbonyloxypropyl (2S)-2-amino-3-(3,4-dihydroxyphenyl)propanoate;

(1R,2S)-1-methyl-2-(1-methylpropoxycarbonyloxy)propyl (2S)-2-amino-3-(3,4-dihydroxyphenyl)propanoate;

(1R,2S)-1-methyl-2-(2-methylpropoxycarbonyloxy)propyl (2S)-2-amino-3-(3,4-dihydroxyphenyl)propanoate;

(1R,2S)-2-(1,1-dimethylpropoxycarbonyloxy)-1-methylpropyl (2S)-2-amino-3-(3,4-dihydroxyphenyl)propanoate;

(1R,2S)-2-(1,2-dimethylpropoxycarbonyloxy)-1-methylpropyl (2S)-2-amino-3-(3,4-dihydroxyphenyl)propanoate;

(1R,2S)-2-(2,2-dimethylpropoxycarbonyloxy)-1-methylpropyl (2S)-2-amino-3-(3,4-dihydroxyphenyl)propanoate;

(1R,2S)-2-butoxycarbonyloxy-1-methylpropyl (2S)-2-amino-3-(3,4-dihydroxyphenyl)propanoate;

(1R,2S)-1-methyl-2-(1-methylbutoxycarbonyloxy)propyl (2S)-2-amino-3-(3,4-dihydroxyphenyl)propanoate;

(1R,2S)-1-methyl-2-(2-methylbutoxycarbonyloxy)propyl (2S)-2-amino-3-(3,4-dihydroxyphenyl)propanoate;

(1R,2S)-1-methyl-2-(3-methylbutoxycarbonyloxy)propyl (2S)-2-amino-3-(3,4-dihydroxyphenyl)propanoate;

(1R,2S)-1-methyl-2-pentyloxycarbonyloxypropyl (2S)-2-amino-3-(3,4-dihydroxyphenyl)propanoate;

(1R,2S)-2-cyclopropoxycarbonyloxy-1-methylpropyl (2S)-2-amino-3-(3,4-dihydroxyphenyl)propanoate;

(1R,2S)-2-cyclobutoxycarbonyloxy-1-methylpropyl (2S)-2-amino-3-(3,4-dihydroxyphenyl)propanoate;

(1R,2S)-2-cyclopentyloxycarbonyloxy-1-methylpropyl (2S)-2-amino-3-(3,4-dihydroxyphenyl)propanoate;

(1R,2S)-2-cyclohexyloxycarbonyloxy-1-methylpropyl (2S)-2-amino-3-(3,4-dihydroxyphenyl)propanoate;

(1R,2S)-2-cycloheptyloxycarbonyloxy-1-methylpropyl (2S)-2-amino-3-(3,4-dihydroxyphenyl)propanoate;

(1R,2S)-1-methyl-2-phenyloxycarbonyloxypropyl (2S)-2-amino-3-(3,4-dihydroxyphenyl)propanoate;

pharmaceutically acceptable salts of any of the foregoing, and pharmaceutically acceptable solvates of any of the foregoing.

In certain embodiments of a compound of Formula (I), the compound is chosen from:

(1S,2S)-2-acetyloxy-1-methylpropyl (2S)-2-amino-3-(3,4-dihydroxyphenyl)propanoate;

(1S,2S)-1-methyl-2-propanoyloxypropyl (2S)-2-amino-3-(3,4-dihydroxyphenyl)propanoate;

(1S,2S)-1-methyl-2-(2-methylpropanoyloxy)propyl (2S)-2-amino-3-(3,4-dihydroxyphenyl)propanoate;

(1S,2S)-2-(2,2-dimethylpropanoyloxy)-1-methylpropyl (2S)-2-amino-3-(3,4-dihydroxyphenyl)propanoate;

(1S,2S)-1-methyl-2-propylcarbonyloxypropyl (2S)-2-amino-3-(3,4-dihydroxyphenyl)propanoate;

(1S,2S)-1-methyl-2-(1-methylpropylcarbonyloxy)propyl (2S)-2-amino-3-(3,4-dihydroxyphenyl)propanoate;

(1S,2S)-1-methyl-2-(2-methylpropylcarbonyloxy)propyl (2S)-2-amino-3-(3,4-dihydroxyphenyl)propanoate;

(1S,2S)-2-(1,1-dimethylpropylcarbonyloxy)-1-methylpropyl (2S)-2-amino-3-(3,4-dihydroxyphenyl)propanoate;

(1S,2S)-2-(1,2-dimethylpropylcarbonyloxy)-1-methylpropyl (2S)-2-amino-3-(3,4-dihydroxyphenyl)propanoate;

(1S,2S)-2-(2,2-dimethylpropylcarbonyloxy)-1-methylpropyl (2S)-2-amino-3-(3,4-dihydroxyphenyl)propanoate;

(1S,2S)-2-butylcarbonyloxy-1-methylpropyl (2S)-2-amino-3-(3,4-dihydroxyphenyl)propanoate;

(1S,2S)-2-(1-methylbutylcarbonyloxy)-1-methylpropyl (2S)-2-amino-3-(3,4-dihydroxyphenyl)propanoate;

(1S,2S)-2-(2-methylbutylcarbonyloxy)-1-methylpropyl (2S)-2-amino-3-(3,4-dihydroxyphenyl)propanoate;

(1S,2S)-2-(3-methylbutylcarbonyloxy)-1-methylpropyl (2S)-2-amino-3-(3,4-dihydroxyphenyl)propanoate;

(1S,2S)-2-hexylcarbonyloxy-1-methylpropyl (2S)-2-amino-3-(3,4-dihydroxyphenyl)propanoate;

(1S,2S)-2-cyclopropylcarbonyloxy-1-methylpropyl (2S)-2-amino-3-(3,4-dihydroxyphenyl)propanoate;

(1S,2S)-2-cyclobutylcarbonyloxy-1-methylpropyl (2S)-2-amino-3-(3,4-dihydroxyphenyl)propanoate;

(1S,2S)-2-cyclopentylcarbonyloxy-1-methylpropyl (2S)-2-amino-3-(3,4-dihydroxyphenyl)propanoate;

(1S,2S)-2-cyclohexylcarbonyloxy-1-methylpropyl (2S)-2-amino-3-(3,4-dihydroxyphenyl)propanoate;

(1S,2S)-2-cycloheptylcarbonyloxy-1-methylpropyl (2S)-2-amino-3-(3,4-dihydroxyphenyl)propanoate;

(1S,2S)-2-phenylcarbonyloxy-1-methylpropyl (2S)-2-amino-3-(3,4-dihydroxyphenyl)propanoate;

(1S,2S)-2-methoxycarbonyloxy-1-methylpropyl (2S)-2-amino-3-(3,4-dihydroxyphenyl)propanoate;

(1S,2S)-2-ethoxycarbonyloxy-1-methylpropyl (2S)-2-amino-3-(3,4-dihydroxyphenyl)propanoate;

(1S,2S)-2-(isoproxycarbonyloxy)-1-methylpropyl (2S)-2-amino-3-(3,4-dihydroxyphenyl)propanoate;

(1S,2S)-2-(tert-butoxycarbonyloxy)-1-methylpropyl (2S)-2-amino-3-(3,4-dihydroxyphenyl)propanoate;

(1S,2S)-1-methyl-2-propoxycarbonyloxypropyl (2S)-2-amino-3-(3,4-dihydroxyphenyl)propanoate;

(1S,2S)-1-methyl-2-(1-methylpropoxycarbonyloxy)propyl (2S)-2-amino-3-(3,4-dihydroxyphenyl)propanoate;

(1S,2S)-1-methyl-2-(2-methylpropoxycarbonyloxy)propyl (2S)-2-amino-3-(3,4-dihydroxyphenyl)propanoate;

(1S,2S)-2-(1,1-dimethylpropoxycarbonyloxy)-1-methylpropyl (2S)-2-amino-3-(3,4-dihydroxyphenyl)propanoate;

(1S,2S)-2-(1,2-dimethylpropoxycarbonyloxy)-1-methylpropyl (2S)-2-amino-3-(3,4-dihydroxyphenyl)propanoate;

(1S,2S)-2-(2,2-dimethylpropoxycarbonyloxy)-1-methylpropyl (2S)-2-amino-3-(3,4-dihydroxyphenyl)propanoate;

(1S,2S)-2-butoxycarbonyloxy-1-methylpropyl (2S)-2-amino-3-(3,4-dihydroxyphenyl)propanoate;

(1S,2S)-1-methyl-2-(1-methylbutoxycarbonyloxy)propyl (2S)-2-amino-3-(3,4-dihydroxyphenyl)propanoate;

(1S,2S)-1-methyl-2-(2-methylbutoxycarbonyloxy)propyl (2S)-2-amino-3-(3,4-dihydroxyphenyl)propanoate;

(1S,2S)-1-methyl-2-(3-methylbutoxycarbonyloxy)propyl (2S)-2-amino-3-(3,4-dihydroxyphenyl)propanoate;

(1S,2S)-1-methyl-2-pentyloxycarbonyloxypropyl (2S)-2-amino-3-(3,4-dihydroxyphenyl)propanoate;

(1S,2S)-2-cyclopropoxycarbonyloxy-1-methylpropyl (2S)-2-amino-3-(3,4-dihydroxyphenyl)propanoate;

(1S,2S)-2-cyclobutoxycarbonyloxy-1-methylpropyl (2S)-2-amino-3-(3,4-dihydroxyphenyl)propanoate;

(1S,2S)-2-cyclopentyloxycarbonyloxy-1-methylpropyl (2S)-2-amino-3-(3,4-dihydroxyphenyl)propanoate;

(1S,2S)-2-cyclohexyloxycarbonyloxy-1-methylpropyl (2S)-2-amino-3-(3,4-dihydroxyphenyl)propanoate;

(1S,2S)-2-cycloheptyloxycarbonyloxy-1-methylpropyl (2S)-2-amino-3-(3,4-dihydroxyphenyl)propanoate;

(1S,2S)-1-methyl-2-phenyloxycarbonyloxypropyl (2S)-2-amino-3-(3,4-dihydroxyphenyl)propanoate;

pharmaceutically acceptable salts of any of the foregoing, and pharmaceutically acceptable solvates of any of the foregoing.

In certain embodiments of a compound of Formula (I), the compound is chosen from:

(1R,2R)-1-methyl-2-phenylcarbonyloxypropyl (2S)-2-amino-3-(3,4-dihydroxyphenyl)propanoate hydrochloride;

(1S,2S)-1-methyl-2-phenylcarbonyloxypropyl (2S)-2-amino-3-(3,4-dihydroxyphenyl)propanoate hydrochloride;

(1R,2R)-1-methyl-2-(4-fluorophenylcarbonyloxy)propyl (2S)-2-amino-3-(3,4-dihydroxyphenyl)propanoate hydrochloride;

(1S,2S)-1-methyl-2-(4-fluorophenylcarbonyloxy)propyl (2S)-2-amino-3-(3,4-dihydroxyphenyl)propanoate hydrochloride;

(1R,2R)-2-acetyloxy-1-methylpropyl (2S)-2-amino-3-(3,4-dihydroxyphenyl)propanoate hydrochloride;

(1R,2R)-1-methyl-2-(2-methylpropanoyloxy)propyl (2S)-2-amino-3-(3,4-dihydroxyphenyl)propanoate hydrochloride;

(1R,2R)-1-methyl-2-(2-methylpropanoyloxy)propyl (2S)-2-amino-3-(3,4-dihydroxyphenyl)propanoate mesylate;

(1R,2R)-1-methyl-2-phenylcarbonyloxypropyl (2S)-2-amino-3-(3,4-dihydroxyphenyl)propanoate hydrochloride;

(1R,2R)-1-methyl-2-phenylcarbonyloxypropyl (2S)-2-amino-3-(3,4-dihydroxyphenyl)propanoate mesylate;

(1R,2R)-2-ethoxycarbonyloxy-1-methylpropyl (2S)-2-amino-3-(3,4-dihydroxyphenyl)propanoate hydrochloride;

(1R,2R)-2-isopropoxycarbonyloxy-1-methylpropyl (2S)-2-amino-3-(3,4-dihydroxyphenyl)propanoate hydrochloride;

(1R,2R)-1-methyl-2-(2-methylpropoxycarbonyloxy)propyl (2S)-2-amino-3-(3,4-dihydroxyphenyl)propanoate, hydrochloride; and (1R,2R)-1-methyl-2-pentyloxycarbonyloxypropyl (2S)-2-amino-3-(3,4-dihydroxyphenyl)propanoate hydrochloride.

In certain embodiments, a compound of Formula (I) is chosen from:

(1R,2R)-1-methyl-2-phenylcarbonyloxypropyl (2S)-2-amino-3-(3,4-dihydroxyphenyl)propanoate mesylate; and (1R,2R)-1-methyl-2-(2-methylpropanoyloxy)propyl (2S)-2-amino-3-(3,4-dihydroxyphenyl)propanoate hydrochloride.

In certain embodiments of a compound of Formula (I), the compound is a salt chosen from the hydrochloride salt and the mesylate salt.

Synthesis

Synthesis of levodopa dimethyl-substituted diester prodrugs of Formula (I) is disclosed in Xiang et al., U.S. Application Publication No. 2005/0282891, which is incorporated by reference herein in its entirety.

Embodiments of compounds of Formula (I) may be prepared by methods well known in the art. In certain embodiments compounds of Formula (I) may be prepared from readily available starting materials using the following general methods and procedures. It will be appreciated that where typical or preferred process conditions (i.e., reaction temperatures, times, mole ratios of reactants, solvents, pressures) are given, other process conditions can also be used unless otherwise stated. Optimum reaction conditions can vary with the particular reactants or solvent used and may be determined by one skilled in the art by routine optimization procedures. Additionally, as will be apparent to those skilled in the art, conventional protecting groups can be used to prevent certain functional groups from undergoing undesired reactions. Suitable protecting groups for various functional groups as well as suitable conditions for protecting and deprotecting particular functional groups are well known in the art. Furthermore, in certain embodiments, compounds of Formula (I) may contain one or more chiral centers. Accordingly, such compounds can be prepared or isolated as pure stereoisomers, i.e., as individual enantiomers or diastereomers, or as stereoisomer-enriched mixtures. All such stereoisomers (and enriched mixtures) are included within the scope of the embodiments, unless otherwise indicated. Pure stereoisomers (or enriched mixtures) can be prepared using, for example, optically active starting materials or stereoselective reagents well known in the art. Alternatively, racemic mixtures of such compounds can be separated using, for example, chiral column chromatography, chiral resolving agents and the like.

In certain embodiments, compounds of Formula (I) may be prepared by methods well known in the art (see e.g., Wuts and Greene, "Protective Groups in Organic Synthesis," John Wiley & Sons, 4th ed. 2006; Harrison et al., "Compendium of Organic Synthetic Methods," Vols. 1-11, John Wiley & Sons 1971-2003; Larock "Comprehensive Organic Transformations," John Wiley & Sons, 2nd ed. 2000; and Paquette, "Encyclopedia of Reagents for Organic Synthesis," John Wiley & Sons, 11th ed. 2003).

Examples of useful preparative methods can be found in Gallop et al. U.S. Pat. No. 7,144,877, which is incorporated by reference herein in its entirety.

Compounds of Formula (I) may be prepared, for example, from a diol (Scheme 1), from 2-hydroxyethyl halide (Scheme 2), or from ethylene dihalide (Scheme 3). As shown in Scheme 1, a diol (1) can be coupled with Boc-L-levodopa (OBn)$_2$ to provide levodopa derivatives (3). Further, coupling (3) with an acid under appropriate conditions (e.g., DCC/DMAP or TEA) provides catechol protected levodopa derivative intermediate (4), which can be deprotected to provide compound (6) of Formula (I).

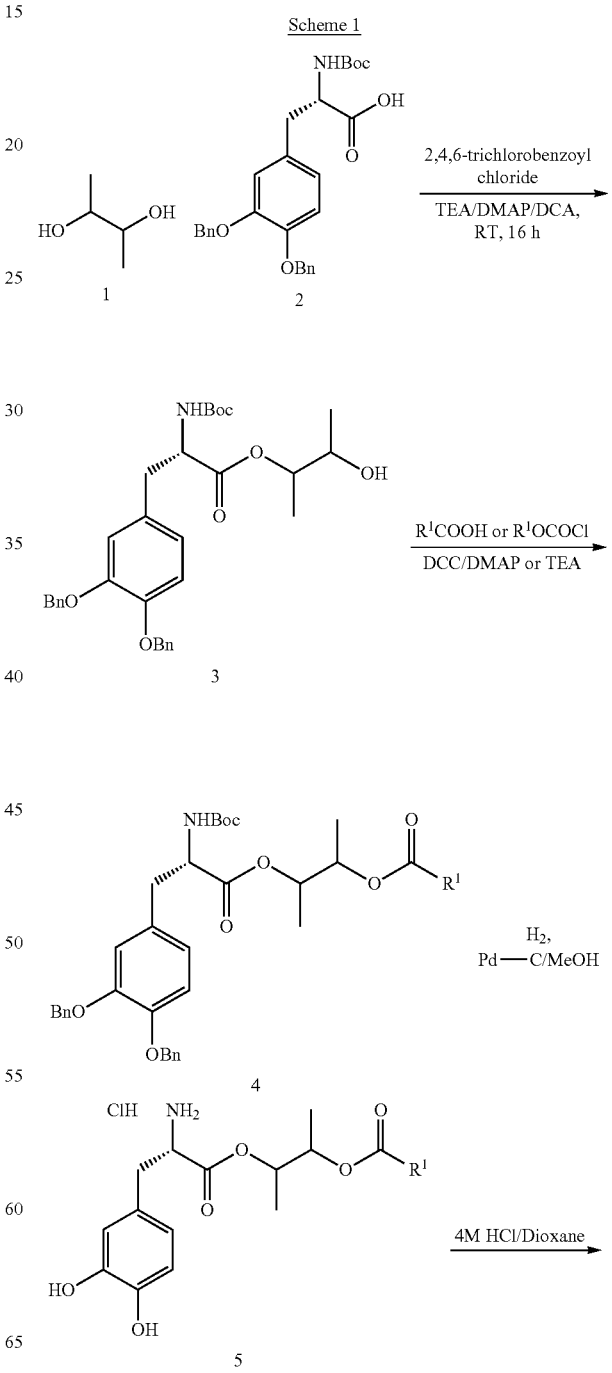

Scheme 1

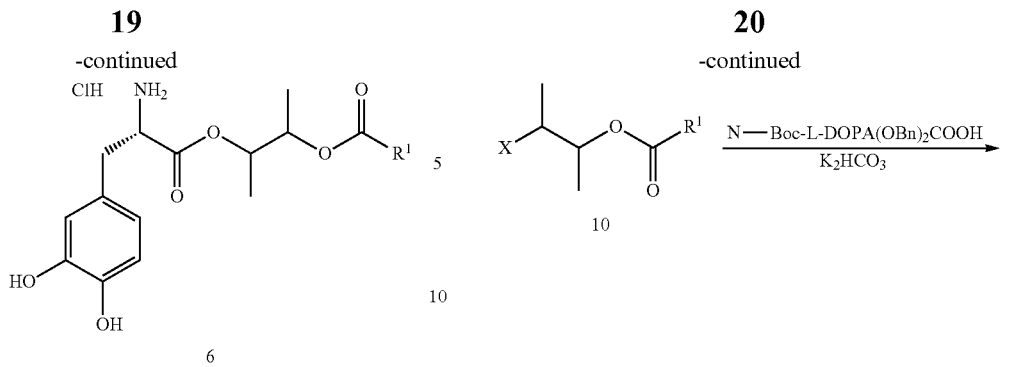

As illustrated in Scheme 2, intermediate (5) may also be prepared by reacting a halide alcohol (7) with a carboxylic acid in an appropriate solvent such as TEA/DMAP/DCM to provide the corresponding ester (8). Ester (8) can be reacted with BOC-protected levodopa to provide intermediate (5), which can be deprotected to provide a compound of Formula (I).

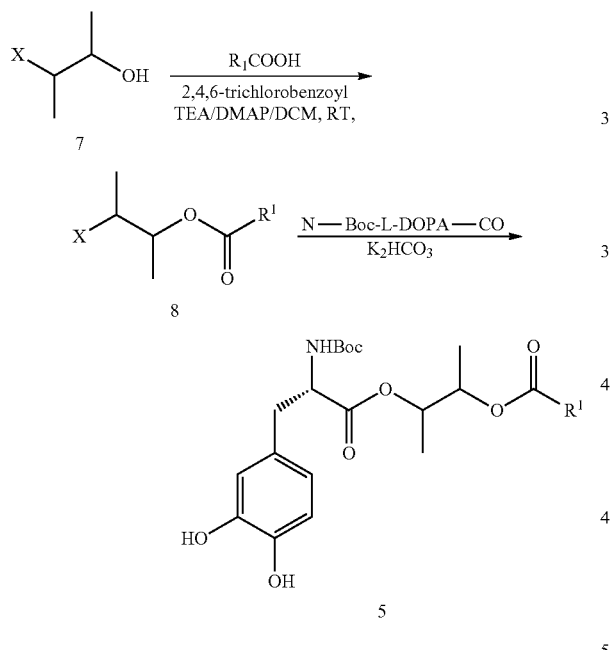

As illustrated in Scheme 3, intermediate (5) may also be prepared by reacting dihalide (9) with a carboxylic acid to form the corresponding ester (10). Ester (10) can be reacted with N-Boc-protected levodopa to provide intermediate (5), following which the amine can be deprotected to provide a compound of Formula (I).

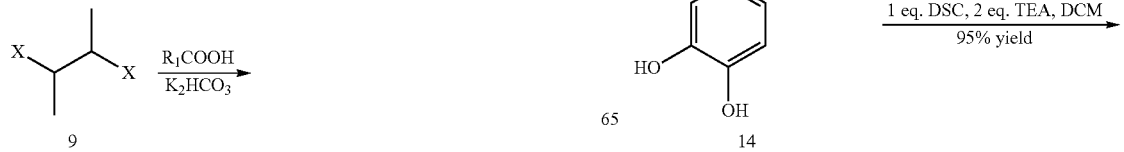

Alternatively, compounds of Formula (I) may be prepared as shown in Scheme 4. As shown in Scheme 4, diol (11) can be reacted with acid chloride (12) to provide the corresponding monoester (13). The catechol groups of Boc-L-dopa (14) can be protected upon conversion to a cyclic carbonate to form intermediate (15). Intermediate (15) is reacted with monoester (13) to form the corresponding catechol protected levodopa intermediate (16). The catechol groups are deprotected to form non-catechol protected intermediate (17), following which the amine can be deprotected to provide levodopa prodrug (18) of Formula (I).

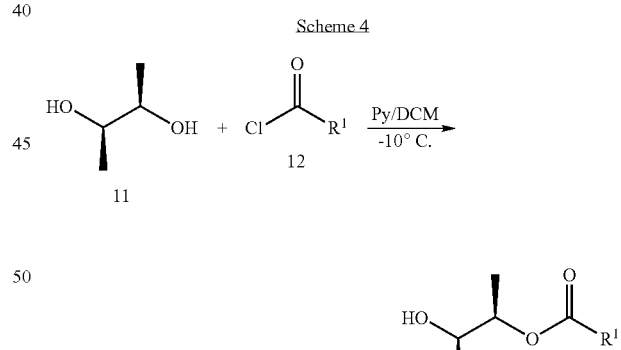

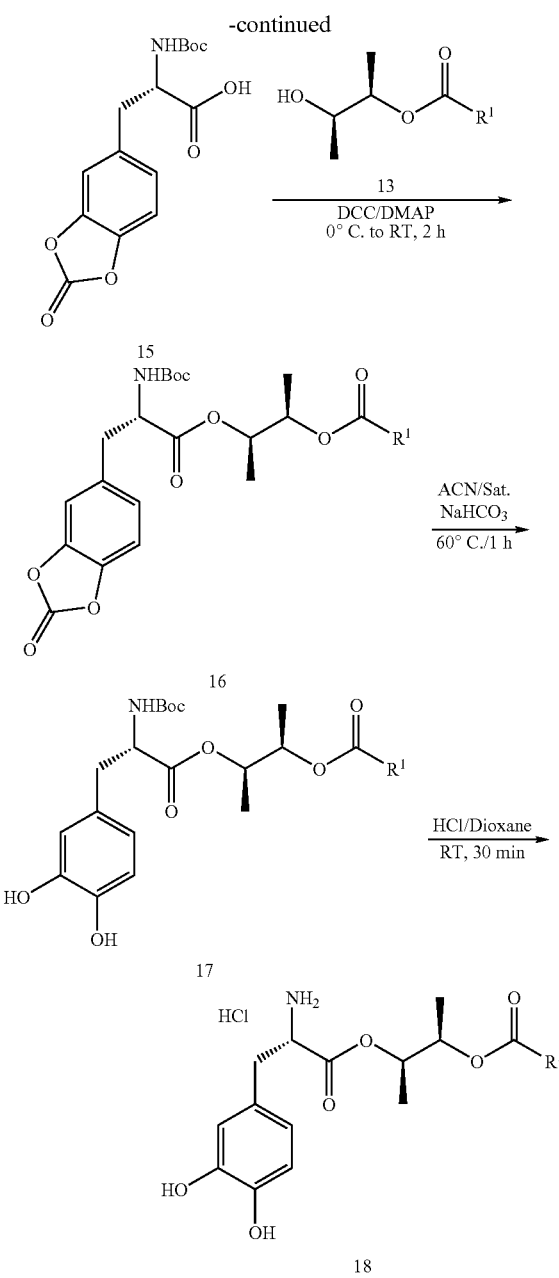

With appropriate manipulation and protection of the chemical functionalities, synthesis of compounds of Formula (I) is accomplished by methods analogous to those described above and in the experimental section.

Uses

Levodopa prodrugs of Formula (I) are precursors of dopamine. Thus, compounds of Formula (I) provided by the present disclosure may be administered to a patient suffering from any disease or disorder for which the parent drug, levodopa, is known or hereafter discovered to be therapeutically effective. Compounds of Formula (I) may be administered to a patient, such as a human, to treat a disease or disorder such as Parkinson's disease. Methods comprise administering to a patient in need of such treatment a therapeutically effective amount of at least one compound of Formula (I). In therapeutic methods provided by the present disclosure, a therapeutically effective amount of at least one compound of Formula (I) may be administered to a patient suffering from a disease such as Parkinson's disease, depression, attention deficit disorder, schizophrenia, manic depression, cognitive impairment disorders, restless legs syndrome, periodic limb movement disorders, tardive dyskinesia, Huntington's disease, Tourette's syndrome, hypertension, addictive disorders, stroke, congestive heart failure, excessive daytime sleepiness, dystonia, memory and learing deficits or loss, or Lewy Body disease. In certain embodiments, a therapeutically effective amount of at least one compound of Formula (I) may be administered to a patient for treating depression, attention deficit disorder, schizophrenia, manic depression, cognitive impairment disorders, restless legs syndrome, periodic limb movement disorders, tardive dyskinesia, Huntington's disease, Tourette's syndrome, hypertension, addictive disorders, congestive heart failure, stroke, excessive daytime sleepiness, dystonia, and memory and learning deficit or loss.

In certain embodiments, compounds of Formula (I) or pharmaceutical compositions thereof may be co-administered with another therapeutic agent or drug, such as a decarboxylase inhibitor such as carbidopa or benserazide, or a prodrug thereof, which may act as a protectant to inhibit or prevent premature decarboxylation of a compound of Formula (I) and/or the levodopa metabolite. Compounds of Formula (I) may be delivered from the same dosage form as an L-aromatic amino acid decarboxylase inhibitor or from a different dosage form. Compounds of Formula (I) may be administered at the same time as, prior to, or subsequent to, the administration of a decarboxylase inhibitor. Compounds of Formula (I) together with a decarboxylase inhibitor or decarboxylase inhibitor prodrug or derivative may be administered to a patient, such as a human, to treat a disease or disorder such as Parkinson's disease. Additionally, the therapeutic effectiveness of the above combinations may be enhanced by co-administration of another pharmaceutically active agent such as a catechol-O-methyltransferase (COMT) inhibitor such as entacapone, an entacapone prodrug, tolecapone, and/or a tolecapone prodrug. Further, in certain embodiments, compounds of Formula (I) or pharmaceutical compositions thereof may be administered to a patient, such as a human, together with (i) a decarboxylase inhibitor such as carbidopa, a carbidopa prodrug, benserazide, or a benserazide prodrug, and (ii) a pharmaceutically active agent such as a COMT inhibitor or prodrug thereof, to treat a disease or disorder such as Parkinson's disease.

Compounds of Formula (I) may be included in a pharmaceutical composition and/or dosage form adapted for oral administration, although compounds of Formula (I) may also be administered by any other convenient route, such as for example, by injection, infusion, inhalation, transdermal, or absorption through epithelial or mucosal membranes (e.g., oral, rectal, and/or intestinal mucosa).

Compounds of Formula (I) or pharmaceutical compositions thereof may provide therapeutic or prophylactic plasma and/or blood concentrations of levodopa following oral administration to a patient. The promoiety(ies) of compounds of Formula (I) may be cleaved in vivo either chemically and/or enzymatically to release the parent drug, levodopa. One or more enzymes present in the stomach, intestinal lumen, intestinal tissue, blood, liver, brain, or any other suitable tissue of a patient may enzymatically cleave the promoiety of the administered compounds. For example, the carboxyl ester promoiety of compounds of Formula (I) may be cleaved after absorption from the gastrointestinal tract (e.g., in intestinal tissue, blood, liver, or other suitable tissue of a mammal). In certain embodiments, compounds of Formula (I) may be actively transported across the intestinal endothelium by active transporters expressed throughout the gastrointestinal tract including the small intestine and colon. Levodopa may remain conjugated to the carboxyl ester promoiety during transit across the intestinal mucosal barrier to prevent or minimize presystemic metabolism. In certain embodiments, a compound of Formula (I) is essentially not metabolized to levodopa within gastrointestinal enterocytes, but is metabolized to levodopa within the systemic circulation, for example in the plasma. In such embodiments, compounds of Formula (I) may be absorbed into the systemic circulation from the small and large intestines either by active transport, passive diffusion, or by both active and passive processes. The promoiety of a compound of Formula (I) may allow the compound of Formula (I) to be absorbed into the systemic circulation either by active transport, passive diffusion, or by both active and passive processes.

Compounds of Formula (I) may be administered in similar amounts and using a similar schedule as described in the art for levodopa. For example, compounds of Formula (I) may be useful in treating Parkinson's disease by administration of a compound of Formula (I) together with a decarboxylase inhibitor such as carbidopa or a prodrug of carbidopa, in certain embodiments by the oral route, to a mammalian subject in need of the treatment. In a human subject weighing about 70 kg, compounds of Formula (I) may be administered at a dose over time having an equivalent weight of levodopa of from about 10 mg to about 10 g per day, and in certain embodiments, an equivalent weight of levodopa of from about 100 mg to about 3 g per day. A dose of a compound of Formula (I) taken at any one time can have an equivalent weight of levodopa of from about 10 mg to about 3 g. A dose may be adjusted by one skilled in the art based on several factors, including, for example, the body weight and/or condition of the subject treated, the dose of the decarboxylase inhibitor or prodrug of a decarboxylase inhibitor being administered, the severity of the disease being treated, the incidence of side effects, the manner of administration, and the judgment of the prescribing physician. Doses and regimens may be determined by methods known to one skilled in the art.

Compounds of Formula (I) may be assayed in vitro and in vivo for the desired therapeutic or prophylactic activity prior to use in humans. For example, in vitro assays may be used to determine whether administration of a compound of Formula (I) is a substrate of a transporter protein, including organic cation transporters such as OCTN1 and OCTN2. Examples of certain assay methods applicable to analyzing the ability of compounds of Formula (I) to act as a substrate for a transporter protein are disclosed in Zerangue et al., U.S. Application Publication No. 2003/0158254, which is incorporated by reference herein in its entirety. In vivo assays may also be used to determine whether administration of a compound of Formula (I) is therapeutically effective. Compounds of Formula (I) may also be demonstrated to be effective and safe using animal model systems.

In certain embodiments, a therapeutically effective dose of a compound of Formula (I) may provide therapeutic benefit without causing substantial toxicity. Toxicity of compounds of Formula (I) may be determined using standard pharmaceutical procedures and may be ascertained by one skilled in the art. The dose ratio between toxic and therapeutic effect is the therapeutic index. A dosage of a compound of Formula (I) may be within a range capable of establishing and maintaining a therapeutically effective circulating plasma and/or blood concentration of levodopa that exhibits little or no toxicity.

In addition to the use of compounds of Formula (I) and pharmaceutical compositions comprising compounds of Formula (I) provided by the present disclosure for treating Parkinson's disease, compounds of Formula (I) and compositions thereof may also be useful for treating other dopamine-related diseases. Dopamine-related diseases can be characterized by either insufficient or excessive functional dopaminergic activity in the central nervous system. Examples of other dopamine-related diseases include, but are not limited to, affective disorders such as depression and attention deficit disorder, psychotic disorders such as schizophrenia and manic depression, cognitive impairment disorders such as mild cognitive impairment, movement disorders such as restless legs syndrome, periodic limb movement disorders, tardive dyskinesia, hypertension, Huntington's disease, and Tourette's syndrome, addictive disorders such as alcohol addiction or abuse, nicotine addiction or abuse, and drug addiction and abuse, congestive heart failure, and excessive daytime sleepiness. For the treatment of these and other dopamine-related diseases, compounds of Formula (I) may be co-administered with an additional active agent such as, for example, a decarboxylase inhibitor and/or a COMT inhibitor. Therapeutically effective doses for treating dopamine-related diseases may be determined by the methods disclosed herein for the treatment of Parkinson's disease and/or by methods known in the art.

Parkinson's Disease

Parkinson's disease (PD) is a progressive neurodegenerative disorder that affects about 1% of the population over 55 years of age. The pathological manifestation of PD is the loss of dopaminergic neurons in the Substantia Nigra pars compacta and the presence of intracycloplasmic inclusions, called Lewy bodies, formed mainly by α-synuclein and ubiquitin. The main symptoms of PD are tremor, bradykinesia, hypokinesia, and balance and coordination disturbances. Dopamine replacement therapy can alleviate the symptoms of PD, however as the disease progresses, drug-related side effects emerge as well as disabling symptoms that are not responsive to the treatment. Although the cause of PD is unknown, dopaminergic cell loss has been associated with several mechanisms of cell damage including excitotoxicity, disturbed calcium homeostasis, inflammation, apoptosis, distress energy metabolism, and protein aggregation. Because patients with PD have a normal lifespan, they must endure crippling symptoms for many years, severely impacting their quality of life. Therefore, a neuroprotective therapy that can stop or reduce the continual loss of dopaminergic neurons is needed.

Levodopa has been shown effective in treating vascular parkinsonism (Zijlmans et al., *J Neurol Neurosurg Psychiatry* 2004, 75, 545-547).

The efficacy of a compound of Formula (I) in treating Parkinson's disease may be assessed using animal models of Parkinson's disease and in clinical studies. Animal models of PD are known (see, e.g., O'Neil et al., *CNS Drug Rev.* 2005, 11(1), 77-96; Faulkner et al., *Ann. Pharmacother.* 2003, 37(2), 282-6; Olson et al., *Am. J. Med.* 1997, 102(1), 60-6; Van Blercom et al., *Clin Neuropharmacol.* 2004, 27(3), 124-8; Cho et al., *Biochem. Biophys. Res. Commun.* 2006, 341, 6-12; Emborg, *J. Neuro. Meth.* 2004, 139, 121-143; Tolwani et al., *Lab Anim Sci* 1999, 49(4), 363-71; Hirsch et al., *J Neural Transm Suppl* 2003, 65, 89-100; Orth and Tabrizi, *Mov Disord* 2003, 18(7), 729-37; and Betarbet et al., *Bioessays* 2002, 24(4), 308-18).

Schizophrenia

Schizophrenia includes a group of neuropsychiatric disorders characterized by dysfunctions of the thinking process, such as delusions, hallucinations, and extensive withdrawal of the patient's interests from other people. Schizophrenia includes the subtypes of paranoid schizophrenia characterized by a preoccupation with delusions or auditory hallucinations, hebephrenic or disorganized schizophrenia characterized by disorganized speech, disorganized behavior, and flat or inappropriate emotions; catatonic schizophrenia dominated by physical symptoms such as immobility, excessive motor activity, or the assumption of bizarre postures; undifferentiated schizophrenia characterized by a combination of symptoms characteristic of the other subtypes; and residual schizophrenia in which a person is not currently suffering from positive symptoms but manifests negative and/or cognitive symptoms of schizophrenia (see DSM-IV-TR classifications 295.30 (Paranoid Type), 295.10 (Disorganized Type), 295.20 (Catatonic Type), 295.90 (Undifferentiated Type), and 295.60 (Residual Type) (Diagnostic and Statistical Manual of Mental Disorders, 4$^{th}$ Edition, American Psychiatric Association, pp. 297-319, 2005). Schizophrenia includes these and other closely associated psychotic disorders such as schizophreniform disorder, schizoaffective disorder, delusional disorder, brief psychotic disorder, shared psychotic disorder, psychotic disorder due to a general medical condition, substance-induced psychotic disorder, and unspecified psychotic disorders (DSM-IV-TR, 4$^{th}$ Edition, pp. 297-344, American Psychiatric Association, 2005). Schizoaffective disorder characterized by symptoms of schizophrenia as well as mood disorders such as major depression, bipolar mania, or mixed mania, is included as a subtype of schizophrenia.

Schizophrenia symptoms can be classified as positive, negative, or cognitive. Positive symptoms of schizophrenia include delusion and hallucination, which can be measured using, for example, the Positive and Negative Syndrome Scale (PANSS); see Kay et al., *Schizophrenia Bulletin* 1987, 13, 261-276). Negative symptoms of schizophrenia include affect blunting, anergia, alogia and social withdrawal, which can be measured for example, using (the Scales for the Assessment of Negative Symptoms (SANS) (see Andreasen, 1983, *Scales for the Assessment of Negative Symptoms* (SANS), Iowa City, Iowa). Cognitive symptoms of schizophrenia include impairment in obtaining, organizing, and using intellectual knowledge which can be measured using the Positive and Negative Syndrome Scale-cognitive subscale (PANSS-cognitive subscale) (Lindenmayer et al., *J Nerv Ment Dis* 1994, 182, 631-638) or by assessing the ability to perform cognitive tasks such as, for example, using the Wisconsin Card Sorting Test (see, e.g., Green et al., *Am J Psychiatry* 1992, 149, 162-67; and Koren et al., *Schizophr Bull* 2006, 32(2), 310-26).

Treating schizophrenia encompasses treating one or more symptoms, positive, negative, cognitive, and other associated features, of schizophrenia. Examples of symptoms of schizophrenia include delusions, hallucinations, disorganized speech, affective flattening, alogia, anhedonia, inappropriate affect, dysphoric mood (in the form of, for example, depression, anxiety, and/or anger), and some indications of cognitive dysfunction.

Administration of high doses of a dopamine D2 receptor agonist or precursor thereof such as levodopa, either alone or concomitant with an antipsychotic drug, has been shown to exacerbate psychosis, or even induce psychosis in non-psychotic patients (Lehrman and Sharar, *J. Ment Health Admin*, 1997, 24, 227-250; Yaryura-Tobias et al., *Curr Ther Res Clin Exp* 1970, 12, 528-31; and Yaryura-Tobias et al., *Dis Nerv Syst* 1970, 31, 60-63). However, relatively low doses of levodopa given as adjunctive treatment with typical antipsychotic drugs improves the clinical outcome in schizophrenia (see Jaskiw and Popli, *Psychopharmacology* 2004, 171, 365-374), suggesting an enhanced effect on negative symptoms and cognitive impairment without worsening of psychotic symptoms (Alpert and Friedhoff, *Am J Psychiatry* 1980, 135, 1329-32; Bruno and Bruno, *Acta Psychiatr Scand*, 1966, 42, 264-71; Buchanan et al., *Aust N Z J Psychiatry* 1975, 9, 269-71; Gerlach and Luhdorf, *Psychopharmacologia* 1975, 44, 105-110; Inanaga et al., *Folia Psychiatr Neurol Jpn* 1975, 29, 123-43; and Kay and Opler, *Int J Psychiat Med* 1985-86, 15, 293-98). The results of these studies suggest that adjunctive low-dose levodopa together with a low dose of a conventional antipsychotic drug can be expected to generate a therapeutic profile similar to that of atypical antipsychotic drugs, including enhanced treatment efficacy against negative symptoms and cognitive impairment in schizophrenia, with retained therapeutic effects on positive symptoms and without concomitant increased EPS liability. Because the severity of cognitive impairment has a crucial impact on treatment outcome (Green, *Am J Psychiatry* 1996, 153, 321-330; and Harvey et al., *Am J Psychiatry* 1998, 155, 1080-1086) the use of adjunctive, low-dose levodopa with selective dopamine D2 antagonists might also prove efficacious in treating both the positive and negative or cognitive symptoms of schizophrenia (see also, Tran, U.S. application Ser. No. 11/855,641, which is incorporated by reference herein in its entirety).

Compounds of Formula (I) and pharmaceutical compositions thereof may be used to treat a positive symptom of schizophrenia, a negative or cognitive symptom of schizophrenia, both a positive and a negative or cognitive symptom of schizophrenia and/or closely associated psychotic disorders such as schizophreniform disorder, schizoaffective disorder, delusional disorder, brief psychotic disorder, shared psychotic disorder, psychotic disorder due to a general medical condition, substance-induced psychotic disorder, and/or unspecified psychotic disorders in a patient (DSM-IV-TR, 4$^{th}$ Edition, pp. 297-344, American Psychiatric Association, 2005). Positive symptoms of schizophrenia include delusion and hallucination. Negative symptoms of schizophrenia include affect blunting, anergia, alogia, and social withdrawal. Cognitive symptoms of schizophrenia include impairment in obtaining, organizing, and using intellectual knowledge. In certain embodiments, compounds of Formula (I) and pharmaceutical compositions thereof may be used to treat both a positive and a negative or cognitive symptom of schizophrenia by orally administering a compound of Formula (I) or pharmaceutical compositions thereof to a patient in need of such treatment.

The efficacy of compounds of Formula (I) and pharmaceutical compositions thereof in treating schizophrenia may be determined by methods known to those skilled in the art. For example, negative, positive, and/or cognitive symptom(s) of schizophrenia may be measured before and after treatment of the patient. Reduction in such symptom(s) indicates that a patient's condition has improved. Improvement in the symptoms of schizophrenia may be assessed using, for example, the Scale for Assessment of Negative Symptoms (SANS), Positive and Negative Symptoms Scale (PANSS) (see, e.g., Andreasen, 1983, *Scales for the Assessment of Negative Symptoms* (SANS), Iowa City, Iowa; and Kay et al., *Schizophrenia Bulletin* 1987, 13, 261-276), and using Cognitive Deficits tests such as the Wisconsin Card Sorting Test (WCST) and other measures of cognitive function (see, e.g., Keshavan et al., *Schizophr Res* 2004, 70(2-3), 187-194; Rush, Handbook of Psychiatric Measures, American Psychiatric Publishing 2000; Sajatovic and Ramirez, Rating Scales in Mental Health, 2nd ed, Lexi-Comp, 2003, Keefe, et al., Schizophr Res. 2004, 68(2-3), 283-97; and Keefe et al., Neuropsychopharmacology 2006, 31(9), 2033-46).

The efficacy of compounds of Formula (I) and pharmaceutical compositions thereof may also be evaluated using animal models of schizophrenic disorders (see e.g., Geyer and Moghaddam, in "Neuropsychopharmacology," Davis et al., Ed., Chapter 50, pp. 689-701, American College of Neuropsychopharmacology, 2002). For example, conditioned avoidance response behavior (CAR) and catalepsy tests in rats are shown to be useful in predicting antipsychotic activity and EPS effect liability, respectively (Wadenberg et al., Neuropsychopharmacology 2001, 25, 633-641).

Restless Legs Syndrome

Restless legs syndrome (RLS) afflicts between 5 and 10% of the general population. Although the clinical origin of RLS is unknown, characteristic symptoms of RLS include lower extremity dysesthesias or paresthesias, motor restlessness, nocturnal increase of paresthesias and motor restlessness, and symptoms that increase at rest, i.e., sitting or lying. Typically, symptoms increase at night (Garcia-Borreguero et al., Neurol. 2002, 11(2), 1573-79). RLS may start at any age, even during childhood, although is usually observed in adults. The clinical course generally changes over time, but tends to become more pronounced with age, with up to 28% of those over 65 being affected (Clark, J. Am. Fam. Prac. 2001, 14(3), 368-374).

RLS is an intensely uncomfortable sensory-motor disorder. Besides sensory symptoms such as paresthesia, which is a sensation of numbness, tingling, burning or pain, accompanied by an urge to move the limbs, patients also experience motor symptoms. When awake and sitting or lying down, the patient has rhythmic or semi-rhythmic movements of the legs (i.e., dysesthesias). While sleeping, patients frequently demonstrate similar semi-rhythmic legs movements, which have been referred to as periodic leg movements during sleep (PLMS). These jerky leg movements are repetitive, highly stereotypical and are characterized by extension of the big toe along with flexion of the ankle, knee and sometimes the hip (i.e., a Babinski-like movement) (Clark, supra). About 85-90% of RLS sufferers also exhibit PLMS and these patients complain of daytime fatigue and sleepiness or insomnia, which have a profound negative effect on quality of life, including daytime fatigue, poor work performance and interrupted social and/or family life (National Institutes of Health, 2003 National Sleep Disorders Research Plan, pp. 76-79).

The origin of RLS and PLMS is unknown and most cases are classified as idiopathic. Clinical and laboratory findings suggest that the dopaminergic neurotransmitter system may be involved. Defects in the opioid and serotonin systems may also play a role (Adler, Clin. Neuropharm. 1997, 20(2), 148-151). RLS is more prevalent in women than men and in individuals of Northern European ancestry. The inheritance pattern of RLS suggests an autosomal dominant mode of transmittance, but the genes accounting for this observation are not known.

Certain patient populations exhibit RLS more frequently than does the general population. In particular, iron deficiency has been associated with RLS, as have decreased levels of magnesium and folate. Dialysis patients, perhaps because of the prevalence of associated anemia, are frequently afflicted, with 20% to 57% having symptoms of RLS. In addition, pregnant women often complain of RLS, although symptoms usually diminish or disappear after delivery (Clark, supra).

Diagnostic criteria for RLS includes a distressing urge to move the limbs because of paraesthesias or spontaneous jerks in the legs or less often in other body parts, a worsening of these symptoms at rest, a temporary relief by motor activity, and worsening of the symptoms in the evening or during the night (see e.g. Mathis, Swiss Med Wkly 2005, 135, 687-96; and Allen et al., Sleep Med 2003, 4, 101-19).

Levodopa has been shown to be effective in treating RLS (Ondo and Jankovic, Neurology 1996, 47, 1435-41; von Scheele, Lancet 1986, 2(8504), 426-7; and Conti et al., Mot Disord 2007, 22(13), 1943-1951).

The efficacy of a compound of a levodopa prodrug in treating RLS may be assessed using animal models of RLS and in clinical studies.

Huntington's Disease

Huntington's disease is an autosomal dominant neurodegenerative disorder in which specific cell death occurs in the neostriatum and cortex (Martin, N Engl J Med 1999, 340, 1970-80). Onset usually occurs during the fourth or fifth decade of life, with a mean survival at age onset of 14 to 20 years. Huntington's disease is universally fatal, and there is no effective treatment. Symptoms include a characteristic movement disorder (Huntington's chorea), cognitive dysfunction, and psychiatric symptoms. The disease is caused by a mutation encoding an abnormal expansion of CAG-encoded polyglutamine repeats in the protein, huntingtin. A number of studies suggest that there is a progressive impairment of energy metabolism, possibly resulting from mitochondrial damage caused by oxidative stress as a consequence of free radical generation.

Levodopa has shown effectiveness in treating rigidity associated with Huntington's disease (see Bonelli and Wenning, Current Pharmaceutical Design 2006, 12(21), 2701-2720).

The efficacy of a levodopa prodrug for treating Huntington's disease may be assessed using animal models of Huntington's disease and clinical studies. Animal models of Huntington's disease are disclosed, for example, in Riess and Hoersten, U.S. Application Publication No. 2007/0044162; Rubinsztein, Trends in Genetics, 2002, 18(4), 202-209; Matthews et al., J. Neuroscience 1998, 18(1), 156-63; Tadros et al., Pharmacol Biochem Behav 2005, 82(3), 574-82; and Kaddurah-Daouk et al., U.S. Pat. No. 6,706,764 and U.S. Application Publication No. 2007/0044162. An example of a placebo-controlled clinical trial evaluating the efficacy of a compound to treat Huntington's disease is disclosed in Verbessem et al., Neurology 2003, 61, 925-230.

Dystonia

Dystonia is involuntary, slow, repetitive, sustained muscle contractions that may cause freezing in the middle of an action, as well as twisting or turning of the trunk, the entire body, or part of the body.

Dystonia is a neurological syndrome characterized by involuntary, patterned, sustained, or repetitive muscle contractions of opposing muscles, causing twisting movements and abnormal postures. Causes of dystonia include a severe lack of oxygen to the brain that occurs at birth or later in life, Parkinson's disease, multiple sclerosis, toxicity due to accumulation of certain metals such as copper in Wilson's disease, stroke, and as side effects to antipsychotic drugs. Chronic dystonia is usually genetic. Types and symptoms of dystonia include focal dystonias confined to particular muscles or muscle groups such as blepharospasm, oromandibular dystonia, spasmodic dysphonia, cervical dystonia, and task-specific dystonias, segmental dystonias in which certain parts of the body are affected, and generalized dystonias in which muscles throughout the body are affected. Dopa-responsive dystonia, characterized by child hood onset, parkinsonian features, gait and postural abnormalities, diurnal fluctuation, and autosomal dominant inheritance is a genetic disorder representing up to about 5% of childhood dystonias. Levodopa substantially improves or can completely resolve this type of dystonia (Jankovic, *Lancet Neurol* 2006, 5, 864-72; and Schneider et al., *Neurology* 2006, 66(4), 599-601).

The efficacy of a compound of a levodopa prodrug in treating dystonia may be assessed using animal models of dystonia and in clinical studies.

Tardive Dyskinesia

Tardive dyskinesia is a neurological disorder caused by the long-term or high-dose use of dopamine antagonists such as antipsychotics (Rascol and Fabre, *Clinical Neuropharmacology* 2001, 24(6), 313-323). Tardive dyskinesia is characterized by repetitive, involuntary, purposeless movements such as grimacing, tongue protrusion, lip smacking, puckering and pursing of the lips, and rapid eye blinking, and can also involve rapid movements of the arms, legs, and trunk.

Studies suggest that levodopa can be useful in treating movement disorders induced by neuroleptic drugs such as tardive dyskinesia (Rascol and Fabre, *Clinical Neuropharmacology* 2001, 24(6), 313-323; Soares and McGrath, *Schizophr Res* 1999, 39(1), 1-16; and Ebadi and Srnivasan, *Pharmacological Reviews* 1996, 47(4), 575-604), Efficacy of tardive dyskinesia treatment can be assessed using animal models (Takeuchi et al., *Prog Neuro-Psychopharmacol & Biol Psychiat* 1998, 22, 679-691; Abilio et al., *Psychopharmacology* 2002, 161, 340-347; Queiroz and Frussa-Filho, *Prog Neuro-Psychopharmacol & Biol Psychiat* 1999, 23, 1405-1418; Andreassen et al., *Br J Pharmacol* 1996, 119(4), 751-7; Dutra et al., *Prog Neuro-Psychopharmacology & Biol Psychiatry* 2002, 26, 487-495; and Shoham, *Brain Res* 2004, 1004, 142-147), and in clinical trials.

Stroke

Levodopa combined with physiotherapy is shown to improve motor recovery after stroke (Scheidtmann et al., *The Lancet*, 2001, 358, 787-790; and Floel et al., *Neurology* 2005, 65(3), 472-4).

The efficacy of a compound of a levodopa prodrug in treating stroke may be assessed using animal models of stroke and in clinical studies.

Learning and Memory Disorders and Deficits

Levodopa is shown to be effective in treating cognitive dysfunction in patients with Parkinson's disease (Cools, *Neuroscience Biobehavioral Rev* 2006, 30, 1-23; and Kulisevsky, *Drugs Aging* 2000, 16(5), 365-79), enhance training effects in motor memory formation in the elderly (Floel et al., *Neurobiology of Aging* 2006, PMID 17098331) and improve word learning in healthy patients (Knecht et al., *Ann. Neurol* 2004, 56(1), 20-6).

The efficacy of a compound of a levodopa prodrug in treating learning and memory disorders may be assessed using animal models of learning and memory disorders and in clinical studies.

Excessive Daytime Sleepiness

Excessive daytime sleepiness (EDS), also known as hypersomnia is characterized by recurrent episodes of excessive daytime sleepiness or prolonged nighttime sleep. Hypersomnia can be caused by genetics, brain damage, and disorders such as clinical depression and fibromyalgia and can also be a symptom of other sleep disorders such as narcolepsy, sleep apnea, and restless legs syndrome. Hypersomnia can be diagnosed using the Epworth sleepiness test. Levodopa has shown efficacy in treating hypersomnia (Silber, *Neurologic Clinics* 2001, 19(1), 173-86; Paus et al., *Movement Disorders* 2003, 18(6), 659-667; Hogl et al., *Movement Disorders* 2003, 18(3), 319-323; and O'Suilleabhain and Dewey, *Arch Neurol* 2002, 59, 986-989).

The efficacy of a compound of a levodopa prodrug in treating excessive daytime sleepiness may be assessed using animal models of excessive daytime sleepiness and in clinical studies.

Depression

Depressive disorders include major depressive disorder, dysthymic disorder, premenstrual dysphoric disorder, minor depressive disorder, recurrent brief depressive disorder, and postpsychotic depressive disorder of schizophrenia (see DSM IV).

The efficacy of compounds provided by the present disclosure for treating depression can be evaluated in animal models of depression such as the forced swim test (Porsolt et al., *Nature* 1977, 266, 525-532; and Porsolt et al., *Arch Int Pharmacodyn* 1997, 229, 327-336), the tail suspension test (Cryan et al., *Trends Pharmacol Sci* 2002, 23, 238-245; and Cryan and Mombereau, *Mol Psychiatr* 2004, 9, 1050-1062), and well as other (Porsolt, *Rev. Neurosci* 2000, 11, 53-58).

Pharmaceutical Compositions

Pharmaceutical compositions provided by the present disclosure may comprise a therapeutically effective amount of a compound of Formula (I), and in certain embodiments, in purified form, together with a suitable amount of one or more pharmaceutically acceptable vehicles, so as to provide a composition for proper administration to a patient. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The present compositions may also contain wetting agents, emulsifying agents, and/or pH buffering agents. In addition, auxiliary, stabilizing, thickening, lubricating, and/or coloring agents may be used. In certain embodiments, pharmaceutical compositions may be in the form of a capsule. Other examples of suitable pharmaceutical vehicles are described in the art.

Pharmaceutical compositions comprising a compound of Formula (I) may be manufactured by means of conventional mixing, dissolving, granulating, dragee-making, levigating, emulsifying, encapsulating, entrapping, or lyophilizing processes. Pharmaceutical compositions may be formulated in a conventional manner using one or more physiologically acceptable carriers, diluents, excipients, or auxiliaries, which facilitate processing of compounds of Formula (I) or crystalline form thereof and one or more pharmaceutically acceptable vehicles into formulations that can be used pharmaceutically. Proper formulation is dependent upon the route of administration chosen. In certain embodiments, a pharmaceutical composition comprising a compound of Formula (I) or crystalline form thereof may be formulated for oral administration, and in certain embodiments for sustained release oral administration. Pharmaceutical compositions provided by the present disclosure may take the form of solutions, suspensions, emulsion, tablets, pills, pellets, capsules, capsules containing liquids, powders, sustained-release formulations, suppositories, emulsions, aerosols, sprays, suspensions, or any other form suitable for use.

In certain embodiments, a compound of Formula (I) may be incorporated into pharmaceutical compositions to be administered orally. Oral administration of such pharmaceutical compositions may result in uptake of a compound of Formula (I) throughout the intestine and entry into the systemic circulation. Such compositions may be prepared in a manner known in the pharmaceutical art and comprise at least one compound of Formula (I) and at least one pharmaceutically acceptable vehicle. Pharmaceutical compositions may include a therapeutically effective amount of at least one compound of Formula (I), in some embodiments, in purified form, together with a decarboxylase inhibitor such as carbidopa, a carbidopa prodrug, benserazide, or a benserazide prodrug, and a suitable amount of a pharmaceutically acceptable vehicle, so as to provide an appropriate form for administration to a patient.

Compositions of the present disclosure may be obtained by conventional procedures using conventional pharmaceutical vehicles, well known in the art.

Pharmaceutical compositions for oral delivery may be in the form of tablets, lozenges, aqueous or oily suspensions, granules, powders, emulsions, capsules, syrups, or elixirs, for example. Orally administered pharmaceutical compositions may contain one or more optional agents, for example, sweetening agents such as fructose, aspartame or saccharin, flavoring agents such as peppermint, oil of wintergreen, or cherry coloring agents and preserving agents, to provide a pharmaceutically palatable preparation. Moreover, in tablet or pill forms, the pharmaceutical compositions may be coated to delay disintegration and absorption in the gastrointestinal tract, thereby providing a sustained action over an extended period of time. Selectively permeable membranes surrounding an osmotically active driving compound are also suitable for orally administered compounds and pharmaceutical compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral pharmaceutical compositions may include standard vehicles such as mannitol, lactose, starch, magnesium stearate, sodium saccharine, cellulose, magnesium carbonate, etc. Such vehicles may be of pharmaceutical grade.

For oral liquid preparations such as suspensions, elixirs and solutions, can include suitable carriers, excipients, or diluents include water, saline, alkylene glycols (e.g., propylene glycol), polyalkylene glycols (e.g., polyethylene glycol) oils, alcohols, slightly acidic buffers from about pH 4 to about pH 6 (e.g., acetate, citrate, ascorbate from about 5 mM to about 50 mM), etc. Additionally, flavoring agents, preservatives, coloring agents, bile salts, acylcarnitines, and the like may be added.

Certain embodiments also include compositions that comprise, as the active ingredient, at least one compound of Formula (I) associated with at least one pharmaceutically acceptable vehicle including excipients, carriers, diluents and/or adjuvants. In forming the compositions, a compound of Formula (I) may be mixed with an excipient, diluted by a diluent or enclosed within a carrier, which can be in the form of a capsule, sachet, paper or other container. When an excipient serves as a diluent, it can be a solid, semi-solid, or liquid material, which can act as a vehicle, carrier, or medium for a compound of Formula (I). Thus, compositions may be in the form of tablets, pills, powders, lozenges, sachets, cachets, elixirs, suspensions, emulsions, solutions, and syrups containing, for example, up to about 90% by weight of a compound of Formula (I) using, for example, soft and hard gelatin capsules.

In preparing a composition, it may be useful to mill a compound of Formula (I) to provide an appropriate particle size prior to combining with other ingredients. The milled particle size of a compound of Formula (I) may be adjusted depending on the aqueous solubility, and in certain embodiments, may be less than about 200 mesh and in certain embodiments, about 40 mesh. Examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methylcellulose. Compositions may additionally include lubricating agents such as talc, magnesium stearate, and mineral oil, wetting agents, emulsifying and suspending agents, preserving agents such as methyl- and propylhydroxy-benzoates, sweetening agents, pH adjusting and buffering agents, toxicity adjusting agents, flavoring agents, and the like. The compositions may be formulated so as to provide quick, sustained, or delayed release of a compound of Formula (I) after administration to the patient by employing procedures known in the art.

A composition may be formulated in unit dosage form, each dosage form comprising an equivalent weight of levodopa ranging from about 1 mg to about 1 g. Unit dosage form refers to a physically discrete unit suitable as a unitary dosage for humans and other mammals, each unit containing a predetermined quantity of active material calculated to produce an intended therapeutic effect, in association with a suitable pharmaceutical excipient, diluent, carrier and/or adjuvant.

Compounds of Formula (I) may be administered to a patient in a therapeutically effective amount. It will be understood, however, that the amount of a compound of Formula (I) actually administered will be determined by a physician, in the light of the relevant circumstances, including the condition to be treated, the chosen route of administration, the actual compound administered, the age, weight, and response of the individual patient, the disease being treated, the severity of the patient's symptoms, and the like.

For preparing solid compositions such as tablets, a compound of Formula (I) may be mixed with a pharmaceutical excipient, diluent, carrier and/or adjuvant to form a solid pre-formulation composition containing a homogeneous mixture containing a compound of Formula (I). When referring to these pre-formulation compositions as homogeneous, it is meant that a compound of Formula (I) is dispersed evenly throughout the composition so that the composition can be readily subdivided into equally effective unit dosage forms such as tablets, pills, or capsules. This solid pre-formulation can then be subdivided into unit dosage forms of the type described herein comprising, for example, an equivalent weight of levodopa ranging from about 1 mg to about 1 g.

Tablets or pills comprising a compound of Formula (I) may be coated or otherwise compounded to provide a dosage form affording the advantage of sustained release. For example, a tablet or pill may comprise an inner dosage and an outer dosage component, the latter being in the form of an envelope over and/or enclosing the former. The two components may be separated by an enteric layer. The enteric layer may serve to resist disintegration in the stomach and permit the inner component to pass intact into the duodenum, or to delay release. A variety of materials may be used for such enteric layers or coatings. For example, such materials include a number of polymeric acids and mixtures of polymeric acids with such materials as shellac, cetyl alcohol, or cellulose acetate.

Liquid dosage forms in which the compositions a compound of Formula (I) may be incorporated for oral administration or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

In certain embodiments, a dosage form can be adapted to be administered to a patient no more than twice per day, and in certain embodiments, only once per day. Dosing may be provided alone or in combination with other drugs and may continue as long as required for effective treatment of the disease, disorder, or condition.

Pharmaceutical compositions comprising at least one compound of Formula (I) may be formulated for immediate release for parenteral administration, oral administration, or by any other appropriate route of administration.

Controlled drug delivery systems can be designed to deliver a drug in such a way that the drug level is maintained within the therapeutic windows and effective and safe blood levels are maintained for a period as long as the system continues to deliver the drug at a particular rate. Controlled drug delivery can produce substantially constant blood levels of a drug as compared to fluctuations observed with immediate release dosage forms. For some drugs, maintaining a constant bloodstream and tissue concentration throughout the course of therapy is the most desirable mode of treatment. Immediate release of these drugs can cause blood levels to peak above the level required to elicit the desired response, which wastes the drug and may cause or exacerbate toxic side effects. Controlled drug delivery can result in optimum therapy, and not only can reduce the frequency of dosing, but may also reduce the severity of side effects. Examples of controlled release dosage forms include dissolution controlled systems, diffusion controlled systems, ion exchange resins, osmotically controlled systems, erodible matrix systems, pH independent formulations, gastric retention systems, and the like.

In certain embodiments, an oral dosage form of the present disclosure can be a controlled release dosage form. Controlled delivery technologies can improve the absorption of a drug in a particular region or regions of the gastrointestinal tract.

The appropriate oral dosage form for a particular pharmaceutical composition of the present disclosure can depend, at least in part, on the gastrointestinal absorption properties of the compound of Formula (I), the stability of the compound of Formula (I) in the gastrointestinal tract, the pharmacokinetics of the compound of Formula (I), and the intended therapeutic profile. An appropriate controlled release oral dosage form can be selected for a particular the compound of Formula (I). For example, gastric retention oral dosage forms can be appropriate for compounds absorbed primarily from the upper gastrointestinal tract, and sustained release oral dosage forms can be appropriate for compounds absorbed primarily form the lower gastrointestinal tract.

Certain compounds are absorbed primarily from the small intestine. In general, compounds traverse the length of the small intestine in about 3 to 5 hours. For compounds that are not easily absorbed by the small intestine or that do not dissolve readily, the window for active agent absorption in the small intestine may be too short to provide a desired therapeutic effect.

Gastric retention dosage forms, i.e., dosage forms that are designed to be retained in the stomach for a prolonged period of time, can increase the bioavailability of drugs that are most readily absorbed by the upper gastrointestinal tract. The residence time of a conventional dosage form in the stomach is about 1 to about 3 hours. After transiting the stomach, there is approximately a 3 to 5 hour window of bioavailability before the dosage form reaches the colon. However, if the dosage form is retained in the stomach, the drug can be released before it reaches the small intestine and will enter the intestine in solution in a state in which it can be more readily absorbed. Another use of gastric retention dosage forms is to improve the bioavailability of a drug that is unstable to the basic conditions of the intestine (see, e.g., Hwang et al., *Critical Reviews in Therapeutic Drug Carrier Systems,* 1998, 15, 243-284).

To enhance drug absorption from the upper gastrointestinal tract, several gastric retention dosage forms have been developed. Examples include, hydrogels (see, e.g., Gutierrez-Rocca et al., U.S. Application Publication No. 2003/0008007), buoyant matrices (see, e.g., Lohray et al., Application Publication No. 2006/0013876), polymer sheets (see, e.g., Mohammad, Application Publication No. 2005/0249798), microcellular foams (see, e.g., Clarke et al., Application Publication No. 2005/0202090), and swellable dosage forms (see, e.g., Edgren et al., U.S. Application Publication No. 2005/0019409; Edgren et al., U.S. Pat. No. 6,797,283; Jacob et al., U.S. Application Publication No. 2006/0045865; Ayres, U.S. Application Publication No. 2004/0219186; Gusler et al., U.S. Pat. No. 6,723,340; Flashner-Barak et al., U.S. Pat. No. 6,476,006; Wong et al., U.S. Pat. Nos. 6,120,803 and 6,548,083; Shell et al., U.S. Pat. No. 6,635,280; and Conte et al., U.S. Pat. No. 5,780,057).

In a swelling and expanding system, dosage forms that swell and change density in relation to the surrounding gastric content may be retained in the stomach for longer than a conventional dosage form. A dosage form can absorb water and swell to form a gelatinous outside surface and float on the surface of gastric content surface while maintaining integrity before releasing a drug. Fatty materials may be added to impede wetting and enhance flotation when hydration and swelling alone are insufficient. Materials that release gases may also be incorporated to reduce the density of a gastric retention dosage form. Swelling also may significantly increase the size of a dosage form and thereby impede discharge of the non-disintegrated swollen solid dosage form through the pylorus into the small intestine. Swellable dosage forms may be formed by encapsulating a core containing drug and a swelling agent, or by combining a drug, swelling agent, and one or more erodible polymers.

Gastric retention dosage forms may also be in the form of a folded thin sheet containing a drug and water-insoluble diffusible polymer that opens in the stomach to its original size and shape, which is sufficiently large to prevent or inhibit passage of the expanded dosage from through the pyloric sphincter.

Floating and buoyancy gastric retention dosage forms may be designed to trap gases within sealed encapsulated cores that can float on the gastric contents, and thereby be retained in the stomach for a longer time, e.g., 9 to 12 hours. Due to the buoyancy effect, these systems can provide a protective layer preventing the reflux of gastric content into the esophageal region and can also be used for controlled release devices. A floating system may, for example, contain hollow cores containing drug coated with a protective membrane. The trapped air in the cores floats the dosage from on the gastric content until the soluble ingredients are released and the system collapses. In other floating systems, cores contain drug and chemical substances capable of generating gases when activated. For example, coated cores, containing carbonate and/or bicarbonate can generate carbon dioxide in the reaction with hydrochloric acid in the stomach or incorporated organic acid in the system. The gas generated by the reaction is retained to float the dosage form. The inflated dosage form later collapses and clears from the stomach when the generated gas permeates slowly through the protective coating.

Bioadhesive polymers can also provide a vehicle for controlled delivery of drugs to a number of mucosal surfaces in addition to the gastric mucosa (see, e.g., Mathiowitz et al., U.S. Pat. No. 6,235,313; and Ilium et al., U.S. Pat. No. 6,207, 197). A bioadhesive system can be designed by incorporation of a drug and other excipients within a bioadhesive polymer. On ingestion, the polymer hydrates and adheres to the mucus membrane of the gastrointestinal tract. Bioadhesive polymers can be selected that adhere to a desired region or regions of the gastrointestinal tract. Bioadhesive polymers may be selected to optimized delivery to targeted regions of the gastrointestinal tract including the stomach and small intestine. The mechanism of the adhesion is thought to be through the formation of electrostatic and hydrogen bonding at the polymer-mucus boundary. Jacob et al., U.S. Application Publication Nos. 2006/0045865 and 2005/0064027 disclose bioadhesive delivery systems which are useful for drug delivery to both the upper and lower gastrointestinal tract.

Ion exchange resins have also been shown to prolong gastric retention, potentially by adhesion.

Gastric retention oral dosage forms may be appropriately used for delivery of drugs that are absorbed mainly from the upper gastrointestinal tract. For example, certain compounds of Formula (I) may exhibit limited colonic absorption, and be absorbed primarily from the upper gastrointestinal tract. Thus, dosage forms that release the compound of Formula (I) in the upper gastrointestinal tract and/or retard transit of the dosage form through the upper gastrointestinal tract will tend to enhance the oral bioavailability of the compound of Formula (I). Other forms comprising a compound of Formula (I) disclosed herein can be appropriately used with gastric retention dosage forms.

Polymer matrices have also been used to achieve controlled release of the drug over a prolonged period of time. Such sustained or controlled release can be achieved by limiting the rate by which the surrounding gastric fluid can diffuse through the matrix and reach the drug, dissolve the drug and diffuse out again with the dissolved drug, or by using a matrix that slowly erodes, continuously exposing fresh drug to the surrounding fluid. Examples of polymer matrices that function by these methods are disclosed, for example, in Skinner, U.S. Pat. Nos. 6,210,710 and 6,217,903; Rencher et al., U.S. Pat. No. 5,451,409; Kim, U.S. Pat. No. 5,945,125; Kim, PCT International Publication No. WO 96/26718; Ayer et al., U.S. Pat. No. 4,915,952; Akhtar et al., U.S. Pat. No. 5,328,942; Fassihi et al., U.S. Pat. No. 5,783,212; Wong et al., U.S. Pat. No. 6,120,803; and Pillay et al., U.S. Pat. No. 6,090,411.

Other drug delivery devices that remain in the stomach for extended periods of time include, for example, hydrogel reservoirs containing particles (Edgren et al., U.S. Pat. No. 4,871,548); swellable hydroxypropylmethylcellulose polymers (Edgren et al., U.S. Pat. No. 4,871,548); planar bioerodible polymers (Caldwell et al., U.S. Pat. No. 4,767,627); plurality of compressible retention arms (Curatolo et al., U.S. Pat. No. 5,443,843); hydrophilic water-swellable, cross-linked polymer particles (Shell, U.S. Pat. No. 5,007,790); and albumin-cross-linked polyvinylpyrrolidone hydrogels (Park et al., *J. Controlled Release* 1992, 19, 131-134).

In certain embodiments, pharmaceutical compositions of the present disclosure may be practiced with a number of different dosage forms, which may be adapted to provide sustained release of the compound of Formula (I) upon oral administration. Sustained release oral dosage forms can be used to release drugs over a prolonged time period and are useful when it is desired that a drug or drug form be delivered to the lower gastrointestinal tract. Sustained release oral dosage forms include diffusion-controlled systems such as reservoir devices and matrix devices, dissolution-controlled systems, osmotic systems, and erosion-controlled systems. Sustained release oral dosage forms and methods of preparing the same are well known in the art (see, for example, "Remington's Pharmaceutical Sciences," Lippincott, Williams & Wilkins, 21st edition, 2005, Chapters 46 and 47; Langer, *Science* 1990, 249, 1527-1533; and Rosoff, "Controlled Release of Drugs," 1989, Chapter 2).

In diffusion-controlled systems, a water-insoluble polymer controls the flow of fluid and the subsequent egress of dissolved drug from the dosage form. Both diffusional and dissolution processes are involved in release of drug from the dosage form. In reservoir devices, a core comprising a drug is coated with the polymer, and in matrix systems, the drug is dispersed throughout the matrix. Cellulose polymers such as ethylcellulose or cellulose acetate can be used in reservoir devices. Examples of materials useful in matrix systems include methacrylates, acrylates, polyethylene, acrylic acid copolymers, polyvinylchloride, high molecular weight polyvinylalcohols, cellulose derivates, and fatty compounds such as fatty acids, glycerides, and carnauba wax.

In dissolution-controlled systems, the rate of dissolution of the drug is controlled by slowly soluble polymers or by microencapsulation. Once the coating is dissolved, the drug becomes available for dissolution. By varying the thickness and/or the composition of the coating or coatings, the rate of drug release can be controlled. In some dissolution-controlled systems, a fraction of the total dose can comprise an immediate-release component. Dissolution-controlled systems include encapsulated/reservoir dissolution systems and matrix dissolution systems. Encapsulated dissolution systems can be prepared by coating particles or granules of drug with slowly soluble polymers of different thickness or by microencapsulation. Examples of coating materials useful in dissolution-controlled systems include gelatin, carnauba wax, shellac, cellulose acetate phthalate, and cellulose acetate butyrate. Matrix dissolution devices can be prepared, for example, by compressing a drug with a slowly soluble polymer carrier into a tablet form.

The rate of release of drug from osmotic pump systems is determined by the inflow of fluid across a semipermeable membrane into a reservoir, which contains an osmotic agent. The drug is either mixed with the agent or is located in a reservoir. The dosage form contains one or more small orifices from which dissolved drug is pumped at a rate determined by the rate of entrance of water due to osmotic pressure. As osmotic pressure within the dosage form increases, the drug is released through the orifice(s). The rate of release is constant and can be controlled within tight limits yielding relatively constant plasma and/or blood concentrations of the drug. Osmotic pump systems can provide a constant release of drug independent of the environment of the gastrointestinal tract. The rate of drug release can be modified by altering the osmotic agent and the sizes of the one or more orifices.

The release of drug from erosion-controlled systems is determined by the erosion rate of a carrier matrix. Drug is dispersed throughout the polymer and the rate of drug release depends on the erosion rate of the polymer. The drug-containing polymer can degrade from the bulk and/or from the surface of the dosage form.

Sustained release oral dosage forms may be in any appropriate form for oral administration, such as, for example, in the form of tablets, pills, or granules. Granules can be filled into capsules, compressed into tablets, or included in a liquid suspension. Sustained release oral dosage forms may additionally include an exterior coating to provide, for example, acid protection, ease of swallowing, flavor, identification, and the like.

In certain embodiments, sustained release oral dosage forms may comprise a therapeutically effective amount of a compound of Formula (I) and a pharmaceutically acceptable vehicle. In certain embodiments, a sustained release oral dosage form may comprise less than a therapeutically effective amount of a compound of Formula (I), and a pharmaceutically effective vehicle. Multiple sustained release oral dosage forms, each dosage form comprising less than a therapeutically effective amount of a compound of Formula (I), may be administered at a single time or over a period of time to provide a therapeutically effective dose or regimen for treating emesis in a patient.

Sustained release oral dosage forms of the present disclosure can release a compound of Formula (I) from the dosage form to facilitate the ability of the compound of Formula (I) to be absorbed from an appropriate region of the gastrointestinal tract, for example, in the small intestine, or in the colon. In certain embodiments, a sustained release oral dosage from may release a compound of Formula (I) from the dosage form over a period of at least about 4 hours, at least about 8 hours, at least about 12 hours, at least about 16 hours, at least about 20 hours, and in certain embodiments, at least about 24 hours. In certain embodiments, a sustained release oral dosage form may release a compound of Formula (I) from the dosage form in a delivery pattern of from about 0 wt % to about 20 wt % in about 0 to about 4 hours, about 20 wt % to about 50 wt % in about 0 to about 8 hours, about 55 wt % to about 85 wt % in about 0 to about 14 hours, and about 80 wt % to about 100 wt % in about 0 to about 24 hours. In certain embodiments, a sustained release oral dosage form may release a compound of Formula (I) from the dosage form in a delivery pattern of from about 0 wt % to about 20 wt % in about 0 to about 4 hours, about 20 wt % to about 50 wt % in about 0 to about 8 hours, about 55 wt % to about 85 wt % in about 0 to about 14 hours, and about 80 wt % to about 100 wt % in about 0 to about 20 hours. In certain embodiments, a sustained release oral dosage form may release a compound of Formula (I) from the dosage form in a delivery pattern of from about 0 wt % to about 20 wt % in about 0 to about 2 hours, about 20 wt % to about 50 wt % in about 0 to about 4 hours, about 55 wt % to about 85 wt % in about 0 to about 7 hours, and about 80 wt % to about 100 wt % in about 0 to about 8 hours.

Sustained release oral dosage forms comprising a compound of Formula (I) may provide a concentration of levodopa in the plasma, blood, or tissue of a patient over time, following oral administration to the patient. The concentration profile of levodopa may exhibit an AUC that is proportional to the dose of the corresponding compound of Formula (I).

Regardless of the specific form of controlled release oral dosage form used, a compound of Formula (I) may be released from an orally administered dosage form over a sufficient period of time to provide prolonged therapeutic concentrations of the compound of Formula (I) in the plasma and/or blood of a patient. Following oral administration, a dosage form comprising a compound of Formula (I) may provide a therapeutically effective concentration of levodopa in the plasma and/or blood of a patient for a continuous time period of at least about 4 hours, of at least about 8 hours, for at least about 12 hours, for at least about 16 hours, and in certain embodiments, for at least about 20 hours following oral administration of the dosage form to the patient. The continuous time periods during which a therapeutically effective concentration of levodopa is maintained may be the same or different. The continuous period of time during which a therapeutically effective plasma concentration of levodopa is maintained may begin shortly after oral administration or after a time interval.

In certain embodiments, an oral dosage for treating or preventing a disease, disorder, or condition in a patient can comprise a compound of Formula (I), wherein the oral dosage form is adapted to provide, after a single administration of the oral dosage form to the patient, a therapeutically effective concentration of levodopa in the plasma of the patient for a first continuous time period selected from at least about 4 hours, at least about 8 hours, at least about 12 hours, and at least about 16 hours, and at least about 20 hours.

An appropriate dose of the pharmaceutical composition may be determined according to any one of several well-established protocols. For example, animal studies, such as studies using mice or rats, may be used to determine an appropriate dose of a pharmaceutical compound. Results from animal studies may be extrapolated to determine doses for use in other species, such as for example, humans. For example, the efficacy of compounds of Formula (I) and compositions thereof for treating Parkinson's disease may be assessed using animal models of Parkinson's disease and clinical studies.

Compounds of Formula (I) or pharmaceutical compositions thereof may be administered as sustained release systems, and in certain embodiments, as orally administered sustained release systems. In certain embodiments, the compounds may be delivered by oral sustained release administration. In certain embodiments, compounds of Formula (I) or pharmaceutical compositions thereof may be administered twice per day, in certain embodiments, once per day, and in certain embodiments at intervals greater than once per day.

Combination Therapy

In certain embodiments, at least one compound of Formula (I) thereof may be used in combination therapy with at least one other therapeutic agent. Pharmaceutical compositions provided by the present disclosure may include, in addition to at least one compound of Formula (I), one or more therapeutic agents effective for treating the same or different disease, disorder, or condition.

Methods provided by the present disclosure include administration of at least one compound of Formula (I) or pharmaceutical compositions thereof and one or more other therapeutic agents, provided that the combined administration does not inhibit the therapeutic efficacy of the at least one compound of Formula (I) or levodopa and/or does not produce adverse combination effects.

Compounds of Formula (I) and another therapeutic agent or agents may act additively or synergistically. In certain embodiments, pharmaceutical compositions provided by the present disclosure can be administered concurrently with the administration of another therapeutic agent, which may be contained in the same pharmaceutical composition as, or in a different composition from that containing at least one compound of Formula (I). In certain embodiments, at least one compound of Formula (I) may be administered prior or subsequent to administration of another therapeutic agent. In certain embodiments of combination therapy, the combination therapy can comprise alternating between administering a composition provided by the present disclosure and a composition comprising another therapeutic agent, e.g., to minimize adverse side effects associated with a particular drug. When a compound of Formula (I) is administered concurrently with another therapeutic agent that can potentially produce adverse side effects including, but not limited to, toxicity, the therapeutic agent may advantageously be administered at a dose that falls below the threshold at which the adverse side effect is elicited.

In certain embodiments, at least one compound of Formula (I) may further be administered together with one or more compounds that enhance, modulate, and/or control the release, bioavailability, therapeutic efficacy, therapeutic potency, and/or stability of the at least one compound of Formula (I) or crystalline form thereof and/or levodopa. For example, to enhance therapeutic efficacy a compound of Formula (I) may be co-administered with one or more active agents to increase the absorption or diffusion of a compound of Formula (I) and/or levodopa through the gastrointestinal tract, or to modify degradation of the (a compound of Formula (I) and/or levodopa in the systemic circulation. In certain embodiments, a compound of Formula (I) may be co-administered with an active agent having pharmacological effects that enhance the therapeutic efficacy of levodopa after being released from the compound of Formula (I). In certain embodiments, a compound of Formula (I) may be co-administered with an active agent having pharmacological effects that enhance the therapeutic efficacy of dopamine after being released from levodopa.

In certain embodiments, a compound of Formula (I) or pharmaceutical compositions comprising a compound of Formula (I) may be administered to a patient together with another compound for treating Parkinson's disease, depression, attention deficit disorder, schizophrenia, manic depression, cognitive impairment disorders, restless legs syndrome, periodic limb movement disorders, tardive dyskinesia, Huntington's disease, Tourette's syndrome, hypertension, addictive disorders, congestive heart failure, stroke, excessive daytime sleepiness, dystonia, memory and learning deficits or loss, and Lewy Body disease.

In certain embodiments, a compound of Formula (I) or a pharmaceutical composition thereof may be administered to a patient for treating Parkinson's disease in combination with a therapy or another therapeutic agent known or believed to be effective in treating Parkinson's disease. Examples of drugs useful for treating Parkinson's disease include amantadine, baclofen, biperiden, benztropine, orphenadrine, procyclidine, trihexyphenidyl, levodopa, carbidopa, andropinirole, apomorphine, benserazide, bromocriptine, budipine, cabergoline, eliprodil, eptastigmine, ergoline, galanthamine, lazabemide, lisuride, mazindol, memantine, mofegiline, pergolide, piribedil, pramipexole, propentofylline, rasagiline, remacemide, ropinirole, selegiline, spheramine, terguride, entacapone, and tolcapone.

In certain embodiments, a compound of Formula (I) or a pharmaceutical composition thereof may be administered to a patient for treating depression in combination with a therapy or another therapeutic agent known or believed to be effective in treating depression. Examples of drugs useful for treating mood disorders such as depression include tricyclic antidepressants such as amitriptyline, amoxapine, clomipramine, desipramine, doxepin, imipramine, maprotiline, nortriptyline, protriptyline, and trimipramine; selective serotonin reuptake inhibitors such as citalopram, escitalopram, fluoxetine, fluvoxamine, paroxetine, and sertraline; serotonin-noradrenaline reuptake inhibitors such as venlafaxine, duloxetine, sibutramine, and milnacipran; monoamine oxidase inhibitors such as phenelzine and tranylcypromine; and psychostimulants such as dextroamphetamine and methylphenidate. Other antidepressants include benmoxine, butriptyline, dosulepin, imipramine, kitanserin, lofepramine, medifoxamine, mianserin, mirtazapine, viloxazine, cotinine, nisoxetine, reboxetine, tianeptine, acetaphenazine, binedaline, brofaromine, cericlamine, clovoxamine, iproniazid, isocarboxazid, moclobemide, phenylhydrazine, selegiline, sibutramine, ademetionine, adrafinil, amesergide, amisulpride, amperozide, benactyzine, bupropion, caroxazone, gepirone, idazoxan, metralindole, minaprine, nefazodone, nomifensine, ritanserin, roxindole, S-adenosylmethionine, escitalopram, tofenacin, trazodone, tryptophan, zalospirone, and Saint John's wort. A compound of Formula (I) or crystalline form thereof and pharmaceutical compositions thereof may also be used in conjunction with psychotherapy or electroconvulsive therapy to treat mood disorders such as depression.

In certain embodiments, a compound of Formula (I) or a pharmaceutical composition thereof may be administered to a patient for treating attention deficit disorder in combination with a therapy or another therapeutic agent known or believed to be effective in treating attention deficit disorder. Examples of drugs useful for treating attention deficit disorder include atomoxetine, bupropion, dexmethylphenidate, dextroamphetamine, methamphetamine, methylphenidate, and pemoline.

In certain embodiments, a compound of Formula (I) or a pharmaceutical composition thereof may be administered to a patient for treating schizophrenia in combination with a therapy or another therapeutic agent known or believed to be effective in treating schizophrenia. Examples of drugs for treating schizophrenia include aripiprazole, loxapine, mesoridazine, quetiapine, reserpine, thioridazine, trifluoperazine, and ziprasidone.

In certain embodiments, a compound of Formula (I) or a pharmaceutical composition thereof may be administered to a patient for treating manic depression in combination with a therapy or another therapeutic agent known or believed to be effective in treating manic depression. Examples of drugs useful for treating manic depression include carbamazepine, clonazepam, clonidine, valproic acid, verapamil, lamotrigine, gabapentin, topiramate, lithium, clozapine, olanzapine, risperidone, quetiapine, ziprasidone, clonazepam, lorazepam, zolipidem, St. John's wort, and omega-3 fatty acids.

In certain embodiments, a compound of Formula (I) or a pharmaceutical composition thereof may be administered to a patient for treating cognitive and memory disorders in combination with a therapy or another therapeutic agent known or believed to be effective in treating cognitive and memory disorders. Examples of drugs useful for treating cognitive or memory disorders include antipsychotic drugs such as chlorpromazine, fluphenazine, haloperidol, loxapine, mesoridazine, molindone, perphenazine, pimozide, thioridazine, thiothixene, trifluoperazine, aripiprazole, clozapine, olanzapine, quetiapine, risperidone, and ziprasidone; sedatives such as diazepam and lorazepam; benzodiazepines such as alprazolam, chlordiazepoxide, clonazepam, clorazepate, diazepam, lorazepam, and oxazepam; nonsteroidal anti-inflammatory drugs such as aceclofenac, acetaminophen, alminoprofen, amfenac, aminopropylon, amixetrine, aspirin, benoxaprofen, bromfenac, bufexamac, carprofen, celecoxib, choline, salicylate, cinchophen, cinmetacin, clopriac, clometacin, diclofenac, diflunisal, etodolac, fenoprofen, flurbiprofen, ibuprofen, indomethacin, indoprofen, ketoprofen, ketorolac, mazipredone, meclofenamate, nabumetone, naproxen, parecoxib, piroxicam, pirprofen, rofecoxib, sulindac, tolfenamate, tolmetin, and valdecoxib; acetylcholinesterase inhibitors such as donepezil, galantamine, rivastigmine, physostigmine, and tacrine; and N-methyl-D-aspartate (NMDA) receptor blockers such as memantine.

In certain embodiments, a compound of Formula (I) or a pharmaceutical composition thereof may be administered to a patient for treating restless legs syndrome in combination with a therapy or another therapeutic agent known or believed to be effective in treating restless legs syndrome. Examples of drugs useful for treating restless legs syndrome include dopaminergics such as levodopa, pergolide mesylate, pramipexole, and rinirole hydrochloride, benzodiazepines such as clonazepam and diazepam, opioids such as codeine, propoxyphene, and oxycodone, and anticonvulsants such as gabapentin, pregabalin, and carbamazepine.

In certain embodiments, compounds of Formula (I) and pharmaceutical compositions thereof may be administered to a patient for treating a movement disorder in combination with a therapy or another therapeutic agent known or believed to be effective in treating a movement disorder. In certain embodiments, a movement disorder is tardive dyskinesia. Examples of drugs useful for treating movement disorders include mild sedatives such as benzodiazepines including alprazolam, chlordiazepoxide, clonazepam, clorazepate, diazepam, lorazepam, and oxazepam; muscle relaxants such as baclofen, anticholinergic drugs such as trihexyphenidyl and diphenhydramine; antipsychotics such as chlorpromazine, fluphenazine, haloperidol, loxapine, mesoridazine, molindone, perphenazine, pimozide, thioridazine, thiothixene, trifluoperazine, aripiprazole, clozapine, olanzapine, quetiapine, risperidone, and ziprasidone; and antidepressants such as amitriptyline. Examples of drugs useful for treating tardive dyskinesia include vitamin E, dizocilpine, memantine, clozapine, lorazepam, diazepam, clonazepam, glycine, D-cycloserine valproic acid, amantadine, ifenprodil, reserpine, and tetrabenazine.

In certain embodiments, a compound of Formula (I) or a pharmaceutical composition thereof may be administered to a patient for treating Huntington's disease in combination with a therapy or another therapeutic agent known or believed to be effective in treating Huntington's disease. Examples of drugs useful for treating Huntington's disease include antipsychotics such as haloperidol, chlorpromazine, and olanzapine; antidepressants such as fluoxetine, sertraline hydrochloride, and nortriptyline; tranquilizers such as benzodiazepines, paroxetine, venlafaxin, and beta-blockers; mood-stabilizers such as lithium, valproate, and carbamazepine; and Botulinum toxin.

In certain embodiments, a compound of Formula (I) or a pharmaceutical composition thereof may be administered to a patient for treating Tourette's syndrome in combination with a therapy or another therapeutic agent known or believed to be effective in treating Tourette's syndrome. Examples of drugs useful for treating Tourette's syndrome include haloperidol, pergolide, and pimozide.

In certain embodiments, a compound of Formula (I) or a pharmaceutical composition thereof may be administered to a patient for treating hypertension in combination with a therapy or another therapeutic agent known or believed to be effective in treating hypertension. Examples of drugs useful for treating hypertension include acebutolol, amiloride, amlodipine, atenolol, benazepril, betaxolol, bisoprolol, candesartan captopril, careolol, carvedilol, chlorothiazide, chlorthalidone, clonidine, diltiazem, doxazosin, enalapril, eplerenone, eprosartan, felodipine, fosinopril, furosemide, guanabenz, guanethidine, guanfacine, hydralazine, hydrochlorothiazide, indapamide, irbesartan, isradipine, labetalol, lisinopril, losartan, methyldopa, metolazone, metoprolol, minoxidil, moexipril, nadolol, nicardipine, nifedipine, nisoldipine, nitroglycerin, olmesartan, perindopril, pindolol, prazosin, propranolol, quinapril, ramipril, reserpine, spironolactone, telmisartan, terazosin, timolol, torsemide, trandolapril, valsartan, and verapamil.

In certain embodiments, a compound of Formula (I) or a pharmaceutical composition thereof may be administered to a patient for treating alcohol addiction and abuse in combination with a therapy or another therapeutic agent known or believed to be effective in treating alcohol addiction and abuse. Examples of drugs useful for treating alcohol addiction or abuse include disulfuram, naltrexone, clonidine, methadone, 1-α-acetylmethadol, buprenorphine, and bupropion.

In certain embodiments, a compound of Formula (I) or a pharmaceutical composition thereof may be administered to a patient for treating narcotic addiction and abuse in combination with a therapy or another therapeutic agent known or believed to be effective in treating narcotic addiction and abuse. Examples of drugs useful for treating narcotic addiction or abuse include buprenorphine, tramadol, methadone, and naltrexone.

In certain embodiments, a compound of Formula (I) or a pharmaceutical composition thereof may be administered to a patient for treating nicotine addiction and abuse in combination with a therapy or another therapeutic agent known or believed to be effective in treating nicotine addiction and abuse. Examples of drugs useful for treating nicotine addiction or abuse include bupropion, clonidine, and nicotine.

In certain embodiments, a compound of Formula (I) or a pharmaceutical composition thereof may be administered to a patient for treating congestive heart failure in combination with a therapy or another therapeutic agent known or believed to be effective in treating congestive heart failure. Examples of drugs useful for treating congestive heart failure include allopurinol, amiloride, amlodipine, benazepril, bisoprolol, carvedilol, digoxin, enalapril, eplerenone, fosinopril, furosemide, hydrochlorothiazide, hydralazine, isosorbide dinitrate, isosorbide mononitrate, lisinopril, metoprolol, moexipril, nesiritide, nicardipine, nifedipine, nitroglycerin, perindopril, prazosin, quinapril, ramipril, spironolactone, torsemide, trandolapril, triamcinolone, and valsartan.

In certain embodiments, a compound of Formula (I) or a pharmaceutical composition thereof may be administered to a patient for treating excessive daytime sleepiness in combination with a therapy or another therapeutic agent known or believed to be effective in treating excessive daytime sleepiness. Examples of drugs useful for treating excessive daytime sleepiness include dextroamphetamine, methylphenidate, modafinil, sodium oxylate, clonidine, bromocriptine, antidepressants, and monoamine oxidase inhibitors.

In certain embodiments, a compound of Formula (I) or a pharmaceutical composition thereof may be administered to a patient for treating dystonia in combination with a therapy or another therapeutic agent known or believed to be effective in treating dystonia. Examples of drugs useful for treating dystonia include Botulinum-toxin, clonazepam, lorazepam, trihexyphenidyl, baclofen, diazepam, tetrabenazine, cyclobenzaprine, carbamazepine, and benzatropine.

EXAMPLES

The invention is further defined by reference to the following examples, which describe synthesis, properties, and uses of levodopa dimethyl-substituted diester prodrugs of Formula (I). It will be apparent to those skilled in the art that many modifications, both to materials and methods, may be practiced without departing from the scope of the disclosure.

Example 1

(1R,2R)-1-Methyl-2-phenylcarbonyloxypropyl (2S)-2-Amino-3-(3,4-dihydroxyphenyl)propanoate Hydrochloride (1)

Step A: (1R,2R)-2-Hydroxy-1-methylpropyl (2S)-2-[(tert-Butoxy)carbonylamino]-3-[3,4-bis(phenylmethoxy)phenyl]propanoate N-Boc-L-DOPA(OBn)$_2$COOH (4.3 g, 9 mmol) was dissolved in anhydrous dichloromethane. Triethylamine (3 mL, 22 mmol), and 2,4,6-trichlorobenzoyl chloride (1.7 mL, 11 mmol) were added and the solution stirred for 30 min. A solution of (2R,3R-(−)-2,3-butanediol (1.0 mL, 11 mmol) in dichloromethane was slowly added to the reaction mixture followed by a catalytic amount of 4-(dimethylamino)pyridine. The mixture was stirred at room temperature for 16 h, then washed with 10% citric acid, 5% NaHCO$_3$, brine, and dried over Na$_2$SO$_4$. After removing the solvent, chromatography (silica gel, gradient of 20%-30% ethyl acetate in hexane) of the residue afforded 3.4 g (69% yield) of (1R,2R)-2-hydroxy-1-methylpropyl (2S)-2-[(tert-butoxy)carbonylamino]-3-[3,4-bis(phenylmethoxy)phenyl]propanoate. $^1$H NMR (400 MHz, CDCl$_3$): δ 1.08 (d, J=6.4 Hz, 3H), 1.11 (d, J=6.4 Hz, 3H), 1.41 (s, 9H), 2.96 (m, 2H), 3.66 (s, br, 1H), 4.34 (m, 1H), 4.75 (m, 1H), 4.98 (m, 1H), 5.10 (s, 4H), 6.66 (d, J=8 Hz, 1H), 6.77 (s, 1H), 6.82 (d, J=8 Hz, 1H), 7.26-7.41 (m, 10H).

Step B: (1R,2R)-1-Methyl-2-phenylcarbonyloxypropyl (2S)-2-[(tert-Butoxy)carbonylamino]-3-[3,4-bis(phenylmethoxy)phenyl]propanoate To a solution of benzoic acid (0.57 g, 4.8 mmol) in anhydrous dichloromethane was added triethylamine (1.7 mL, 12 mmol) and 2,4,6-trichlorobenzoyl chloride (0.9 mL, 5.76 mmol). The mixture was stirred for 30 min and a solution of (1R,2R)-2-hydroxy-1-methylpropyl (2S)-2-[(tert-butoxy)carbonylamino]-3-[3,4-bis(phenylmethoxy)phenyl]propanoate (2.4 g, 4.4 mmol) in dichloromethane was slowly added to the reaction mixture, followed by the addition of a catalytic amount of 4-(dimethylamino)pyridine. The mixture was stirred at room temperature for 16 h, washed with 10% citric acid, dried over Na$_2$SO$_4$, and concentrated. Chromatography (silica gel, 20% ethyl acetate in hexane) of the residue afforded 2.6 g (90% yield) of (1R,2R)-1-methyl-2-phenylcarbonyloxypropyl (2S)-2-[(tert-butoxy)carbonylamino]-3-[3,4-bis(phenylmethoxy)phenyl]propanoate. $^1$H NMR (400 MHz, CDCl$_3$): δ 1.26 (d, J=6.4 Hz, 6H), 1.39 (s, 9H), 2.78 (m, 1H), 2.96 (m, 1H), 4.51 (m, 1H), 4.89 (d, 1H), 5.10 (s, 4H), 5.15 (m, 1H), 6.57 (d, J=8 Hz, 1H), 6.71 (s, 1H), 6.77 (d, J=8 Hz, 1H), 7.25-7.43 (m, 12H), 7.52 (t, J=7.6 Hz, 1H), 7.99 (d, J=7.6 Hz, 2H).

Step C: (1R,2R)-1-Methyl-2-phenylcarbonyloxypropyl (2S)-3-(3,4-Dihydroxyphenyl)-2-[(tert-butoxy)carbonylamino]propanoate 200 mg of 10% Pd—C pre-mixed with 10 mL of methanol was added to a solution of (1R,2R)-1-methyl-2-phenylcarbonyloxypropyl (2S)-2-[(tert-butoxy)carbonylamino]-3-[3,4-bis(phenylmethoxy)phenyl]propanoate (2.6 g, 3.9 mmol) in 40 mL of tetrahydrofuran under a nitrogen atmosphere. The nitrogen was exchanged with hydrogen and the mixture stirred under hydrogen at room temperature for 2 h. After filtration and washing with methanol, the filtrate was concentrated and chromatography (silica gel, 30% ethyl acetate in hexane) of the residue afforded 1.8 g (95% yield) of (1R,2R)-1-methyl-2-phenylcarbonyloxypropyl (2S)-3-(3,4-dihydroxyphenyl)-2-[(tert-butoxy)carbonylamino]propanoate. MS (ESI) m/z 474.31 (M+H)$^+$ and 472.18 (M−H)$^−$.

Step D: (1R,2R)-1-Methyl-2-phenylcarbonyloxypropyl (2S)-2-Amino-3-(3,4-dihydroxyphenyl)propanoate Hydrochloride (1)

(1R,2R)-1-Methyl-2-phenylcarbonyloxypropyl (2S)-3-(3,4-dihydroxyphenyl)-2-[(tert-butoxy)carbonylamino]propanoate (1.8 g, 2.7 mmol) was dissolved in 40 mL of 4M HCl in dioxane. The mixture was stirred at room temperature for 30 min. The dioxane was evaporated completely under reduced pressure. The resulting white solid was dissolved in acetonitrile (5 mL) and ether added until the solution became slightly cloudy. The solution was refrigerated overnight and the product crystallized. The white, crystalline solid was collected and dried under vacuum to afford 1.0 g (87% yield) of the title compound (1). $^1$H NMR (400 MHz, CD$_3$OD): δ 1.12 (d, J=6 Hz, 3H), 1.24 (d, J=6 Hz, 3H), 2.85 (dd, J=14, 8 Hz, 1H), 3.02 (dd, J=14, 5.2 Hz, 1H), 4.15 (t, J=5.6 Hz, 1H), 5.06 (m, 2H), 6.46 (dd, J=8, 2 Hz, 1H), 6.61 (d, J=2 Hz, 1H), 6.65 (d, J=8 Hz, 1H), 7.54 (t, J=7.6 Hz, 2H), 7.65 (t, J=7.6 Hz, 1H), 7.90 (m, 2H). MS (ESI) m/z 374.11 (M+H)$^+$ and 372.08 (M−H)$^−$.

Example 2

(1S,2S)-1-Methyl-2-phenylcarbonyloxypropyl (2S)-2-Amino-3-(3,4-dihydroxyphenyl)propanoate Hydrochloride (2)

Following the procedure described in Example 1 and substituting (2R,3R)-(−)-2,3-butanoldiol with (2S,3S)-(+)-2,3-butanediol in Step A provided the title compound (2) (34% yield over 4 steps) as a white solid. $^1$H NMR (400 MHz, CD$_3$OD): δ 1.30 (d, J=6 Hz, 3H), 1.34 (d, J=6 Hz, 3H), 2.68 (dd, J=14.4, 8 Hz, 1H), 2.94 (dd, J=14.4, 6 Hz, 1H), 4.01 (dd, J=8, 5.6 Hz, 1H), 5.20 (m, 2H), 6.44 (dd, J=8, 2 Hz, 1H), 6.59 (d, J=2 Hz, 1H), 6.66 (d, J=8 Hz, 1H), 7.46 (t, J=7.6 Hz, 2H), 7.59 (t, J=7.6 Hz, 1H), 7.99 (m, 2H). MS (ESI) m/z 374.16 (M+H)$^+$ and 372.08 (M−H)$^−$.

Example 3

(1R,2R)-1-Methyl-2-(4-fluorophenylcarbonyloxy)propyl (2S)-2-Amino-3-(3,4-dihydroxyphenyl)propanoate Hydrochloride (3)

Following the procedure described in Example 1 and substituting benzoic acid with 4-fluorobenzoic acid in Step B provided the title compound (3) (42% yield over 4 steps) as a white solid. $^1$H NMR (400 MHz, CD$_3$OD): δ 1.24 (d, J=6.4 Hz, 3H), 1.32 (d, J=6.4 Hz, 3H), 3.06 (d, J=6.4 Hz, 2H), 4.21 (t, J=6.8 Hz, 1H), 5.19 (m, 2H), 6.57 (dd, J=8, 2 Hz, 1H), 6.71 (d, J=2 Hz, 1H), 6.74 (d, J=8 Hz, 1H), 7.24 (t, J=8.8 Hz, 2H), 8.02 (dd, J=8.8, 5.2 Hz, 2H). MS (ESI) m/z 392.20 (M+H)$^+$ and 390.15 (M−H)$^−$.

Example 4

(1S,2S)-1-Methyl-2-(4-fluorophenylcarbonyloxy)propyl (2S)-2-Amino-3-(3,4-dihydroxyphenyl)propanoate Hydrochloride (4)

Following the procedure described in Example 1 substituting benzoic acid with 4-fluorobenzoic acid in Step B and (2R,3R)-(−)-2,3-butanediol with (2S,3S)-(+)-2,3-butanediol in Step A provided the title compound (4) (47% yield over 4 steps) as a white solid. $^1$H NMR (400 MHz, CD$_3$OD): δ 1.32 (d, J=6 Hz, 3H), 1.36 (d, J=6 Hz, 3H), 2.75 (dd, J=14.4, 8 Hz, 1H), 3.02 (dd, J=14.4, 5.6 Hz, 1H), 4.22 (dd, J=8, 6 Hz, 1H), 5.23 (m, 1H), 6.46 (dd, J=8, 2 Hz, 1H), 6.61 (d, J=2 Hz, 1H), 6.68 (d, J=8 Hz, 1H), 7.19 (t, J=8.4 Hz, 2H), 8.05 (dd, J=8.4, 5.2 Hz, 2H). MS (ESI) m/z 392.15 (M+H)$^+$ and 390.10 (M−H)$^−$.

Example 5

(1R,2R)-2-Acetyloxy-1-methylpropyl (2S)-2-Amino-3-(3,4-dihydroxyphenyl)propanoate Hydrochloride (5)

Step A: (1R,2R)-2-Hydroxy-1-methylpropyl (2S)-2-[(tert-Butoxy)carbonylamino]-3-[3,4-bis(phenylmethoxy)phenyl]propanoate (6)

N-Boc-L-DOPA(OBn)$_2$COOH (21.8 g, 45.8 mmol), (2R, 3R)-(−)-2,3-butanediol (5 g, 55 mmol), and dicyclohexylcarbodiimide (DCC) were dissolved in anhydrous dichloromethane. A catalytic amount of 4-(dimethylamino)pyridine was added to the solution. The resulting mixture was stirred at room temperature for 16 hours. After filtration, the filtrate was washed with 10% citric acid, 5% sodium bicarbonate, and brine. The organic layer was collected, dried over Na$_2$SO$_4$, and concentrated. Chromatography (silica gel, 10% ethyl acetate in hexane) gave 16.7 g (67% yield) of the title compound (6). $^1$H NMR (400 MHz, CDCl$_3$): δ 1.05 (d, J=6.4 Hz, 3H), 1.13 (d, J=6.4 Hz, 3H), 1.43 (s, 9H), 2.68 (s, 1H, br), 2.94 (dd, J=14.0, 6.8 Hz, 1H), 2.99 (dd, J=14, 6.8 Hz, 1H), 3.67 (m, 1H), 4.34 (dd, 1H, J=13.2, 6.8 Hz, 1H), 4.98 (m, 1H), 5.05 (d, J=6.8 Hz, 1H, NH), 5.13 (s, 4H), 6.68 (d, J=8.0 Hz, 1H), 6.79 (s, 1H), 6.85 (d, J=8.0 Hz, 1H), 7.26-7.43 (m, 10H).

Step B: (1R,2R)-2-Acetyloxy-1-methylpropyl (2S)-2-[(tert-Butoxy)carbonylamino]-3-[3,4-bis(phenylmethoxy)phenyl]propanoate (7)

Acetyl chloride (0.39 mL, 5.5 mmol) and (1R,2R)-2-hydroxy-1-methylpropyl (2S)-2-[(tert-butoxy)carbonylamino]-3-[3,4-bis(phenylmethoxy)phenyl]propanoate (6) (2.0 g, 3.6 mmol) were dissolved in 25 mL of anhydrous dichloromethane. A solution of pyridine (0.5 mL, 5.5 mmol) in dichloromethane was added dropwise at 0° C. The mixture was stirred at room temperature for 2 h. The product was extracted with dichloromethane, washed with 5% NaHCO$_3$, 10% citric acid, and dried over Na$_2$SO$_4$. After concentration and drying under vacuum, the crude product (7) (2.0 g, 95% yield) was isolated and used in the next reaction without further purification. $^1$H NMR (400 MHz, CDCl$_3$): δ 1.11 (d, J=6.4 Hz, 3H), 1.15 (d, J=6.4 Hz, 3H), 1.43 (s, 9H), 2.05 (s, 3H), 2.95 (dd, J=13.6, 6.4 Hz, 1H), 3.00 (dd, J=13.6, 6.4 Hz, 1H), 4.50 (dd, J=13.6, 6.4 Hz, 1H), 4.93 (m, 2H), 4.98 (d, 1H, NH), 5.12 (s, 4H), 6.66 (dd, J=8.0, 2.0 Hz, 1H), 6.77 (d, J=2.0 Hz, 1H), 6.84 (d, J=8.0 Hz, 1H), 7.29-7.45 (m, 10H).

Step C: (1R,2R)-2-Acetyloxy-1-methylpropyl (2S)-3-(3,4-Dihydroxyphenyl)-2-[(tert-butoxy)carbonylamino]propanoate (8)

To a solution of (1R,2R)-2-acetyloxy-1-methylpropyl (2S)-2-[(tert-butoxy)carbonylamino]-3-[3,4-bis(phenylmethoxy)phenyl]propanoate (7) (2.0 g, 3.4 mmol) in 20 mL of methanol, 10% Pd—C (100 mg) pre-mixed with 10 mL of methanol was added under nitrogen atmosphere. The nitrogen was exchanged with hydrogen and the mixture stirred under the hydrogen atmosphere at room temperature for 4 h. After filtration and washing with methanol, the filtrate was concentrated to provide 1.4 g (100% yield) of the title compound (8). $^1$H NMR (400 MHz, CDCl$_3$): δ 1.14 (d, J=6.4 Hz, 3H), 1.16 (d, J=6.4 Hz, 3H), 1.42 (s, 9H), 2.06 (s, 3H), 2.92 (dd, J=12.8, 6.4 Hz, 1H), 2.96 (dd, J=12.8, 6.4 Hz, 1H), 4.46 (dd, J=12.4, 6.4 Hz, 1H), 4.95 (m, 2H), 5.05 (d, J=8.8 Hz, 1H, NH), 6.65 (d, J=8.0 Hz, 1H), 6.66 (s, 1H), 6.73 (d, J=8.0 Hz, 1H). MS (ESI) m/z 434.1 (M+Na)$^+$ and 410.1 (M−H)$^−$.

Step D: (1R,2R)-2-Acetoxy-1-methylpropyl (2S)-2-Amino-3-(3,4-dihydroxyphenyl)propanoate Hydrochloride (5)

(1R,2R)-2-Acetyloxy-1-methylpropyl (2S)-3-(3,4-dihydroxyphenyl)-2-[(tert-butoxy)carbonylamino]propanoate (8) (0.4 g, 0.97 mmol) was dissolved in 8 mL of 4M HCl in 1,4-dioxane. The resulting mixture was stirred at room temperature for 60 min. After removing dioxane, acetonitrile (5 mL) was added. The title compound (5) (0.16 g, 53% yield) was crystallized and collected by filtration. $^1$H NMR (400 MHz, CD$_3$OD): δ 1.19 (d, J=6.4 Hz, 3H), 1.21 (d, J=6.4 Hz, 3H), 2.04 (s, 3H), 3.02 (dd, J=12.0, 6.4 Hz, 1H), 3.07 (dd, J=12.0, 6.4 Hz, 1H), 4.21 (t, J=6.4 Hz, 1H), 4.95 (m, 1H), 5.04 (m, 1H), 6.57 (dd, J=8.0, 2.0 Hz, 1H), 6.67 (d, J=2.0 Hz, 1H), 6.74 (d, J=8.0 Hz, 1H). MS (ESI) m/z 312.2 (M+H)$^+$ and 310.2 (M−H)$^−$.

Example 6

(1R,2R)-1-Methyl-2-(2-methylpropanoyloxy)propyl (2S)-2-Amino-3-(3,4-dihydroxyphenyl)propanoate Hydrochloride (9)

Following the procedure of Example 5 and substituting acetyl chloride with iso-butyryl chloride in Step B provided the title compound (9) (45.6% yield over 4 steps) as a white solid. m.p.: 164.9-166.4° C. $^1$H NMR (400 MHz, CD$_3$OD): δ 1.15 (d, J=6.8 Hz, 3H), 1.16 (d, J=6.8 Hz, 3H), 1.18 (d, J=6.8 Hz, 3H), 1.19 (d, J=6.4 Hz, 3H), 2.55 (m, 1H, J=6.8 Hz), 3.03 (dd, J=12.4, 6.8 Hz, 1H), 3.07 (dd, J=14.4, 6.8 Hz, 1H), 4.20 (t, J=6.8 Hz, 1H), 4.96 (m, 1H), 5.05 (m, 1H), 6.57 (dd, J=8.0, 2.0 Hz, 1H), 6.67 (d, J=2.0 Hz, 1H), 6.74 (d, J=8.0 Hz, 1H). MS (ESI) m/z 340.1 (M+H)$^+$ and 338.1 (M−H)$^−$. Calc. For C$_{17}$H$_{26}$NO$_6$Cl: C, 54.33; H, 6.97; N, 3.73. Found: C, 54.42; H, 6.77; N, 3.66.

Example 7

(1R,2R)-1-Methyl-2-(2-methylpropanoyloxy)propyl (2S)-2-Amino-3-(3,4-dihydroxyphenyl)propanoate Mesylate (10)

The mother liquor from the crystallization of (1R,2R)-1-methyl-2-(2-methylpropanoyloxy)propyl (2S)-2-amino-3-(3,4-dihydroxyphenyl)-propanoate, hydrochloride salt (9) was concentrated to an oil and partitioned between saturated NaHCO$_3$ (50 mL) and ethyl acetate (200 mL). The organic layer was separated, washed with brined, dried over Na$_2$SO$_4$, and concentrated. The residue was dissolved in acetonitrile (25 mL). Methanesulfonic acid (1.0 mL) was added and the mixture was stirred for one hour at room temperature. The white solid was collected by filtration and dried under high vacuum to provide the title compound (10) (1.1 g). m.p.: 181.2-186.0° C. $^1$H NMR (400 MHz, CD$_3$OD): δ 1.15 (d, J=6.8 Hz, 3H), 1.16 (d, J=6.8 Hz, 3H), 1.19 (d, J=6.4 Hz, 3H), 1.20 (d, J=6.8 Hz, 3H), 2.56 (m, 1H), 2.72 (s, 3H), 3.05 (dd, J=14.4, 7.2 Hz, 1H), 3.06 (dd, J=14.4, 7.2 Hz, 1H), 4.20 (t, J=7.2 Hz, 1H), 4.96 (m, 1H), 5.05 (m, 1H), 6.56 (dd, J=8.0, 2.0 Hz, 1H), 6.67 (d, J=2.0 Hz, 1H), 6.74 (d, J=8.0 Hz, 1H). MS (ESI) m/z 340.1 (M+H)$^+$ and 338.1 (M−H)$^−$.

Example 8

(1R,2R)-1-Methyl-2-phenylcarbonyloxypropyl (2S)-2-Amino-3-(3,4-dihydroxyphenyl)propanoate Mesylate (11)

(1R,2R)-1-Methyl-2-phenylcarbonyloxypropyl (2S)-2-amino-3-(3,4-dihydroxyphenyl)propanoate hydrochloride (1) (0.3 g, 0.7 mmol) was neutralized with 5% sodium bicarbonate at about 0° C. The product was extracted with ethyl acetate and dried over MgSO$_4$. After filtration, methane sulfonic acid (47.0 μL, 0.7 mmol) was added to the filtrate. The mixture was stirred at room temperature and the title compound (12) (0.3 g, 97% yield) was crystallized and collected by filtration. m.p.: 94.4° C. (dec.). $^1$H NMR (400 MHz, CD$_3$OD): δ 1.28 (d, J=6.4 Hz, 3H), 1.33 (d, J=6.4 Hz, 3H), 2.70 (s, 3H), 3.02 (dd, J=12.4, 4.4 Hz, 1H), 3.07 (dd, J=12.4, 4.4 Hz, 1H), 4.18 (t, J=6.8 Hz, 1H), 5.12 (m, 2H), 6.56 (dd, J=8.0, 2.0 Hz, 1H), 6.68 (d, J=2.0 Hz, 1H), 6.73 (d, J=8.0 Hz, 1H), 7.49 (t, J=7.6 Hz, 2H), 7.61 (t, J=7.6 Hz, 1H), 7.98 (m, 2H). MS (ESI) m/z 374.1 (M+H)$^+$ and 372.1 (M−H)$^−$.

Example 9

(1R,2R)-2-Ethoxycarbonyloxy-1-methylpropyl (2S)-2-Amino-3-(3,4-dihydroxyphenyl)propanoate Hydrochloride (12)

Following the procedure of Example 5 and substituting acetyl chloride with ethyl chloroformate in Step B provided the title compound (12) (48% yield over 4 steps) as a white solid. $^1$H NMR (400 MHz, CDCl$_3$): δ 1.24-1.34 (m, 9H), 3.02-3.13 (m, 2H), 4.16-4.25 (m, 3H), 4.84 (m, 1H), 5.10 (m, 1H), 6.60 (m, 1H), 6.70 (m, 1H), 6.77 (m, 1H).

Example 10

(1R,2R)-1-Methyl-2-(2-methylpropoxycarbonyloxy)propyl (2S)-2-Amino-3-(3,4-dihydroxyphenyl)propanoate Hydrochloride (13)

Following the procedure of Example 5 and substituting acetyl chloride with isobutyl chloroformate in Step B provided the title compound (13) (45% yield over 4 steps) as a white solid. $^1$H NMR (400 MHz, CDCl$_3$ plus drops of CD$_3$OD): δ 0.91 (d, J=6.8 Hz, 3H), 1.24 (d, J=6.4 Hz, 3H), 1.27 (d, J=6.4 Hz, 3H), 1.94 (hept. J=6.8 Hz, 1H), 3.03 (dd, J=14.4, 7.2 Hz, 1H), 3.18 (dd, J=14.4, 5.0 Hz, 1H), 3.89 (m, 2H), 4.09 (dd, J=6.8, 5.2 Hz, 1H), 4.79 (m, 1H), 5.05 (m, 1H), 6.49 (dd, J=8.0, 2.0 Hz, 1H), 6.73 (d, J=8.0 Hz, 1H), 6.82 (d, J=2.0 Hz, 1H).

Example 11

(1R,2R)-1-Methyl-2-pentyloxycarbonyloxypropyl (2S)-2-Amino-3-(3,4-dihydroxyphenyl)propanoate Hydrochloride (14)

Following the procedure of Example 5 and substituting acetyl chloride with pentyl chloroformate in Step B provided the title compound (14) (40% yield over 4 steps) as a white solid. $^1$H NMR (400 MHz, CD$_3$OD): δ 0.93 (m, 3H), 1.23 (d, J=6.4 Hz, 3H), 1.24 (d, J=6.4 Hz, 3H), 1.37 (m, 4H), 1.68 (m, 2H), 3.00 (dd, J=14.4, 7.6 Hz, 1H), 3.09 (dd, J=14.4, 6.4 Hz, 1H), 4.12 (m, 2H), 4.20 (m., 1H), 4.82 (m, 1H), 5.07 (m, 1H), 6.57 (dd, J=8.0, 2.0 Hz, 1H), 6.68 (d, J=2.0 Hz, 1H), 6.74 (d, J=8.0 Hz, 1H).

Example 12

Alternative Method of Synthesizing (1R,2R)-1-Methyl-2-(2-methylpropanoyloxy)propyl (2S)-2-Amino-3-(3,4-dihydroxyphenyl)propanoate (9)

Step A: (1R,2R)-2-Hydroxy-1-methylpropyl 2-methylpropanoate (15)

To a mixture of isobutyryl chloride (5.03 mL, 47.5 mmol) and (2R,3R)-(−) 2,3-butanediol (4.5 g, 50 mmol) in anhydrous dichloromethane (350 mL), a solution of pyridine (4.86 ml, 60 mmol) in anhydrous dichloromethane (150 mL) was added dropwise at −10° C. The resulting reaction mixture was stirred at −10° C. to room temperature for 16 hours. The product was extracted with dichloromethane and washed with 10% citric acid (200 mL×2), 5% sodium bicarbonate (200 mL×2), and brine (200 mL). The organic layer was collected and dried over MgSO$_4$. Concentration gave 7.6 g of crude product, which contained 18% of di-ester as a side product. The crude product (15) was used in next reaction without further purification. $^1$H NMR (400 MHz, CDCl$_3$): δ 1.14-1.21 (m, 12H), 1.98 (s, br, 1H, OH), 2.56 (m, 1H, J=6.8 Hz), 3.74 (m, 1H, J=6.8 Hz), 4.74 (m, 1H, J=6.8 Hz).

Step B: (2S)-2-[(tert-Butoxy)carbonylamino]-3-(2-oxobenzo[3,4-d]1,3-dioxolen-5-yl)propanoic Acid (16)

Boc-L-DOPA (22.3 g, 75 mmol) and disuccinimidyl carbonate (DSC, 80% pure, 24 g, 75 mmol) were suspended in anhydrous dichloromethane (500 mL) and triethylamine (21 mL, 150 mmol) was added dropwise at 0° C. The resulting reaction mixture was stirred at 0° C. for 30 min. The suspension became a clear solution. HPLC indicated a completed reaction. The reaction mixture was washed with 10% citric acid (200 mL) and water (200 mL×5) to remove triethylamine and N-hydroxysuccinamide. The organic layer was collected, dried over MgSO$_4$, and concentrated to provide the title compound (16) (22 g, 91% yield). $^1$H NMR (400 MHz, CDCl$_3$): δ 1.43 (s, 9H), 3.11 (dd, 1H, J=14, 6.8 Hz), 3.27 (dd, 1H, J=14, 6.8 Hz), 4.59 (dd, 1H, J=14, 6.8 Hz), 5.03 (d, 1H, NH, J=8.0 Hz), 7.05 (dd, 1H, J=8, 2 Hz), 7.11 (d, 1H, J=2 Hz), 7.18 (d, 1H, J=8 Hz). MS (ESI) m/z 321.9 (M−H)$^−$.

Step C: (1R,2R)-1-Methyl-2-(2-methylpropanoyloxy)propyl (2S)-2-[(tert-Butoxy)carbonylamino]-3-(2-oxobenzo[3,4-d]1,3-dioxolen-5-yl)propanoate (17)

To a mixture of (2S)-2-[(tert-butoxy)carbonylamino]-3-(2-oxobenzo[3,4-d]1,3-dioxolen-5-yl)propanoic acid (16) (5.86 g, 18.1 mmol) and (1R,2R)-2-hydroxy-1-methylpropyl 2-methylpropanoate (15) (4.15 g, 21.84 mmol) in anhydrous dichloromethane (40 mL), a solution of dicyclohexylcarbodiimide (5.62 g, 27.3 mmol) in anhydrous dichloromethane (10 mL) was added dropwise at 0° C. To the solution, a catalytic amount of 4-(dimethylamino)pyridine was added.

The resulting mixture was stirred at 0° C. for 30 min, then at room temperature for 2 hours. TLC indicated a completed reaction. The side product, dicyclohexylurea, was removed by filtration. The filtrate was diluted with dichloromethane (100 mL) and washed with 10% citric acid and water. The organic layer was collected, dried over MgSO$_4$, and concentrated to provide the title compound (17) (6.4 g, 76% yield). MS (ESI) m/z 465.9 (M+H)$^+$.

Step D: (1R,2R)-1-Methyl-2-(2-methylpropanoyloxy)propyl (2S)-3-(3,4-Dihydroxyphenyl-2-[(tert-butoxy)carbonylamino]propanoate (18)

(1R,2R)-1-Methyl-2-(2-methylpropanoyloxy)propyl (2S)-2-[(tert-butoxy)carbonylamino]-3-(2-oxobenzo[3,4-d]1,3-dioxolen-5-yl)propanoate (17) (6.4 g, 13.83 mmol) was dissolved in 50 mL of mixture of sat. sodium bicarbonate and acetonitrile (1:1). The resulting mixture was stirred at 60° C. under nitrogen for 60 min. TLC indicated a completed reaction. Acetonitrile was removed under reduced pressure. The product was extracted with methyl tert-butyl ether. The organic layer was collected, washed with 10% citric acid, dried over MgSO$_4$, and concentrated to provide the title compound (18) (6.7 g, 100% yield). $^1$H NMR (400 MHz, CDCl$_3$): δ 1.13-1.16 (m, 12H), 1.42 (s, 9H), 2.54 (m, 1H, J=7.2 Hz), 2.94 (d, 2H, J=6.0 Hz), 4.47 (dd, 1H, J=6.8, 14 Hz), 4.91 (m, 1H), 4.97 (m, 1H), 5.02 (d, 1H, NH, J=8.4 Hz), 6.53 (dd, 1H, J=2, 8 Hz), 6.66 (d, 1H, J=2 Hz), 6.74 (d, 1H, J=8 Hz). MS (ESI) m/z 439.9 (M+H)$^+$.

Step E: (1R,2R)-1-Methyl-2-(2-methylpropanoyloxy)propyl (2S)-2-Amino-3-(3,4-dihydroxyphenyl)propanoate (9)

(1R,2R)-1-Methyl-2-(2-methylpropanoyloxy)propyl (2S)-3-(3,4-dihydroxyphenyl)-2-[(tert-butoxy)carbonylamino]propanoate (18) (6.7 g, 15 mmol) was dissolved in 20 ml of 4M HCl in 1,4-dioxane. The resulting mixture was stirred at room temperature for 60 min. dioxane and then evaporated completely under reduced pressure. The residue was dissolved in acetonitrile (20 mL). The solution was stirred at room temperature. The product was crystallized as hydrogen chloride salt, which was collected by filtration and dried under vacuum to give the title compound (9) (4.1 g, 75% yield). m.p.: 164.7-166.2° C. $^1$H NMR (400 MHz, CD$_3$OD): δ 1.15 (d, 3H, J=6.8 Hz), 1.16 (d, 3H, J=6.8 Hz), 1.18 (d, 3H, J=6.8 Hz), 1.19 (d, 3H, J=6.4 Hz), 2.55 (m, 1H, J=6.8 Hz), 3.03 (dd, 1H, J=12.4, 6.8 Hz), 3.07 (dd, 1H, J=14.4, 6.8 Hz), 4.20 (t, 1H, J=6.8 Hz), 4.96 (m, 1H), 5.05 (m, 1H), 6.57 (dd, 1H, J=2, 8 Hz), 6.67 (d, 1H, J=2 Hz), 6.74 (d, 1H, J=8 Hz). MS (ESI) m/z 340.1 (M+H)$^+$ and 338.1 (M−H), de>98% (by HPLC on Chiralpak column).

Example 13

Crystallization of (1R,2R)-1-Methyl-2-(2-methylpropanoyloxy)propyl (2S)-2-Amino-3-(3,4-dihydroxyphenyl)propanoate Hydrochloride (9)

Crystallization of (1R,2R)-1-methyl-2-(2-methylpropanoyloxy)propyl (2S)-2-amino-3-(3,4-dihydroxyphenyl)propanoate hydrochloride (9) was crystallized using the solvents listed in Table 1 on an 80 mg scale. Differential scanning calorimetry (DCS) and X-ray powder diffraction (XRPD) analyses indicated that crystalline (1R,2R)-1-methyl-2-(2-methylpropanoyloxy)propyl (2S)-2-amino-3-(3,4-dihydroxyphenyl)propanoate hydrochloride salt prepared from these solvents have the same polymorph. The properties are summarized in Table 1.

TABLE 1

Properties of crystalline (1R,2R)-1-methyl-2-(2-methylpropanoyloxy)propyl (2S)-2-amino-3-(3,4-dihydroxyphenyl)propanoate hydrochloride (9) crystallized from various solvents.

| Solvents | m.p. (° C.) | Melting peak on DSC (° C.) | ΔH (g/J) | Hygro-scopicity | XRPD 2θ (deg) |
|---|---|---|---|---|---|
| Acetonitrile | 165.6-167.6 | 168.07 | 88.23 | None | 13.7, 14.8, 16.1, 17.9, 18.4, 19.0, 21.3, 21.8, 24.1, 24.9, 26.3, 27.1 |
| Tetrahydrofuran-diisopropyl ether | 166.5-168.0 | 167.88 | 89.77 | None | 13.7, 14.8, 16.1, 17.9, 18.4, 19.0, 21.3, 21.8, 24.1, 24.9, 26.3, 27.1 |
| Tetrahydrofuran-hexane | 164.8-166.4 | 167.19 | 88.12 | None | 13.7, 14.8, 16.1, 17.9, 18.4, 19.0, 21.3, 21.8, 24.1, 24.9, 26.3, 27.1 |
| Tetrahydrofuran-methy tert-butyl ether | 166.1-167.1 | 168.25 | 84.29 | None | 13.7, 14.8, 16.1, 17.9, 18.4, 19.0, 21.3, 21.8, 24.1, 24.9, 26.3, 27.1 |
| Isopropanol-methyl tert-butyl ether | 166.2-167.2 | 169.31 | 89.97 | None | 13.7, 14.8, 16.1, 17.9, 18.4, 19.0, 21.3, 21.8, 24.1, 24.9, 26.3, 27.1 |
| Isopropanol-ethyl acetate | 166.7-167.8 | 168.62 | 95.02 | None | 13.7, 14.8, 16.1, 17.9, 18.4, 19.0, 21.3, 21.8, 24.1, 24.9, 26.3, 27.1 |
| Water-methyl tert-butyl ether | 166.4-167.5 | 169.80 | 95.83 | None | 13.7, 14.8, 16.1, 17.9, 18.4, 19.0, 21.3, 21.8, 24.1, 24.9, 26.3, 27.1 |

TABLE 1-continued

Properties of crystalline (1R,2R)-1-methyl-2-(2-methylpropanoyloxy)propyl (2S)-2-amino-3-(3,4-dihydroxyphenyl)propanoate hydrochloride (9) crystallized from various solvents.

| Solvents | m.p. (° C.) | Melting peak on DSC (° C.) | ΔH (g/J) | Hygro-scopicity | XRPD 2θ (deg) |
|---|---|---|---|---|---|
| Water-acetonitrile | 167.1-168.4 | 168.96 | 97.04 | None | 13.7, 14.8, 16.1, 17.9, 18.4, 19.0, 21.3, 21.8, 24.1, 24.9, 26.3, 27.1 |

Example 14

Intracolonic Bioavailability of Levodopa Prodrugs in Rats

Sustained release oral dosage forms, which slowly release therapeutic agents over periods of about 6 to about 24 hours, generally release a significant proportion of the dose within the colon. Thus, therapeutic agents suitable for use in sustained release dosage forms should be colonically absorbed. This experiment was conducted to assess the uptake and resultant plasma/blood levels of levodopa, following intracolonic administration of a compound of Formula (I) with co-administration of carbidopa (intracolonically, intraperitoneally, or orally), and thereby determine the suitability of a compound of Formula (I) for use in an oral sustained release dosage form. Bioavailability of levodopa following co-administration of a compound of Formula (I) and carbidopa was calculated relative to intracolonic administration of levodopa with coadministration of carbidopa (i.p.).

Levodopa was obtained from Sigma-Aldrich (St. Louis, Mo.). Carbidopa was obtained from Spectrum Laboratory Products (Gardena, Calif.). Levodopa hydrochloride salt and levodopa prodrugs of Formula (I) were synthesized from commercial levodopa as described in Examples 1-13. For intracolonic administration, levodopa HCl salt was dissolved in water and levodopa prodrugs were dissolved in sodium phosphate buffer at pH 6.2 or suspended in 0.5% methylcellulose/0.1% Tween 80 in sodium phosphate buffer at pH 7.02.

Male Sprague-Dawley rats (approx. 250 g) with indwelling jugular vein cannulas were obtained from Charles River (Hollister, Calif.). Rats were additionally cannulated in the colon just distal to the cecum. All animals were allowed 48 h to recover from surgery prior to shipping and were acclimated for at least 48 h on site prior to study. Rats were fasted overnight and for the first 4 hours of the study. Water was provided ad libitum.

Two groups of male Sprague-Dawley rats (4-6 rats/group) received intravenous bolus injections of levodopa HCl salt or levodopa prodrug at 5 mg-eq levodopa/kg (mg-eq LD/kg). To determine colonic absorption of levodopa and levodopa prodrugs, four different groups of rats were dosed intracolonically with levodopa HCl salt at 75 mg-eq levodopa/kg or levodopa prodrug at 25 mg-eq levodopa/kg. In all studies, carbidopa (administered as carbidopa monohydrate or carbidopa HCl salt) was co-administered intraperitoneally at 10 mg/kg with levodopa or levodopa prodrug. Blood samples were obtained at intervals up to 24 hours post-dosing. All blood samples were subsequently analyzed for intact prodrug and/or levodopa using LC-MS/MS.

Quenched blood samples were frozen and stored at −80° C. prior to analysis. Samples were analyzed by a sensitive and specific LC-MS/MS method for simultaneous determination of levodopa prodrug and levodopa. The lower limits of quantitation for levodopa was in the range of about 0.004 μg/mL to about 0.02 μg/mL and the upper limit of quantitation was in the range of about 5 μg/mL to about 15 μg/mL.

Concentration data for levodopa and levodopa prodrug in blood were analyzed by noncompartmental methods using WinNonlin™ Software (Version 3.3. Pharsight Corp., Mountain View, Calif.). Non-compartmental analysis was performed on individual profiles. All concentration values below the limit of quantitation (BLQ) were treated as 0 (zero) for the pharmacokinetic analysis. Low concentration values at pre-dose were treated as BLQ. Nominal sample collection time points were used for the calculation of pharmacokinetic parameters. All concentration data were plotted using Sigma-Plot™ (Version 9.0, Systat Software Inc., Point Richmond, Calif.).

The maximum concentration ($C_{max}$) and time to $C_{max}$ ($T_{max}$) were obtained by observation. The apparent elimination half-life ($T_{1/2}$) was obtained by linear regression of three or more log-transformed data points in the terminal phase. The area under the concentration versus time curve (AUC) was obtained by the linear trapezoidal method using concentration data over the dosing interval. The AUC value extrapolated to infinity ($AUC_{inf}$) was calculated as $$AUC_{inf} = AUC_{(0-tlast)} + C_{last}/\lambda_z$$

where $t_{last}$ is the time of the last quantifiable concentration ($C_{last}$) and $\lambda_z$ is the rate constant of the apparent terminal elimination phase.

The bioavailability (F) of levodopa after extravascular dosing of levodopa or prodrug was calculated by comparison to data following intravenous administration of levodopa as follows:

$$F(\%) = 100 \times (AUC_{ex}/Dose_{ex})/(AUC_{i.v.}/Dose_{i.v.})$$

where $AUC_{ex}$ is the area under the levodopa concentration versus time curve in μg·hr/mL following extravascular administration of levodopa or prodrug; $Dose_{ex}$ is the extravascular dose expressed in mg-equivalents of levodopa/kg body weight; $AUC_{i.v.}$ is the area under the levodopa concentration versus time curve in μg·hr/mL following intravenous administration of levodopa; $Dose_{i.v.}$ is the intravenous dose expressed in mg-equivalents of levodopa/kg body weight.

Intracolonic administration of levodopa and intraperitoneal administration of carbidopa to rats results in very low relative colonic bioavailability of levodopa (i.e., only 3.4% of intracolonically administered levodopa). By comparison, intracolonic administration of a compound of Formula (I) with intraperitoneal administration of carbidopa exhibited improved relative intracolonic bioavailability of levodopa by at least 2-fold. For example, the intracolonic bioavailability of levodopa following intracolonic administration of compounds (9) and (11) at 25 mg/kg equivalents of levodopa and intraperitoneal administration of carbidopa at 10 mg/kg to rats provided an intracolonic bioavailability of levodopa that was at least 3 times greater than the intracolonic bioavailability of an equivalent dose of levodopa itself. The data demonstrates that certain levodopa prodrugs can be formulated as compositions suitable for effective sustained oral release and uptake of a compound of Formula (I) and/or levodopa from the colon.

Example 15

Intracolonic Bioavailability of Levodopa Prodrugs in Monkeys

Male Cynomologous monkeys weighing about 3.0 kg were used in the studies. Monkeys were fasted overnight prior to the study until 4 hours after dosing. Waeter was provided ad libitum.

Carbidopa was prepared as a solution (0.72 mg/mL) in sodium acetate buffer pH 5.16. Levodopa prodrug (9) was prepared as a suspension (19.1 mg/mL) in 0.5% methyl cellulose/0.1% Tween-80 in $NaH_2PO_4$ pH 7.02.

Carbidopa (5 mL/kg; 3.33 mg-eq carbidopa/kg) was administered to 4 monkeys, and levodopa prodrug (9) (1 mL/kg; 10 mg-eq levodopa/kg) was administered intracolonically to 4 monkeys. Blood samples were collected at pre-dose and at 0.17, 0.25, 0.5, 0.75, 1, 2, 4, 6, 8, 12, and 24 hours post-dose. About 0.3 mL of blood was collected in pre-chilled $K_2EDTA$ tubes containing 100 μL of 10% sodium metabisulfite. The contents were gently vortexed at low speed to ensure that the sampled blood came into contact with sodium metabisulfite while maintaining ice on the samples at all times. About 0.1 mL of the anticoagulated blood was added to each of 2 pre-chilled cryovials that each contained about 0.3 mL of quenching media (89.3% v/v methanol and 10.7% v/v 4N perchloric acid) within 5 minutes of bleed. Within 30 minutes of blood collection, the samples were centrifuged at about 3,000 rpm, 4° C., for 10 min. The samples were then stored at −70° C.

Blood samples were analyzed as described in Example 14. Pharmacokinetic parameters for levodopa following intracolonic administration of levodopa prodrug (9) is shown in Table 2.

To prepare the oral matrix tablets comprising levodopa prodrug, levodopa prodrug (9), microcrystalline cellulose (Avicel® MCC PH 200 FMC Biopolymer, Newark, Del.), and hydroxypropylmethyl cellulose (Methocel® HPMC K4M, Dow Chemical, Midland, Mich.) in the amounts listed in Table 3 were blended for 5 min in a 100 cc HDPE bottle. Magnesium stearate (NF, Mallinckrodt, Phillipsburg, N.J.) was added to the bottle and blended for an additional 4 min. The blend was weighed and the material compressed (Tabletop Rotary Tablet Press, Minipress-IIBD, GlobePharma, New Brunswick, N.J.) fitted with a 0.3 in×0.657 in capsule-shaped tool to provide tablets weighing about 565 mg or 466 mg. Each tablet contained about 108 mg-eq levodopa.

TABLE 3

Composition of tablets containing levodopa prodrug.

| Component | Formulation 1 (mg) | Formulation 2 (mg) |
| --- | --- | --- |
| Prodrug (9) | 36.65 | 44.44 |
| MCCPH200 | 25.20 | 46.65 |
| HPMC K4M | 36.65 | 7.41 |
| HPMC K15M | — | — |
| Magnesium Stearate | 1.50 | 1.50 |
| Tablet Weights | 565 | 466 |

One group of four to five male Cynomolgus monkeys was used for the study (mean body weight was approximately 3.1 kg). Monkeys were fasted overnight and for the first 4 hours of the study after administration of each test formulation. Water was provided ad libitum.

All formulations were evaluated in a single group of four to five fasted male Cynomolgus monkeys with at least 3 days washout between treatments. Sinemet IR® and Sinemet CR® tablets, each containing 100 mg-eq of levodopa and 25 mg of carbidopa per tablet, were administered orally to monkeys as one tablet per animal. Two different levodopa prodrug sustained release tablet formulations were each dosed orally at 108 mg-eq levodopa (one tablet), together with one 25 mg carbidopa tablet (commercial Lodosyn® tablet, Merck & Co.).

TABLE 2

Pharmacokinetic parameters for levodopa following intracolonic administration of levodopa prdrug (9).

| | $C_{max}$ (μg/mL) | $T_{max}$ (h) | $T_{1/2\text{-}\lambda}$ (h) | $AUC_t$ (μg · h/mL) | $AUC_{inf}$ (μg · h/mL) | $Fic^\dagger$ (%) |
| --- | --- | --- | --- | --- | --- | --- |
| Mean (SD) | 2.17 (0.17) | 0.62 (0.18) | 0.54 (0.04) | 2.92 (0.00) | 2.95 (0.01) | 39.9 (0.1) |

$^\dagger$Fic = bioavailability relative to levodopa IV, 5 mg-eq levodopa/kg IV and 10 mg-eq carbidopa IP, mean AUCinf value of 3.69 μg · h/mL.

Example 16

Pharmacokinetics of Levodopa Prodrugs Following Oral Administration to Monkeys

Commercial levodopa was obtained from Sigma-Aldrich (St. Louis, Mo.) (95.8% w/w to 97.3% w/w purity determined by HPLV/UV assay). Commercial carbidopa was obtained from Spectrum Laboratory Products (Gardena, Calif.). Levodopa prodrugs were synthesized as described in Examples 1-13. Commercial immediate release Sinemet IR® and controlled release Sinemet CR® tablets, each containing 100 mg levodopa and 25 mg carbidopa, were used for the study.

Blood samples were obtained from all animals at intervals over 12 h. At each time approximately 0.4 mL of blood was collected in pre-chilled $K_2EDTA$ tubes containing 50 μL of 10% sodium metabisulfite. Within 30 minutes of blood collection, blood samples were centrifuged and separated for plasma. Plasma samples were stored at or below at least −70° C. Plasma samples were frozen and stored at −80° C. prior to analysis. Prior to analysis, samples were quenched by addition of methanol and perchloric acid. Blood samples were analyzed as described in Example 14.

Figure 2:
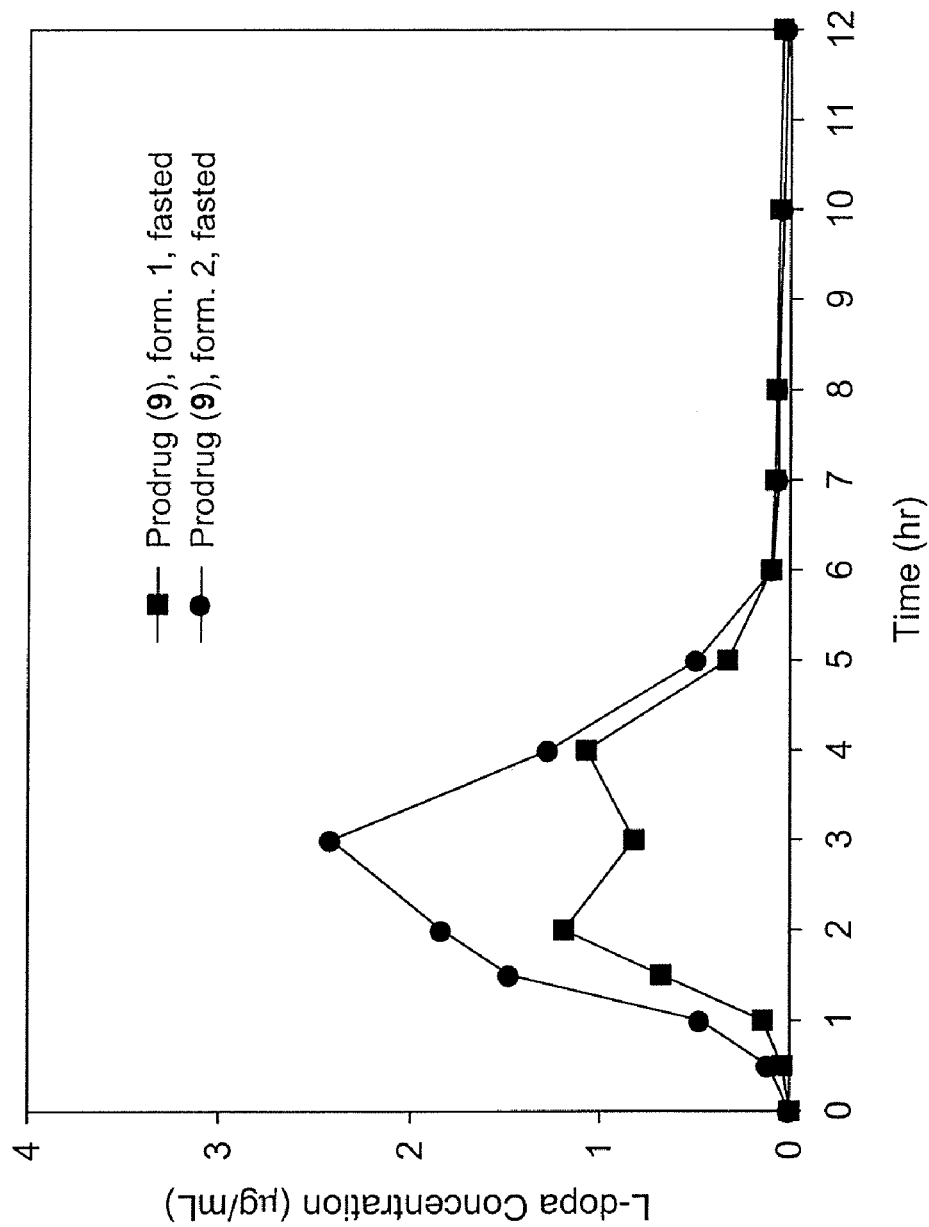
FIG. 2 shows levodopa levels in plasma following oral administration of tablet formulations comprising levodopa prodrug (9) to fasted monkeys with 25 mg carbidopa co-administered i.p.

The mean pharmacokinetic parameters for levodopa in plasma of monkeys following oral administration of commercial Sinemet® tablets or levodopa prodrug formulations is summarized in Table 4. The concentration-time profiles of levodopa in plasma following oral dosing of Sinemet IR®, or Sinemet CR®, and levodopa prodrug formulations is shown in FIG. 1 and FIG. 2.

TABLE 4

Pharmacokinetic parameters for levodopa in plasma following oral administration of levodopa and levodopa prodrug to monkeys.

| Formulation | $C_{max}$ (µg/mL) | $T_{max}$ (h) | $T_{1/2}$ (h) | $AUC_t$ (µg·h/mL) | $AUC_{inf}$ (µg·h/mL) | $C_6$ (µg/mL) | Frel* (%) |
|---|---|---|---|---|---|---|---|
| Sinemet IR | 12.2 (4.2) | 1.4 (0.4) | 2.2 (2.2) | 17.2 (4.0) | 17.3 (4.0) | 0.03 (0.02) | — |
| Sinemet CR | 6.1 (1.7) | 1.8 (0.3) | 1.2 (0.1) | 10.0 (1.6) | 10.0 (1.6) | 0.08 (0.04) | 59.1 (7.8) |
| Prodrug (9) Form. 1 Fasted | 1.4 (0.9) | 2.7 (1.0) | 2.8 (1.7) | 4.0 (2.2) | 4.1 (2.1) | 0.10 (0.03) | 21.8 (13.8) |
| Prodrug (9) Form. 1 Fed | 0.5 (0.2) | 6.3 (1.7) | 2.3 (1.0) | 2.1 (0.3) | 2.3 (0.2) | 0.36 (0.19) | 11.4 (1.8) |
| Prodrug (9) Form. 2 Fasted | 2.7 (1.1) | 2.5 (0.6) | 1.7 (0.9) | 6.9 (2.7) | 7.0 (2.7) | 0.09 (0.05) | 36.3 (20.4) |

Frel (%) = bioavailability relative to Sinemet IR ®.

Example 17

Use of Clinical Trials to Assess the Efficacy of Compounds of Formula (I) in Treating Parkinson's Disease The following clinical study may be used to assess the efficacy of a compound of Formula (I) in treating Parkinson's disease.

Patients with idiopathic PD fulfilling the Queen Square Brain Bank criteria (Gibb et al., *J Neurol Neurosurg Psychiatry* 1988, 51, 745-752) with motor fluctuations and a defined short duration levodopa response (1.5-4 hours) are eligible for inclusion. Clinically relevant peak dose dyskinesias following each morning dose of their current medication are a further pre-requisite. Patients are also required to have been stable on a fixed dose of treatment for a period of at least one month prior to starting the study. Patients are excluded if their current drug regime includes slow-release formulations of levodopa, COMT inhibitors, selegiline, anticholinergic drugs, or other drugs that could potentially interfere with gastric absorption (e.g. antacids). Other exclusion criteria include patients with psychotic symptoms or those on antipsychotic treatment patients with clinically relevant cognitive impairment, defined as MMS (Mini Mental State) score of less than 24 (Folstein et al., *J Psychiatr Res* 1975, 12, 189-198), risk of pregnancy, Hoehn & Yahr stage 5 in off-status, severe, unstable diabetes mellitus, and medical conditions such as unstable cardiovascular disease or moderate to severe renal or hepatic impairment. Full blood count, liver, and renal function blood tests are taken at baseline and after completion of the study.

A randomized, double-blind, and cross-over study design is used. Each patient is randomized to the order in which either levodopa, placebo, or test compound is administered in a single-dose challenge in double-dummy fashion in three consecutive sessions.

Patients are admitted to a hospital for an overnight stay prior to administration of a compound of Formula (I) the next morning on three separate occasions at weekly intervals.

After withdrawal of all anti-parkinsonian medication from midnight the previous day a compound of Formula (I) is administered at exactly the same time in the morning in each patient under fasting conditions.

Patients are randomized to the order of the days on which they receive placebo or a compound of Formula (I). The pharmacokinetics of a compound of Formula (I) is assessed by monitoring the plasma levodopa concentration over time. Prior to administration, a 22 G intravenous catheter is inserted in a patient's forearm. Blood samples of 5 ml each are taken at baseline and 15, 30, 45, 60, 75, 90, 105, 120, 140, 160, 180, 210, and 240 minutes after administering compound of Formula (I) or until a full off-state has been reached if this occurs earlier than 240 minutes after drug ingestion. Samples are centrifuged immediately at the end of each assessment and stored deep frozen until assayed. Plasma levodopa, prodrug, and 3-O-methyl-dopa levels are assessed by high-pressure liquid chromatography (HPLC). On the last assessment additional blood may be drawn for routine hematology, blood sugar, liver, and renal function.

For clinical assessment, motor function is assessed using UPDRS (United Parkinson's Disease Rating Scale) motor score and BrainTest (Giovanni et al., *J Neurol Neurosurg Psychiatry* 1999, 67, 624-629), which is a tapping test performed with the patient's more affected hand on the keyboard of a laptop computer. These tests are carried out at baseline and then immediately following each blood sample until patients reach their full on-stage, and thereafter at 3 intervals of 20 min, and 30 min intervals until patients reach their baseline off-status. Once patients reach their full on-state, video recordings are performed three times at 20 min intervals. The following mental and motor tasks, which have been shown to increase dyskinesia (Duriff et al., *Mov Disord* 1999, 14, 242-245) are monitored during each video session: (1) sitting still for 1 minute; (2) performing mental calculations; (3) putting on and buttoning a coat; (4) picking up and drinking from a cup of water; and (5) walking. Videotapes are scored using, for example, versions of the Goetz Rating Scale and the Abnormal Involuntary Movements Scale to document a possible increase in test compound induced dyskinesia.

Actual occurrence and severity of dyskinesia is measured with a Dyskinesia Monitor (Manson et al., *J Neurol Neurosurg Psychiatry* 2000, 68, 196-201). The device is taped to a patient's shoulder on their more affected side. The monitor records during the entire time of a challenging session and provides a measure of the frequency and severity of occurring dyskinesias.

Results may be analyzed using appropriate statistical methods.

Example 18

Administration of a Compound of Formula (I) for the Treatment of Restless Legs Syndrome A placebo-controlled, cross-over clinical trial is conducted to assess the effects of a compound of Formula (I) on sensory and motor symptoms in patients with restless legs syndrome (Garcia-Borreguero et al., *Neurology* 2002, 11(2), 1573-79). Briefly, twenty patients with RLS (either idiopathic or secondary) are randomized and treated for 6 weeks with either the prodrug or placebo. A compound of Formula (I) is formulated as osmotic sustained release capsules containing a therapeutically effective amount of prodrug (preparation of the sustained release capsules is described in Section 5.1 above) and is administered as appropriate. After a 1-week washout, the patients are crossed over to alternative treatment for 6 weeks. Patients are rated at baseline and at scheduled intervals by the RLS Rating Scale, Clinical Global Impression, pain analog scale, and Pittsburgh Sleep Quality Index. In addition, all-night polysomnography is performed before and after the drug treatment periods (Foldvary-Schaefer et al., *Epilepsia* 2002, 43(12), 1493-1497). A positive result for a compound of Formula (I) is associated with reduced symptoms on all rating scales when compared with the placebo.

Example 19

Animal Model for Assessing Therapeutic Efficacy of Levodopa Prodrugs for Treating Tardive Dyskinesia Vacuous chewing movements (VCM) are a rodent model of tardive dyskinesia (Andreassen et al., *Br J Pharmacol* 1996, 119(4), 751-7; and Shoham et al., *Brain Res* 2004, 1004(1-2), 142-147). In this model, animals are treated chronically with antipsychotics and their vacuous chewing motions are assessed by observation. The model has been shown to be sensitive to differential effects of typical and atypical antipsychotics and potential anti-dyskinetic agents.

Rats are housed in a controlled environment and allowed to acclimatize prior to testing. In order to limit neuroleptic-induced weight gain, food consumption is restricted to 15 g per animal per day. Rats are weighed biweekly throughout the study.

For two weeks prior to administration of test compound, animals are handled daily and habituated to the animal colony and the procedures related to drug administration and video recording. Subsequently (week 0), rats undergo a behavior video recording session following which they are randomized to a haloperidol treatment and a control group. The rats in the treatment group receive an intramuscular injection in the thigh muscles with haloperidol decanoate. The control rats are similarly injected with an equal volume of phosphate buffered saline (PBS). The haloperidol decanoate and saline injections are repeated every four weeks, for 20 weeks. Additional behavior video recording sessions are performed at weeks 12, 20 and 24 (i.e., 4 weeks after the last (fifth) injection). During the injection procedures, rats are handheld with minimal restraint.

On the basis of the results of the behavior assessment performed 24 weeks after the first haloperidol injection (i.e., baseline day), the haloperidol-treated rats are assigned to 10 subject-each treatment groups having an equal mean frequency of observed VCM episodes. One week later (i.e., test day), the groups are randomized to receive one intraperitoneal injection with either vehicle or levodopa prodrug in the vehicle. Rats undergo a 30-150 min video recorded behavior assessment session following the injection. Two weeks after the test day (i.e., post-test day), the video recorded behavior assessment session is repeated to investigate longer-term effects of the experimental treatments.

The videotapes are scored. A VCM episode is defined as a bout of vertical deflections of the lower jaw, which may be accompanied by contractions of the jaw musculature.

Example 20

Animal Model for Assessing Therapeutic Efficacy for Treating Schizophrenia

Morris Water Maze

The Morris Water Maze (MWM) is used as a well-validated hippocampus dependent test of visual-spatial memory. The MWM tests the ability of an animal to locate a hidden platform submerged under water by using extra-maze cues from the test environment. Rats are trained in a pool 1.8 m in diameter and 0.6 m high, containing water at about 26° C. A 10 cm square transparent platform is hidden in a constant position 1 cm below the water level in the pool. Only distal visuo-spatial cues are available to the rats for location of the submerged platform. The rats are given trials to find the hidden platform. The escape latency, i.e., the time required by the rats to find and climb onto the platform, is recorded for up to 120 s. Each rat is allowed to remain on the platform for 30 s, after which it is removed to its home cage. If the rat did not find the platform within 120 s, it is manually placed on the platform and returned to its home cage after 30 s.

Male Sprague-Dawley rats weighing 150-200 g are used. Ten days before the beginning of the experiments, the rats are handled once daily to reduce experimental stress. A composition provided by the present disclosure or control is administered to the rats for three consecutive days before behavioral testing. On each day of behavioral testing the rats are injected with either haloperidol or saline 30 min before behavioral assessment.

PCP-Induced Hyperactivity Model

Male C57Bl/6J mice are used. Mice are received at 6-weeks of age. Upon receipt, mice are assigned unique identification numbers (tail marked) and are group housed with 4 mice/cage in ventilated cages. All animals remain housed in groups of four during the study. All mice are acclimated to the colony room for at least two weeks prior to testing and are subsequently tested at an average age of 8 weeks of age. During the period of acclimation, mice and rats are examined on a regular basis, handled, and weighed to assure adequate health and suitability. Animals are maintained on a 12/12 light/dark cycle. The room temperature is maintained between 20° C. and 23° C. with a relative humidity maintained between 30% and 70%. Chow and water are provided ad libitum for the duration of the study. In each test, animals are randomly assigned across treatment groups.

Test compounds are prepared and administered according to the following procedures. A composition provided by the present disclosure is dissolved or suspended in an appropriate vehicle for administration. The amount of a levodopa prodrug administered can range, for example, from 0.01 mg/kg to 100 mg/kg. As a positive control, clozapine (1 mg/kg) is dissolved in 10% DMSO and administered i.p. at a dose volume of 10 mL/kg at 30 min prior to PCP (phencyclidine) injection. PCP (5 mg/kg) is dissolved in sterile injectable water and administered i.p. at a dose volume of 10 mL/kg.

The Open Filed (OF) test is used to assess both anxiety and locomotor behavior. The open field chambers are Plexiglas square chambers surrounded by infrared photobeams (16×16×16) to measure horizontal and vertical activity. The analysis is configured to divide the open field into a center and periphery zone. Distance traveled is measured from horizontal beam breaks as a mouse moves and rearing activity is measured from vertical beam breaks.

Mice are acclimated to the activity experimental room for at least 1 h to prior to testing. Eight animals are tested in each run. Mice are injected with water or a levodopa prodrug, placed in holding cages for 30 min, and then in the OF chamber for 30 min, removed from the OF chamber and injected with either water or PCP and returned to the OF chambers for a 60-minute session. A different group of mice are injected with either 10% DMSO or clozapine and placed in the OF chamber for 30 min, removed from the OF chamber and injected with PCP (5 mg/kg), and returned to the OF chambers for a 60-minute session.

Data is analyzed by analysis of variance (ANOVA) followed by post-hoc comparisons with Fisher Tests when appropriate. Baseline activity is measured during the first 30 min of the test prior to PCP injection. PCP-induced activity is measured during the 60 min following PCP injection. Statistical outliers that fall above or below 2 standard deviations from the mean are removed from the final analysis. An effect is considered significant if $p<0.05$.

Auditory Startle and Prepulse Inhibition of Startle (PPI)

Young, adult male C57Bl/6J mice are used in this study. Mice are received at 6-weeks of age. Upon receipt, mice are assigned unique identification numbers (tail marked) and are group housed in standard mouse cages. All animals remain housed in groups of four during the study. All mice are acclimated to the colony room for at least two weeks prior to testing and are subsequently tested at an average age of 8-9 weeks of age. During the period of acclimation, mice are examined on a regular basis, handled, and weighed to assure adequate health and suitability. Mice are maintained on a 12 h/12 h light/dark cycle. The room temperature is maintained between 20° C. and 23° C. with a relative humidity between 30% and 70%. Feed and water are provided ad libitum during the study. For testing, animals are randomly assigned across treatment groups and balanced by PPI chamber.

Test compounds are prepared and administered according to the following procedures. A composition provided by the present disclosure is dissolved in an appropriate solvent for administration. An appropriate amount of a levodopa prodrug is administered i.p. 30 minutes prior to testing the normal mouse-PPI portion of the study. As a positive control, clozapine (3 mg/kg) is dissolved in 1% Tween and administered i.p. 60 min prior to testing the PCP-PPI portion of the study. PCP (8 mg/kg phencyclidine) is dissolved in sterile injectable water and administered 30 minutes prior to testing. PCP is delivered at a dose volume of 10 mL/kg.

Acoustic startle measures an unconditioned reflex response to external auditory stimulation. PPI consisting of an inhibited startle response (reduction in amplitude) to an auditory stimulation following the presentation of a weak auditory stimulus or prepulse, has been used as a tool for the assessment of deficiencies in sensory-motor gating, such as those seen in schizophrenia. Mice are placed in the PPI chamber (Med Associates) for a 5 min session of white noise (70 dB) habituation. A test session begins immediately after the 5 min acclimation period. The session starts with a habituation block of 6 presentations of the startle stimulus alone, followed by 10 PPI blocks of 6 different types of trials. Trial types are: null (no stimuli), startle (120 dB), startle plus prepulse (4, 8 and 12 dB over background noise i.e., 74, 78 or 82 dB) and prepulse alone (82 dB). Trial types are presented at random within each block. Each trial begins with a 50 ms null period during which baseline movements are recorded. There is a subsequent 20 ms period during which prepulse stimuli are presented and responses to the prepulse measured. Following a 100 ms pause, the startle stimuli are presented for 40 ms and responses are recorded for 100 ms from startle onset. Responses are sampled every ms. The inter-trial interval is variable with an average of 15 s (range from 10 to 20 s). In startle alone trials the basic auditory startle is measured and in prepulse plus startle trials the amount of inhibition of the normal startle is determined and expressed as a percentage of the basic startle response (from startle alone trials), excluding the startle response of the first habituation block.

For the normal mouse-PPI portion of the study, C57BL/6J mice are treated with vehicle, haloperidol, or composition comprising a levodopa prodrug and placed back in their holding cages. Thirty min following injection of vehicle or haloperidol and 60 min following injection of vehicle or a levodopa prodrug, normal mouse-PPI testing begins.

For the PCP-PPI portion of the study, C57BL/6J mice are treated with vehicle, clozapine, or a levodopa prodrug and returned to their holding cages. Thirty min later, all treatment groups are injected with vehicle or PCP. Thirty min following vehicle or PCP injection, PPI testing begins.

Data is analyzed using appropriate statistical methods. For the PPI analysis, all mice that have a startle response below 100 are removed from the analysis.

Example 21

Animal Model for Assessing Therapeutic Efficacy of Levodopa Prodrugs for Treating Huntington's Disease Neuroprotective Effects in a Transgenic Mouse Model of Huntington's Disease Transgenic HD mice of the N171-82Q strain and non-transgenic littermates are treated with a levodopa prodrug or a vehicle from 10 weeks of age. The mice are placed on a rotating rod ("rotarod"). The length of time at which a mouse falls from the rotarod is recorded as a measure of motor coordination. The total distance traveled by a mouse is also recorded as a measure of overall locomotion. Mice administered levodopa prodrugs that are neuroprotective in the N171-82Q transgenic HD mouse model remain on the rotarod for a longer period of time and travel further than mice administered vehicle.

Malonate Model of Huntington's Disease

A series of reversible and irreversible inhibitors of enzymes involved in energy generating pathways has been used to generate animal models for neurodegenerative diseases such as Parkinson's and Huntington's diseases. In particular, inhibitors of succinate dehydrogenase, an enzyme that impacts cellular energy homeostasis, has been used to generate a model for Huntington's disease (Brouillet et al., *J. Neurochem.* 1993, 60, 356-359; Beal et al., *J. Neurosci.* 1993, 13, 4181-4192; Henshaw et al., *Brain Research* 1994, 647, 161-

166; and Beal et al., *J. Neurochem.* 1993, 61, 1147-1150). The enzyme succinate dehydrogenase plays a central role in both the tricarboxylic acid cycle as well as the electron transport chain in mitochondria. Malonate is a reversible inhibitor of succinate dehydrogenase. Intrastriatal injections of malonate in rats have been shown to produce dose dependent striatal excitotoxic lesions that are attenuated by both competitive and noncompetitive NMDA antagonists (Henshaw et al., *Brain Research* 1994, 647, 161-166). For example, the glutamate release inhibitor, lamotrigine, also attenuates the lesions. Co-injection with succinate blocks the lesions, consistent with an effect on succinate dehydrogenase. The lesions are accompanied by a significant reduction in ATP levels as well as a significant increase in lactate levels in vivo as shown by chemical shift resonance imaging (Beal et al., *J. Neurochem.* 1993, 61, 1147-1150). The lesions produce the same pattern of cellular sparing, which is seen in Huntington's disease, supporting malonate challenge as a useful model for the neuropathologic and neurochemical features of Huntington's disease.

To evaluate the effect of levodopa prodrug in this malonate model for Huntington's disease, levodopa prodrug is administered at an appropriate dose, dosing interval, and route, to male Sprague-Dawley rats. A prodrug is administered for two weeks prior to the administration of malonate and then for an additional week prior to sacrifice. Malonate is dissolved in distilled deionized water and the pH adjusted to 7.4 with 0.1 M HCl. Intrastriatal injections of 1.5 µL of 3 µmol malonate are made into the left striatum at the level of the Bregma 2.4 mm lateral to the midline and 4.5 mm ventral to the dura. Animals are sacrificed at 7 days by decapitation and the brains quickly removed and placed in ice cold 0.9% saline solution. Brains are sectioned at 2 mm intervals in a brain mold. Slices are then placed posterior side down in 2% 2,3,5-triphenyltetrazolium chloride. Slices are stained in the dark at room temperature for 30 min and then removed and placed in 4% paraformaldehyde pH 7.3. Lesions, noted by pale staining, are evaluated on the posterior surface of each section. The measurements are validated by comparison with measurements obtained on adjacent Nissl stain sections. Compounds exhibiting a neuroprotective effect and therefore potentially useful in treating Huntington's disease show a reduction in malonate-induced lesions.

Example 22

Animal Models of Depression

Forced Swim Test in Rats

Male Wistar rats weighting 230-270 g are acclimated to the colony room for a minimum of 1 week, handled daily for at least 4 days and habituated to saline injections for 2 days before the experiments.

Two glass cylinders (20 cm dia×40 cm height) are separated by black opaque partitions and filled with water at about 24° C. to a depth of 30 cm. At this depth a rat cannot stand on the cylinder bottom. The water level is 10 cm from the top. Water is changed before each animal is placed into the water tank. An experimental session consists of two trials. During the conditioning trial, rats are gently placed into the cylinders for 15 min. After the trail, rats are dried and placed into a warm cage with the paper towels for 10-15 min before being returned to their home cages. Twenty-four hours later, for the test trial, animals are placed again into the cylinders for a 5-min test session. Tests are video taped for subsequent quantitative behavioral analysis. The frequency and/or total duration are calculated for each of the following categories: passive/immobile behavior (floating is scored when an animal remains in the water with all four limbs motionless, except for occasional alternate movements of paws and tail necessary to prevent sinking and to keep head/nose above the water); active/mobile behaviors (swimming characterized by rigorous movements with all four legs; paddling characterized by floating with rhythmical simultaneous kicks and occasional pushes off the wall to give speed and direction to the drift), including escape-oriented behaviors (climbing characterized by intense movements with all four limbs, with the two forepaws breaking the surface of the water and being directed against the walls of the cylinder; diving characterized by movements towards the bottom of the cylinder with the rat's head below its hind limbs), and self-directed behaviors (headshakes, vigorous headshakes to get water off the snout and eyes; wiping, rubbing water away from the snout). In addition, at the end of each test trial, fecal boli are counted. A test compound, control, or positive control (e.g., imipramine) is administered prior to the test.

Tail Suspension Test in Mice

Mice are housed in standard laboratory cages and acclimated. Mice are moved from the housing room to the testing area in their home cages and allowed to adapt to the new environment for at least 1 h before testing. Immobility is induced by tail suspension according to the procedure of Stem et al., *Psychopharmacology* 1985, 85, 367-370. Mice are lying individually on a paper adhesive tape, 65 cm above a tabletop. Tape is placed approximately 1 cm from the tip of the tail. Animals are allowed to hang for 6 min and the duration of immobility is recorded. Mice are considered immobile only when hanging passively and completely motionless. Mice from these experiments are sued one week later in locomotor activity studies. A test compound, control, or positive control (e.g., imipramine) is administered prior to the test.

Locomotor Activity

The spontaneous locomotor activity of mice is measured in photoresistor actometers (circular cages, 25 cm in dia, 15 cm high, two light sources, two photoresistors), wherein the animals are placed individually 1 h after injection of a test compound. The number of crossings of light beams is measured during the first 30 min of the experimental session. The first measurement is performed 6 min after placing an animal into the actometer.

The spontaneous locomotor activity of rats is measured in photoresistor actometers (40 cm×40 cm×25 cm, two light sources, two photoresistors), where the animals are placed after administration of a test compound. The number of crossings of light beams is measured during the first 30 min of an experimental session. The first measurement is performed 5 min after placing an animal in the actometer.

Finally, it should be noted that there are alternative ways of implementing the embodiments disclosed herein. Accordingly, the present embodiments are to be considered as illustrative and not restrictive. Furthermore, the claims are not to be limited to the details given herein, and are entitled their full scope and equivalents thereof.

What is claimed is:

1. A compound chosen from:
   (1R,2R)-2-acetyloxy-1-methylpropyl (2S)-2-amino-3-(3, 4-dihydroxyphenyl)propanoate hydrochloride;
   (1R,2R)-1-methyl-2-(2-methylpropanoyloxy)propyl (2S)-2-amino-3-(3,4-dihydroxyphenyl)propanoate mesylate;
   (1R,2R)-2-ethoxycarbonyloxy-1-methylpropyl (2S)-2-amino-3-(3,4-dihydroxyphenyl)propanoate hydrochloride;

(1R,2R)-2-isopropoxycarbonyloxy-1-methylpropyl (2S)-2-amino-3-(3,4-dihydroxyphenyl)propanoate hydrochloride;

(1R,2R)-1-methyl-2-(2-methylpropoxycarbonyloxy)propyl (2S)-2-amino-3-(3,4-dihydroxyphenyl)propanoate, hydrochloride; and (1R,2R)-1-methyl-2-pentyloxycarbonyloxypropyl (2S)-2-amino-3-(3,4-dihydroxyphenyl)propanoate hydrochloride.

2. The compound of claim 1, wherein the compound is (1R,2R)-1-methyl-2-phenylcarbonyloxypropyl (2S)-2-amino-3-(3,4-dihydroxyphenyl)propanoate mesylate.

3. A pharmaceutical composition comprising at least one pharmaceutically acceptable vehicle and a therapeutically effective amount of at least one compound of claim 1 for treating Parkinson's a disease in a patient.

4. A pharmaceutical composition comprising at least one pharmaceutically acceptable vehicle and a therapeutically effective amount of at least one compound of claim 1 for treating a disease in a patient, wherein the disease is chosen from schizophrenia, cognitive impairment disorders, restless legs syndrome, periodic limb movement disorders, tardive dyskinesia, Huntington's disease, hypertension, stroke, excessive daytime sleepiness, dystonia, and memory and learning deficit or loss.

5. The pharmaceutical composition of claim 3, wherein the pharmaceutical composition is a sustained release oral dosage formulation.

6. The pharmaceutical composition of claim 3, further comprising a pharmaceutical agent chosen from a decarboxylase inhibitor, a catechol-O-methyltransferase inhibitor, and a combination thereof.

7. A method of treating Parkinson's disease in a patient comprising administering to a patient in need of such treatment a therapeutically effective amount of at least one compound of claim 1.

8. A method of treating Parkinson's a disease in a patient comprising administering to a patient in need of such treatment a pharmaceutical composition of claim 3.

9. The method of claim 8, wherein the pharmaceutical composition is a sustained release oral dosage formulation.

10. A method of treating a disease in a patient comprising administering to a patient in need of such treatment a compound of claim 1, wherein the disease is chosen from schizophrenia, cognitive impairment disorders, restless legs syndrome, periodic limb movement disorders, tardive dyskinesia, Huntington's disease, hypertension, stroke, excessive daytime sleepiness, dystonia, and memory and learning deficit or loss.

11. A method of treating a disease in a patient comprising administering to a patient in need of such treatment a pharmaceutical composition of claim 4, wherein the disease is chosen from schizophrenia, cognitive impairment disorders, restless legs syndrome, periodic limb movement disorders, tardive dyskinesia, Huntington's disease, hypertension, stroke, excessive daytime sleepiness, dystonia, and memory and learning deficit or loss.

12. The method of claim 10, wherein the pharmaceutical composition comprises a pharmaceutical agent chosen form a decarboxylase inhibitor, a catechol-O-methyltransferase inhibitor, and a combination thereof.

13. The method of claim 11, wherein the pharmaceutical composition comprises a pharmaceutical agent chosen form a decarboxylase inhibitor, a catechol-O-methyltransferase inhibitor, and a combination thereof.

14. The pharmaceutical composition of claim 4, wherein the pharmaceutical composition is a sustained release oral dosage formulation.

15. The pharmaceutical composition of claim 4, wherein the pharmaceutical composition comprises a pharmaceutical agent chosen form a decarboxylase inhibitor, a catechol-O-methyltransferase inhibitor, and a combination thereof.

* * * * *